United States Patent [19]
Jones et al.

[11] Patent Number: 5,843,637
[45] Date of Patent: Dec. 1, 1998

[54] METHODS FOR IDENTIFYING NON-ESSENTIAL GENES OF THE HUMAN CYTOMEGALOVIRUS GENOME AND FOR SCREENING FOR INHIBITORS OF HUMAN CYTOMEGALOVIRUS

[75] Inventors: Thomas R. Jones, Nyack; Viera P. Muzithras, Monroe, both of N.Y.; Yakov Gluzman, Upper Saddle River, N.J.

[73] Assignee: American Cyanamid Company, Madison, N.J.

[21] Appl. No.: 463,175

[22] Filed: Jun. 5, 1995

Related U.S. Application Data

[62] Division of Ser. No. 291,258, Aug. 16, 1994, abandoned, which is a continuation of Ser. No. 906,777, Jun. 30, 1992, abandoned, which is a continuation-in-part of Ser. No. 726,431, Jul. 5, 1991, abandoned.

[51] Int. Cl.$^6$ ................................. C12Q 1/70; C12Q 1/68
[52] U.S. Cl. ..................................................... 435/5; 435/6
[58] Field of Search ................................. 435/5, 6, 69.1, 435/172.3, 325, 320.1; 536/23.1, 23.2, 23.72; 935/22, 23, 32

[56] References Cited

U.S. PATENT DOCUMENTS 5,026,635  6/1991  Ferguson et al. ............................ 435/5

FOREIGN PATENT DOCUMENTS

| 0074808 | 3/1983 | European Pat. Off. . |
| 335784 | 4/1991 | Japan . |
| WO 90/11357 | 10/1990 | WIPO . |

OTHER PUBLICATIONS

Weston et al., "Sequence of the Short Unique Region, Short Repeats, and Part of the Long Repeats of Human Cytomegalovirus," J. Mol. Biol., 192(2):177–208 (1986).

Gretch et al., "A Multigene Family Encodes the Human Cytomegalovirus Glycoprotein Complex gcII (gp47–52 Complex)," J. Virology, 62(6):1956–1962 (1988).

Spaete et al., "Insertion and deletion mutagenesis of the human cytomegalovirus genome," Proc. Natl. Acad. Sci. USA, 84(20):7213–7217 (1987).

Jefferson et al., "β–Glucuronidase from *Escherichia coli* as a gene–fusion marker," Proc. Natl. Acad. Sci. USA, 83(22):8447–8451 (1986).

Jones et al., "A Cluster of Dispensable Genes within the Human Cytomegalovirus Genome Short Component: IRS1, US1–US5, and the US6 Family," J. Virology 66(4):2541–46 (1992).

Jones et al., "Replacement Mutagenesis of the Human Cytomegalovirus Genome: US10 and US11 Gene Products are Non–essential," J. Virology 65(11):5860–5872 (1991).

Stasiak et al., "Transactivation of the Cytomegalovirus ICP 36 Gene Promotor Requires the α Gene Product TRS1 in Addition to IE1 and IE2," J. Virology, 66(2):1050–1058 (1992).

Takekoshi et al. (1991) Gene 101:209–213, May 1991.

Jefferson et al. (1986) Proc. Natl. Acad. Sci. USA 83:8447–8451, Nov. 1986.

*Primary Examiner*—George C. Elliott
*Assistant Examiner*—Robert Schwartzman
*Attorney, Agent, or Firm*—Elizabeth M. Barnhard; Anne M. Rosenblum

[57] ABSTRACT

This invention relates to a method for identifying non-essential genes of the human cytomegalovirus (HCMV) genome through the insertion of a β-glucuronidase marker gene into a specified HCMV gene, such that, if the product of the HCMV gene is not expressed, the gene is identified as non-essential for replication of HCMV. This invention also relates to a method of screening for compounds which inhibit HCMV by the insertion of the β-glucuronidase marker gene into a HCMV gene, such that the enzyme marker is expressed and cleaves a conjugate chemical substrate in an assay system to yield a detectable fluorescing product or to result in a color change. This invention further provides the gene responsible in HCMV early cytopathic effect.

7 Claims, 36 Drawing Sheets

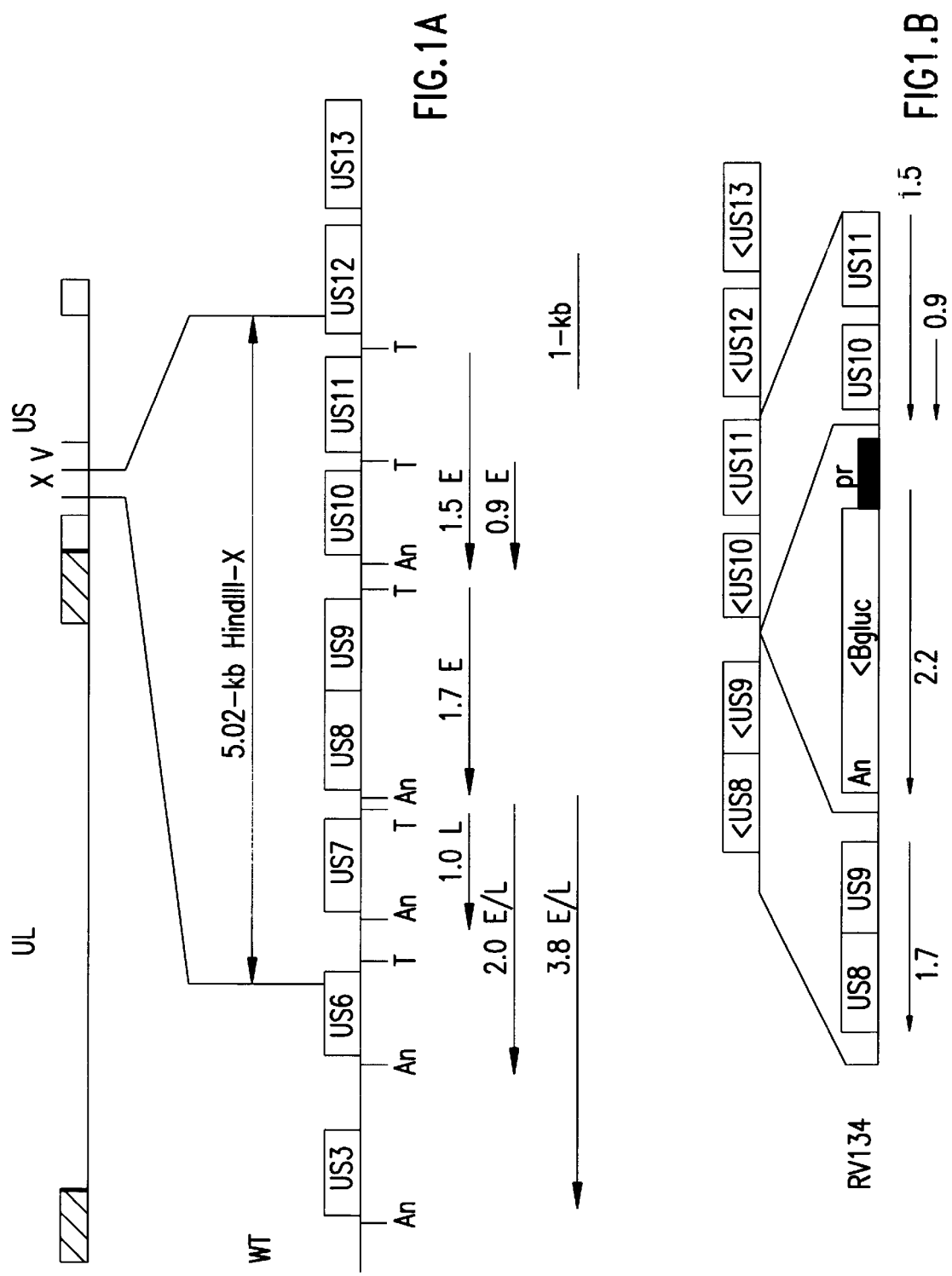

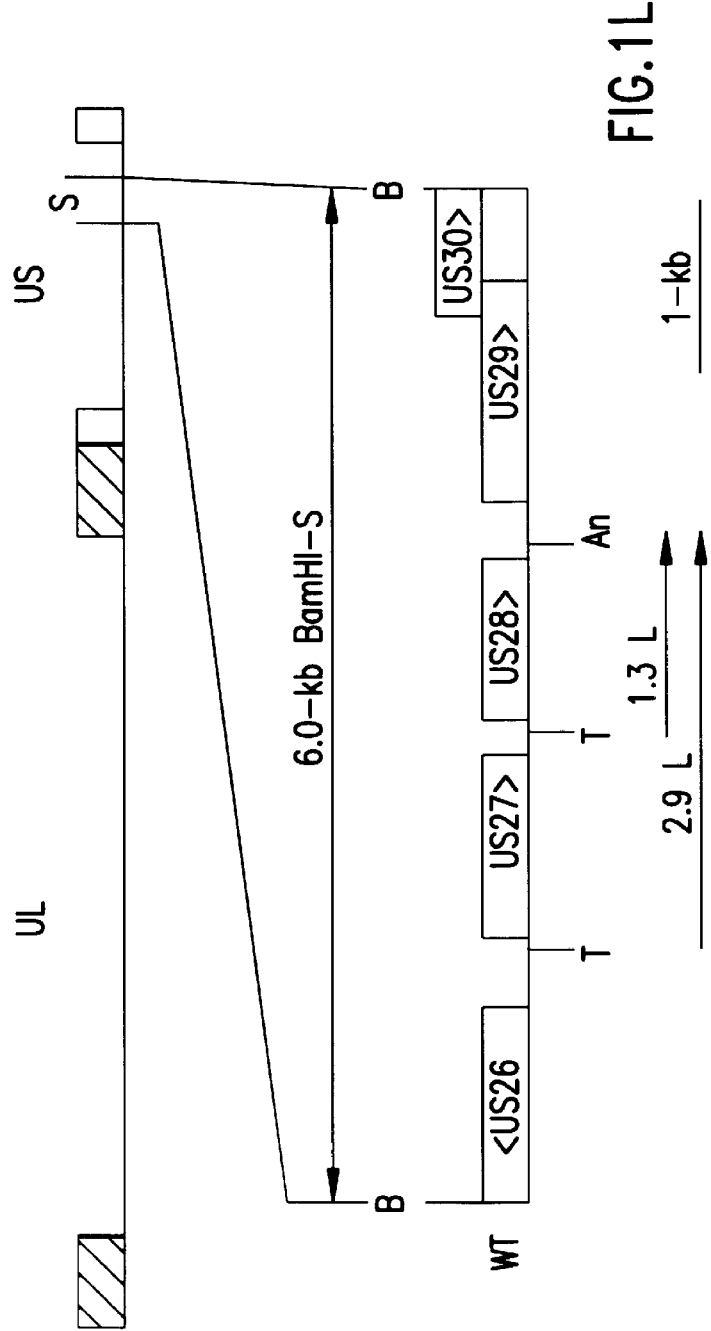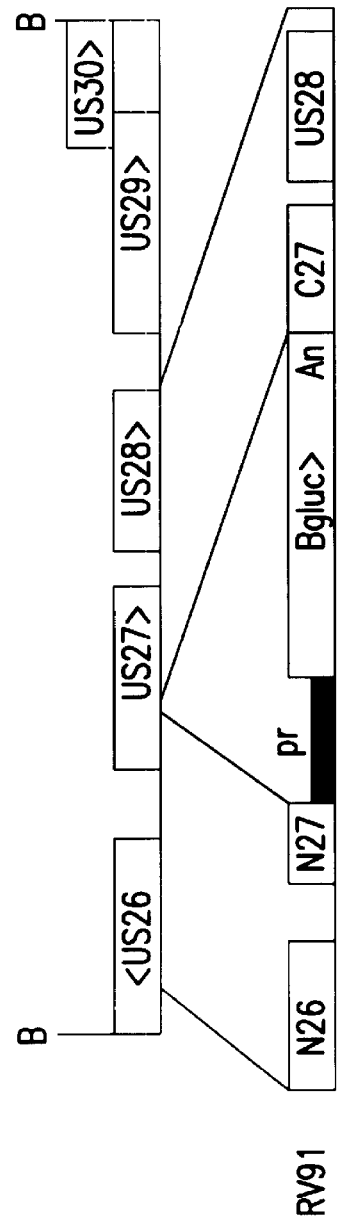
FIG.1L
FIG.1M

AD169

RV670

UNINFECTED

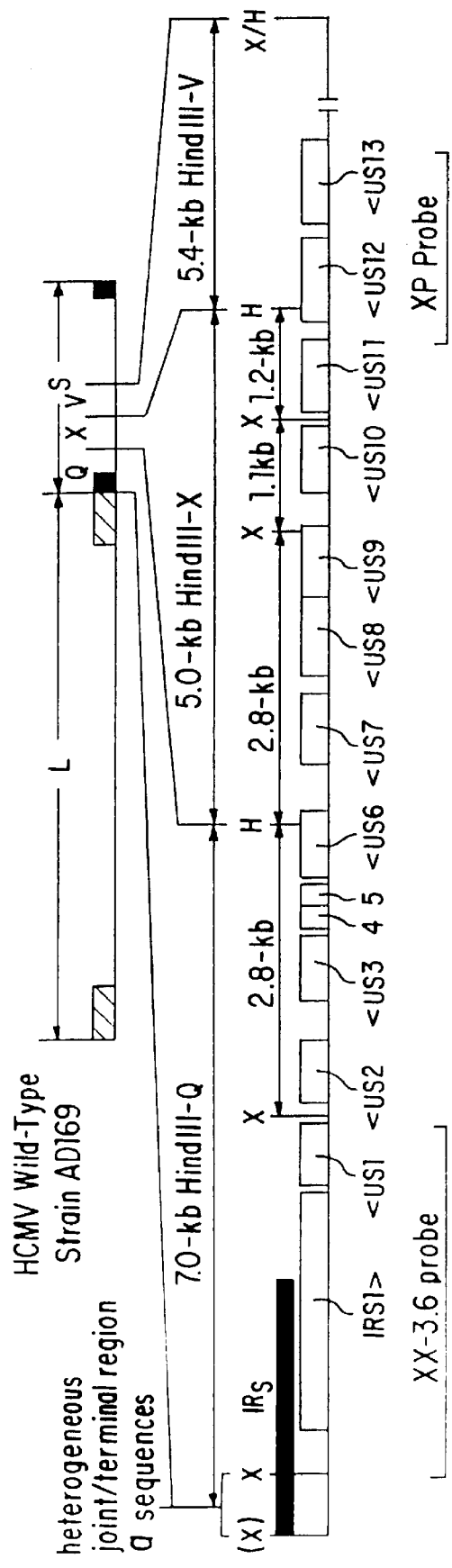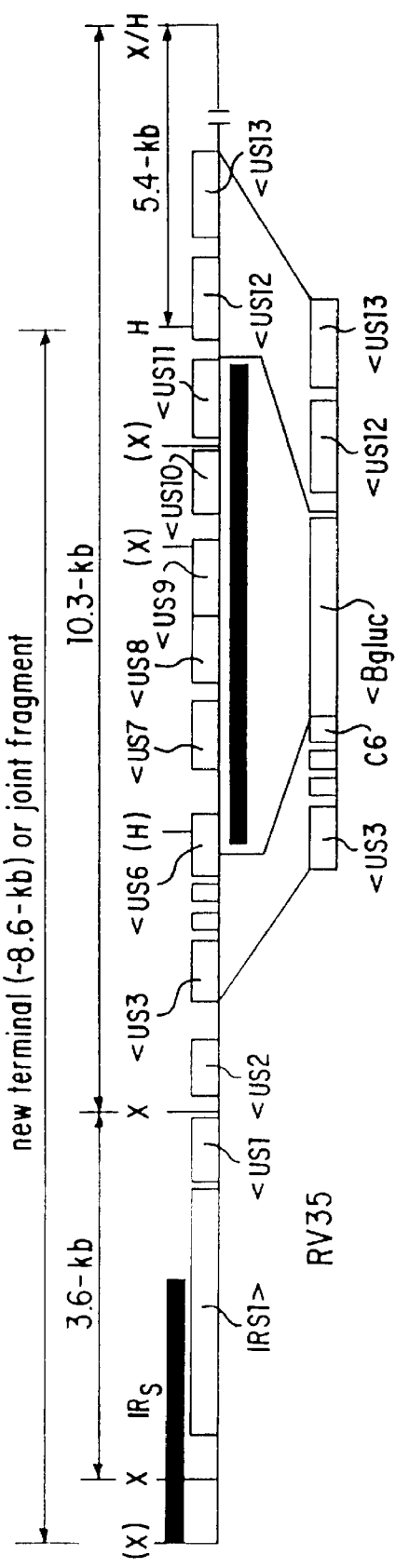
FIG. 11A
FIG. 11B

RV5122 moi=2

RV47 moi=2

RV35 moi=2

RV46 moi=2

RV46 moi = 10

AD169 moi = 10

RV5151 moi = 2

METHODS FOR IDENTIFYING NON-ESSENTIAL GENES OF THE HUMAN CYTOMEGALOVIRUS GENOME AND FOR SCREENING FOR INHIBITORS OF HUMAN CYTOMEGALOVIRUS

This is a division of application Ser. No. 08/291,258, filed on Aug. 16, 1994, now abandoned, which is a continuation of application Ser. No. 07/906,777, filed on Jun. 30, 1992, now abandoned, which, in turn, is a continuation-in-part of application Ser. No. 07/726,431, filed Jul. 5, 1991, abandoned, the contents of which are hereby incorporated by reference into the present disclosure.

Throughout this application various publications are referred to by arabic numerals within parenthesis to more fully describe the state of the art to which this invention pertains. A full bibliographic citation for each reference is provided at the end of the specification, immediately preceding the claims. The contents of these publications are hereby incorporated by reference into this specification.

BACKGROUND OF THE INVENTION

Human cytomegalovirus (HCMV) is a beta-herpesvirus and is an important opportunistic pathogen of immunocompromised adults and can cause neurological abnormalities in some infants infected in utero (1). Such infected individuals are prone to suffer from a variety of diseases, including retinitis and systemic sequelae. The 230 kilobase (kb) genome of HCMV is similar in structure to that of herpes simplex virus (HSV), another human herpesvirus (2). HCMV has long and short unique regions, UL and US, respectively, each bounded by inverted repetitions. The UL region is bounded by the TRL (terminal repeat of the long) region and the IRL (inverted repeat of the long) region. The US region is bounded by the TRS (terminal repeat of the short) region and the IRS (inverted repeat of the short) region. Sequencing of the entire HCMV genome was completed recently (3). Sequencing indicates that the cytomegalovirus genome contains over 200 significant open reading frames. To date, relatively few of these open reading frames have been studied as to the function of the proteins which they may encode.

In the HSV system, the analysis of viral mutants has proven to be invaluable in the study of the function of many viral genes. Several temperature-sensitive mutants of HSV have been described. Other studies of HSV mutants have exploited the viral thymidine kinase gene as a selectable marker for site-directed mutagenesis (4–7). Random mutagenesis of HSV through the use of mini-Mu phage and transposon Tn5 has also been reported (8,9).

More recently, the prokaryotic β-galactosidase gene has been used for site-directed insertion into the HSV genome, allowing for the easy identification of viral mutants as blue plaques after overlay with a chromogenic substrate, X-gal (10,11). In contrast to conditionally lethal mutants in which mutations lie in essential genes, these latter methodologies offer the advantage that mutants in non-essential genes can be created and identified. These successful strategies for the creation of HSV mutants have not been employed to any great extent in the HCMV system.

Probably due to the long replication cycle of this virus, there have only been a few reports concerning the creation or analysis of HCMV temperature-sensitive mutants. Due to the limited host range of HCMV in tissue culture (human diploid fibroblasts), mutagenesis by exploitation of a thymidine kinase gene would be exceedingly difficult.

To date, the only successful site-directed insertion of a marker gene into the genome of HCMV has been the insertion of β-galactosidase within a repeat sequence region bounding UL (12).

However, genomic DNA analyses (12) of this recombinant indicated that an unexpected deletion of 5.5-kb of viral DNA sequences adjacent to the site of the insertion had occurred. One hypothesis given for this deletion was that the size of wild-type DNA is very close to the maximal size of packageable viral DNA, so that large insertions into the wild-type genome are not tolerated without a compensatory deletion elsewhere.

At present, there are few therapeutic agents approved for use against HCMV-infected patients. Ganciclovir, a nucleoside analog sold by Syntex Laboratories, Inc., under the tradename CYTOVENE™, is approved for use against HCMV-induced retinitis. However, ganciclovir is associated with side effects such as neutropenia and azoospermia. In addition, it has low oral bioavailability and thus must be administered intravenously.

Accordingly, there is a need for additional therapeutic agents against HCMV having decreased side effects and improved modes of administration.

SUMMARY OF THE INVENTION

This invention is directed to the construction of genetically stable β-glucuronidase marker-expressing HCMV recombinants by site-directed insertional mutagenesis. The β-glucuronidase gene is inserted by replacing a portion of the HCMV gene with the β-glucuronidase gene. The β-glucuronidase gene is also inserted so as to replace portions of two or more HCMV genes. Alternatively, the β-glucuronidase expression cassette gene is inserted by addition to an HCMV gene so as to disrupt that HCMV gene (or intergenic region) without deleting a portion of the viral genome.

Recombinant HCMV viruses will not express the wild-type gene product of a gene into which the β-glucuronidase gene has been inserted. Therefore, if the virus replicates, the HCMV gene with the insertion is not essential for viral growth. A non-essential gene is to be distinguished from an essential gene, in whose absence the virus will not replicate. A non-essential gene may be a beneficial gene, in which case the replacement of such beneficial gene will result in a virus that replicates at a much slower rate than that of the wild-type virus. Although it has been shown to have wide application in plant and nematode systems (24), the use of β-glucuronidase as a marker gene in mammalian systems has not been reported previously.

These marker-expressing recombinants are used in two ways: (1) to ascertain whether one or more HCMV genes are non-essential for growth in tissue culture; and (2) in an assay method for screening for inhibitors of HCMV.

The insertional mutagenesis with the β-glucuronidase genes can be made in the various regions of the HCMV genome, such as the US and UL regions, as well as in the repeat regions bounding US and UL. In particular, the insertions are made within the US6 gene family, which is located in the US region of the HCMV genome and is comprised of six open reading frames (US6 through US11) which share limited amino acid homology (14) and may encode glycoproteins, such as gcII (15, 16).

Accordingly, it is an object of this invention to insert a genetically stable β-glucuronidase marker gene into one or more genes of the HCMV genome.

It is a further object of this invention to achieve this insertion without deletions in other regions of the HCMV viral genome.

It is yet another object of this invention to set forth a method for identifying non-essential genes of HCMV through the insertion of the β-glucuronidase marker gene into one or more specified HCMV genes, such that, if the wild-type product of each such HCMV gene is not expressed, but viral replication occurs and that other HCMV gene products in the HCMV genome are expressed, each such gene is identified as non-essential for replication of HCMV.

It is an additional object of this invention to demonstrate that β-glucuronidase is suitable for use as a marker gene in a mammalian expression system.

It is another object of this invention to insert a β-glucuronidase marker gene into a gene of HCMV, such that the enzyme marker is expressed and is used for screening for compounds which inhibit HCMV.

Figure 1C:
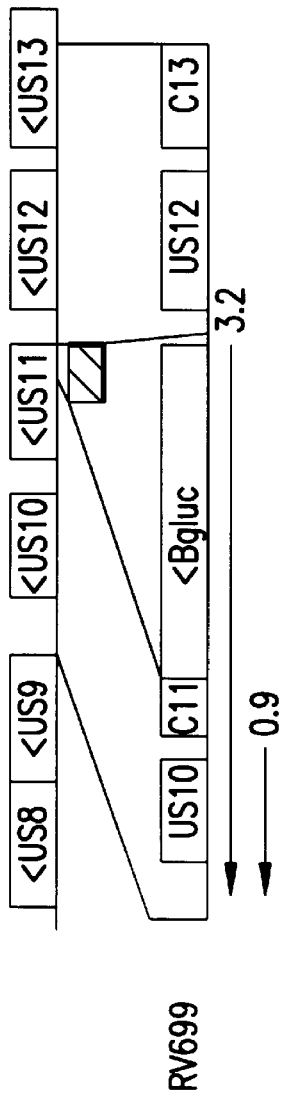
FIGS. 1A–O depicts the organization of recombinant virus (RV) genomes. In Panel A, the first line depicts the location of the US6 family containing a 5.02 kilobase HindIII-X DNA fragment in the HCMV strain AD169 wild-type (WT) genome. The adjacent HindIII-V DNA fragment is also shown. The shaded boxes are the inverted repeats which bind the UL and the clear boxes are those which bind the US. Below it is an expansion of this region showing the organization of the US6 family of genes and neighboring genes. Some of the major transcripts from this region, which were mapped previously (17), are indicated, along with their kinetic class (early, E; late, L), and their size given in kilobases (kb). The direction of transcription is right to left. Transcription initiation site, T; polyadenylation site, An.

Panel B depicts the genomic organization of RV134. This recombinant contains a 2.83-kb insertion of a β-glucuronidase expression cassette in the US10-US9 intergenic region as shown. No HCMV genomic sequences are deleted by this insertion. The arrowhead (>) indicates the amino terminal to carboxyl terminal direction of an open reading frame. The second line (in this panel, as well as panels C through K and M through O) shows the organization of the relevant region of the linearized plasmid constructed to make the recombinant virus. The expected transcripts from this region are shown and their size given in kb. The black box is the 2.7E promoter, pr; the tk polyadenylation signal adjacent to the β-glucuronidase gene is shown as An.

Panel C depicts the genomic organization of RV699. The β-glucuronidase gene is inserted at the US11 transcription initiation site and replaces 220 bases (b) downstream from there, including the sequences encoding the N-terminal 62 amino acids (out of 215) of US11. This replacement results in a 1.68-kb increase in genome size. The region deleted is shown by a shaded box just below the first line. The endogenous US11 promoter controls transcription of β-glucuronidase in this construct. In this and other panels, partial US open reading frames are indicated in the schematics by either N (for amino terminal) or C (for carboxy terminal) followed by their number. For example, just downstream to the β-glucuronidase are the sequences encoding the C-terminal 153 amino acids of the US11 open reading frame (labelled C11). Both the 3.2- and 0.9-kb transcripts utilize the endogenous polyadenylation site downstream of US10.

Panel D depicts the genomic organization of RV131. The β-glucuronidase gene is inserted at the US10 transcription initiation site and replaces 407-b downstream from there, including the sequences encoding the N-terminal 120 amino acids (out of 185) of US10. This replacement results in a 1.49-kb increase in genome size. The region deleted is shown by the shaded box. Only the sequences encoding the C-terminal 65 amino acids remain (labelled C10). β-glucuronidase gene expression is controlled by the endogenous US10 promoter. The 3.0- and 2.4-kb transcripts are 3' co-terminal at the polyadenylation site downstream of US10.

Panel E depicts the genomic organization of RV67. The β-glucuronidase gene is inserted at the US11 transcription initiation site and replaces 1.12-kb downstream from there, including all of the US11 coding region and all but the sequences encoding the C-terminal 65 amino acids of US10 (labelled C10). The region deleted is shown by the shaded box. This replacement results in a 0.78-kb increase in genome size. β-glucuronidase gene expression is controlled by the US11 promoter. Only a 2.3-kb transcript is predicted.

Panel F depicts the genomic organization of RV145. The 2.7E promoter driven β-glucuronidase gene is inserted at the US10 transcription initiation site and replaces 407-b downstream from there, including the sequences encoding the amino terminal 120 (out of 185 total) amino acids of US10. This replacement results in a 2.26-kb increase in genome size. The region deleted is shown by the shaded box. Only the sequences encoding the carboxy terminal 65 amino acids of US10 remain (labeled C10). RV145 differs from RV131 only by the 2.7E promoter controlling β-glucuronidase gene expression in the former.

Panel G depicts the genomic organization of RV80. The β-glucuronidase gene insertion replaces the 5' untranslated sequences, all the US9 coding sequences, and most of the US8 coding sequences (encoding 172 of 235 amino acids). Only the sequences encoding the carboxy terminal 63 amino acids of US8 remain (labeled C8). This replacement results in a 0.81-kb increase in genome size. The region deleted is shown by a shaded box just below the first line. β-glucuronidase gene expression is controlled by the endogenous US9 promoter.

Panel H depicts the genomic organization of RV725. The 2.7E promoter driven β-glucuronidase gene is inserted at the beginning of the US7 open reading frame and replaces most of its coding sequences (encoding 199 of 225 amino acids). Aside from sequences encoding the three amino terminal amino acids, only sequences encoding the 23 carboxy terminal amino acids remain (labeled C7). This replacement results in a 2.07-kb increase in the genome size. The region deleted is shown by a shaded box just below the first line.

Panel I depicts the genomic organization of RV69. The β-glucuronidase gene insertion replaces the 5' untranslated sequences and most of the coding sequences (encoding 120 of 183 amino acids) of the US6 open reading frame. Only the sequences encoding the carboxy terminal 63 amino acids of US6 remain (labeled C6). This replacement results in a 1.52-kb increase in genome size. The region deleted is shown by a shaded box just below the first line. β-glucuronidase gene expression is controlled by the endogenous US6 promoter.

Panel J depicts the genomic organization of RV102. The 2.83-kb β-glucuronidase expression cassette (as in RV134; FIG. 1B) insertion disrupts the US13 open reading frame. It separates the sequences encoding the amino terminal 98 amino acids from those encoding the carboxy terminal 163 amino acids.

Panel K depicts the genomic organization of RV88. The 2.83-kb β-glucuronidase expression cassette (as in RV134;

FIG. 1B) insertion disrupts the US12 open reading frame. It separates the sequences encoding the amino terminal 127 amino acids from those encoding the carboxy terminal 154 amino acids.

Panel L depicts the location of the BamHI-S DNA fragment within the US region of the HCMV strain AD169 wild-type (WT) genome. The second line is an expansion of this region showing the organization of open reading frames US26 through US30. The approximate locations of transcripts arising from US27 and US28 open reading frames are indicated (29).

Panel M depicts the genomic organization of RV91. The 2.83-kb β-glucuronidase expression cassette (as in RV134; FIG. 1B) insertion disrupts the US27 open reading frame. It separates the sequences encoding the amino terminal 116 amino acids from those encoding the carboxy terminal 246 amino acids.

Panel N depicts the genomic organization of RV92. The β-glucuronidase expression cassette (as in RV134; FIG. 1B) is inserted such that it replaces the sequences encoding amino acids 77–143 (out of a total 323 amino acids) of US28. The remaining amino terminal 76 amino acids and carboxy terminal 180 amino acids are labeled N28 and C28, respectively. This replacement results in a 2.64-kb increase in genome size. The region deleted is shown by a shaded box just below the first line.

Panel O depicts the genomic organization of RV101. The β-glucuronidase expression cassette (as in RV134; FIG. 1B) is inserted such that it replaces the sequences encoding the carboxy terminal 246 amino acids (out of 362 total amino acids) of US27, the intergenic sequences between US27 and US28, and the 143 amino terminal amino acids (out of 323 total amino acids) of US28. Only the 116 amino terminal amino acids of US27 (labeled N27) and carboxy terminal 180 amino acids of US28 (labeled C28) remain of these open reading frames. This replacement results in a 1.46-kb increase in genome size. The region deleted is shown by a shaded box just below the first line.

FIGS. 2A–E depicts the Southern blot analysis of recombinant HCMV DNA. Panel A is a schematic of the HCMV genome in the prototype orientation (2), with an expanded view of the HindIII-Q,-X, and -V DNA regions. The open boxes are the US6 family open reading frames, US6 through US11 (3). The locations of HindIII (H) and XhoI (X) restriction endonuclease sites are shown. The kb between each of the indicated restriction endonuclease sites is given. The locations of the HCMV-derived probes are shown. The location of the β-glucuronidase expression cassette insertion in RV134 is indicated by (a). The location of the β-glucuronidase gene insertion and the extent of the wild-type sequences deleted in RV131, RV699, and RV67 are indicated by bracketed regions (b), (c), and (d), respectively. Viral DNAs are digested with HindIII (lanes 1, 3, 5, 7, and 9) or HindIII/XhoI (lanes 2, 4, 6, 8, and 10) and electrophoresed in a 0.6% agarose gel.

Panel B depicts the hybridization of the DNAs, after transfer to a nylon membrane, with an HCMV HindIII-X fragment-derived XbaI/EcoRI (XE) probe. The DNAs are from RV134 (lanes 1 and 2), RV699 (lanes 3 and 4), RV131 (lanes 5 and 6), wild-type strain AD169 (lanes 7 and 8), and RV67 (lanes 9 and 10). Lanes M contain end-labeled g HindIII DNA markers whose size is given in kb to the right of each panel. The location of the hybridizing DNA fragments from wild-type is indicated to the left of each panel either by size (in kb) or by the conventional letter designation. All lanes are from the same gel, but different (optimal) autoradiogram exposures are used to make the figure.

Panel C depicts the hybridization of the DNAs, after transfer to a nylon membrane, with a β-glucuronidase gene probe. The various lanes have been previously described hereinabove for panel B of FIG. 2.

Panel D depicts the hybridization of the DNAs, after transfer to a nylon membrane, with a HindIII-Q fragment-derived HindIII/XhoI (HX) probe. The various lanes have been previously described hereinabove for panel B of FIG. 2.

Panel E depicts the hybridization of the DNAs, after transfer to a nylon membrane, with an XbaI/PstI fragment probe (XP) containing some HindIII-X and -V sequences. The various lanes have been previously described hereinabove for panel B of FIG. 2.

FIGS. 3A–E depicts the Northern blot analysis of RV134-infected cell RNAs.

Panel A depicts the hybridization of RNA from unifected HFF cells (lane U), immediate-early times postinfection ("p.i.") (lane IE), early times p.i. (lane E) or late times p.i. (lane L) with the β-glucuronidase gene riboprobe. The cells are infected with either wild-type (WT) HCMV strain AD169 or RV134 as indicated. The positions of the 28S and 18S rRNAs are shown. The sizes of hybridizing RNAs are given in kb. The β-glucuronidase gene-containing readthrough transcript (RT) indicated.

Panel B depicts the hybridization of RNA from uninfected HFF cells (lane U), immediate-early times postinfection ("p.i.") (lane IE), early times p.i. (lane E) or late times p.i. (lane L) with the US10 riboprobe AB. The cells are infected with either wild-type (WT) HCMV strain AD169 or RV134 as indicated. The position of the 28S and 18S rRNAs are shown. The sizes of hybridizing RNAs are given in kb. The β-glucuronidase gene-containing readthrough transcript (RT) is indicated.

Panel C depicts the hybridization of RNA from uninfected HFF cells (lane U), immediate-early times postinfection ("p.i.") (lane IE), early times p.i. (lane E) or late times p.i. (lane L) with the US8-US9 riboprobe PP. The cells are infected with either wild-type (WT) HCMV strain AD169 or RV134 as indicated. The position of the 28S and 18S rRNAs are shown. The sizes of hybridizing RNAs are given in kb. The β-glucuronidase gene-containing readthrough transcript (RT) is indicated.

Panel D depicts the hybridization of RNA from uninfected HFF cells (lane U) or late times p.i. (lanes L) with the US9-US10 intergenic riboprobe SA. Lane L* in panel D contains RNA from cells which are infected and maintained in the presence of 100 mg/ml of PFA (phosphonoformate trisodium, Foscarnet, FOSCAVIR™, Astra) until late times p.i.

The cells are infected with either wild-type (WT) HCMV strain AD169 or RV134 as indicated. The position of the 28S and 18S rRNAs are shown. The sizes of hybridizing RNAs are given in kb. The β-glucuronidase gene-containing readthrough transcript (RT) is indicated.

Panel E depicts a schematic of the US8-US11 region from wild-type strain AD169 of HCMV. The previously mapped wild-type transcripts containing US10-US11 sequences are shown above the schematic. The position of the β-glucuronidase gene expression cassette insertion is indicated by (#). The positions of the HCMV gene-derived riboprobes are indicated. Restriction endonuclease sites, some of which are used for cloning the fragments for riboprobes, are: ApaI (A), BsmI (B), PstI (PS), PvuII (Pv), XbaI (Xb), and XhoI (Xh).

FIGS. 4A–D depicts the Northern blot analysis of RV699-infected cell RNAs.

Panel A depicts the hybridization of RNA from uninfected HFF cells (lane U), immediate-early times postinfection ("p.i.") (lane IE), early times p.i. (lane E) or late times p.i. (lane L) with the β-glucuronidase gene riboprobe. The positions of the 28S and 18S rRNAs are shown. The sizes of hybridizing RNAs are given in kb. The transcript originating from the cryptic promoter within the β-glucuronidase gene is indicated with an asterisk (*).

Panel B depicts the hybridization of RNA from uninfected HFF cells (lane U), immediate-early times postinfection ("p.i.") (lane IE), early times p.i. (lane E) or late times p.i. (lane L) with the US10 riboprobe AB. The positions of the 28S and 18S rRNAs are shown. The sizes of hybridizing RNAs are given in kb. The transcript originating from the cryptic promoter within the β-glucuronidase gene is indicated with an asterisk (*).

Panel C depicts the hybridization of RNA from uninfected HFF cells (lane U), immediate-early times postinfection ("p.i.") (lane IE), early times p.i. (lane E) or late times p.i. (lane L) with the US11 riboprobe XX. The positions of the 28S and 18S rRNAs are indicated. The sizes of hybridizing RNAs are given in kb. The transcript originating from the cryptic promoter within the β-glucuronidase gene is indicated with an asterisk (*).

Panel D depicts a schematic of the US8-US11 region from wild-type strain AD169 of HCMV. Restriction endonuclease sites used for cloning the fragments for riboprobes are shown: ApaI (A), BsmI (B), XbaI (Xb), and XhoI (Xh). The previously mapped wild-type transcripts containing US10-US11 sequences are shown above the schematic. The RNAs expected as result of the recombination which yields RV699 are shown below the schematic. The shaded box indicates the position and extent of the sequences which are deleted and replaced by the β-glucuronidase gene (not drawn to scale) in RV699-infected cell RNAs. The positions of the HCMV gene-derived riboprobes are indicated.

FIGS. 5A–D depicts the Northern blot analysis of RV131-infected cell RNAs.

Panel A depicts the hybridization of RNA from uninfected HFF cells (lane U), immediate-early times postinfection ("p.i.") (lane IE), early times p.i. (lane E) or late times p.i. (lane L) with the β-glucuronidase gene riboprobe. The positions of the 28S and 18S rRNAs are shown. The size of hybridizing RNAs are given in kb. The transcript originating from the cryptic promoter within the β-glucuronidase gene is indicated with an asterisk (*).

Panel B depicts the hybridization of RNA from uninfected HFF cells (lane U), immediate-early times postinfection ("p.i.") (lane IE), early times p.i. (lane E) or late times p.i. (lane L) with the US10 riboprobe AB. The positions of the 28S and 18S rRNAs are shown. The sizes of hybridizing RNAs are given in kb. The transcript originating from the cryptic promoter within the β-glucuronidase gene is indicated with an asterisk (*).

Panel C depicts the hybridization of RNA from uninfected HFF cells (lane U), immediate-early times postinfection ("p.i.") (lane IE), early times p.i. (lane E) or late times p.i. (lane L) with the US11 riboprobe XX. The positions of the 28S and 18S rRNAs are indicated. The sizes of hybridizing RNAs are given in kb. Those transcripts originating from the cryptic promoter within the β-glucuronidase gene are indicated with an asterisk (*).

Panel D depicts a schematic of the US8-US11 region from wild-type strain AD169 of HCMV. Restriction endonuclease sites used for cloning the fragments for riboprobes are shown: ApaI (A), BsmI (B), XbaI (Xb), and XhoI (Xh). The previously mapped wild-type transcripts containing US10-US11 sequences are shown above the schematic. The RNAs expected as a result of the recombination which yields RV131 are shown below the schematic. The shaded box indicates the position and extent of the sequences which are deleted and replaced by the β-glucuronidase gene (not drawn to scale) in RV131-infected cell RNAs. The positions of the HCMV gene-derived riboprobes are indicated.

Figure 6A:
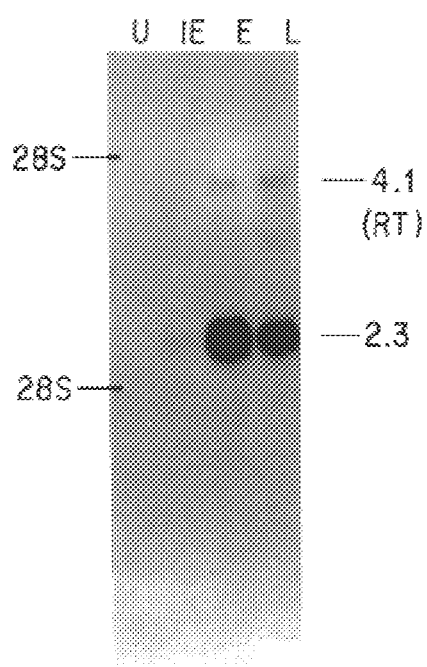
Figure 6B:
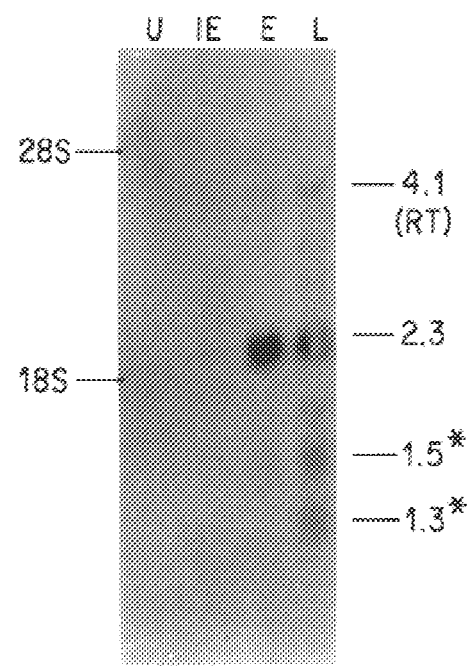
Figure 6C:
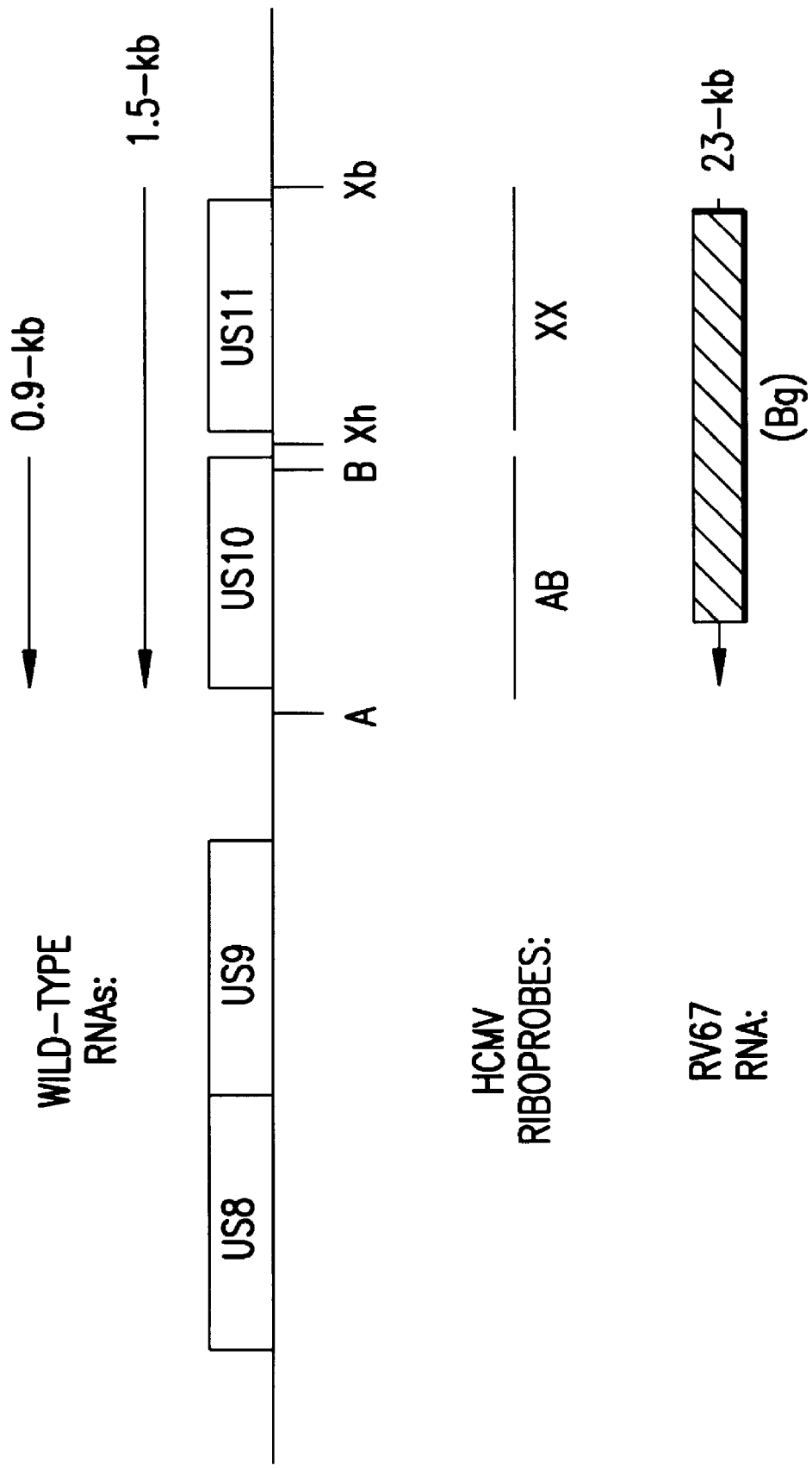

FIGS. 6A–C depicts the Northern blot analysis of RV67-infected cell RNAs.

Panel A depicts the hybridization of RNA from uninfected HFF cells (land U), immediate-early times postinfection ("p.i.") (lane IE), early times p.i. (lane E) or late times p.i. (lane L)with the β-glucuronidase gene riboprobe. The positions of the 28S and 18S rRNAs are shown. The size of hybridizing RNA is given in kb. The βglucuronidase gene-containing read through transcript (RT) is indicated. The transcript originating from the cryptic promoter within the β-glucuronidase gene is indicated with an asterisk (*).

Panel B depicts the hybridization of RNA from uninfected HFF cells (lane U), immediate-early times postinfection ("p.i.") (lane IE), early times p.i. (lane E) or late times p.i. (lane L) with the US10 riboprobe AB. The positions of the 28S and 18S rRNAs are indicated. The size of hybridizing RNA is given in kb. The β-glucuronidase gene-containing read through transcript (RT) is indicated. Those transcripts originating from the cryptic promoter within the β-glucuronidase gene are indicated with an asterisk (*).

Panel C depicts a schematic of the US8-US11 region from wild-type strain AD169 of HCMV. Restriction endonuclease sites used for cloning the fragments for riboprobes are shown: ApaI (A), BsmI (B), XbaI (Xb), and XhoI (Xh). The previously mapped wild-type transcripts containing US10-US11 sequences are shown above the schematic. The message expected as a result of the recombination which yields RV67 is shown below the schematic. The shaded box indicates the position and extent of the sequences which are deleted and replaced by the β-glucuronidase gene (not drawn to scale) in RV67-infected cell RNA. The position of the HCMV gene-derived riboprobes are indicated.

Figure 7A:
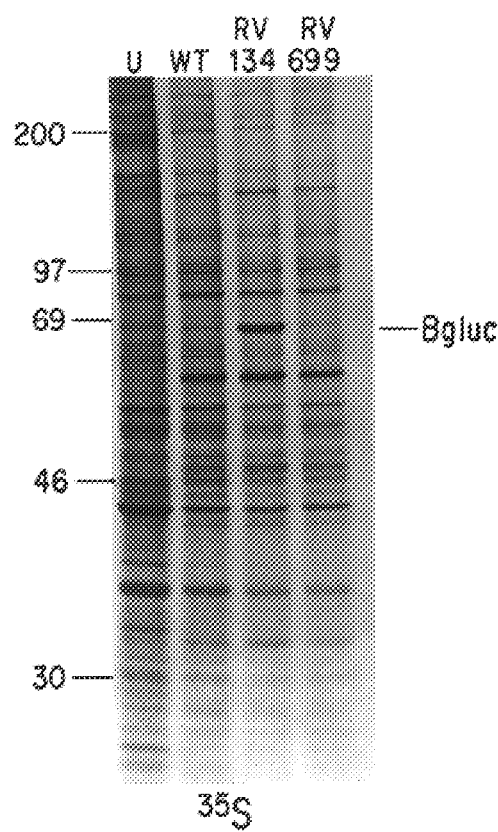
Figure 7B:
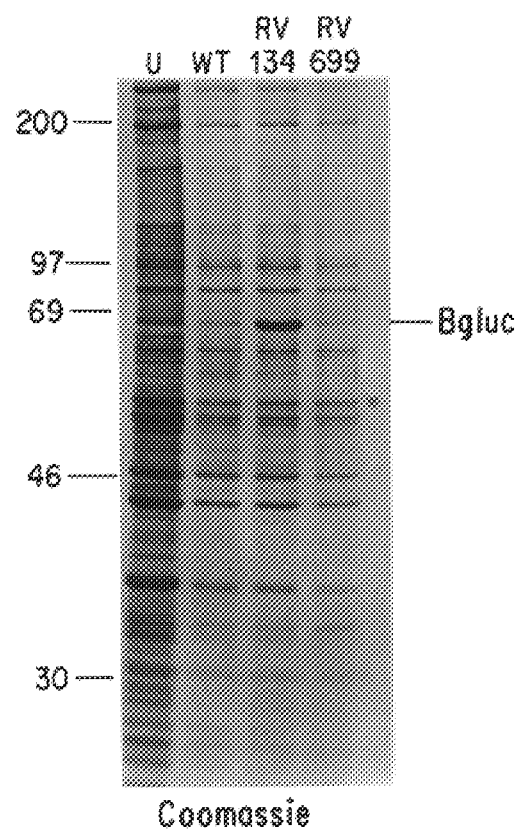

FIGS. 7A–B depicts the total protein analysis of virus infected cells. HFF cells are uninfected (lanes U), or infected at an moi=5 with wild-type strain AD169 (lanes WT), RV134 (lanes RV134), or RV699 (lanes RV699). From 68–72 hours p.i. (or mock infection), proteins are metabolically labelled with $^{35}$S-methionine/cysteine as described below. Cell lysates are electrophoresed in 10% SDS-PAGE and the proteins stained with coomassie blue. The gel is exposed to X-ray film (A) and photographed (B). The position of the 68-kD β-glucuronidase protein is indicated.

Figure 8A:
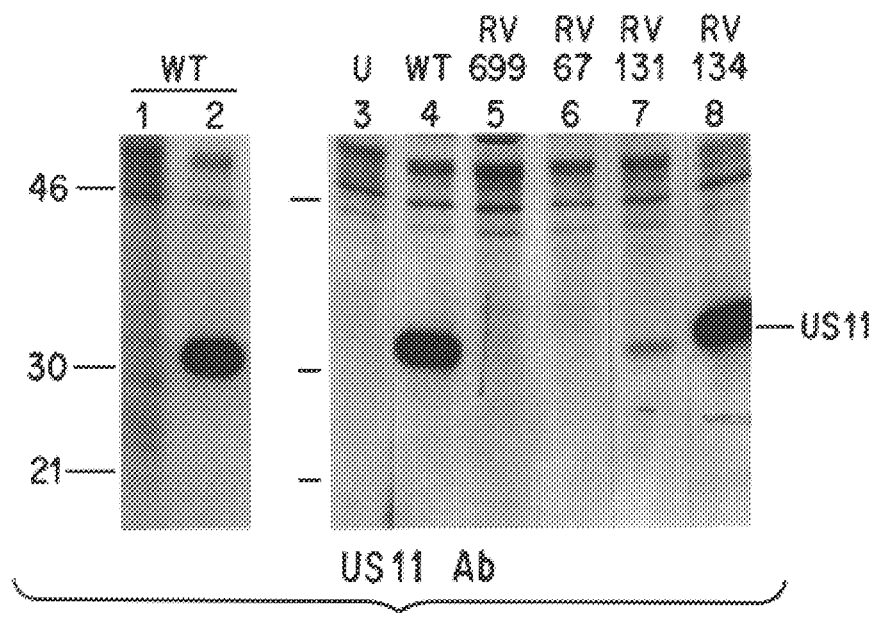
Figure 8B:
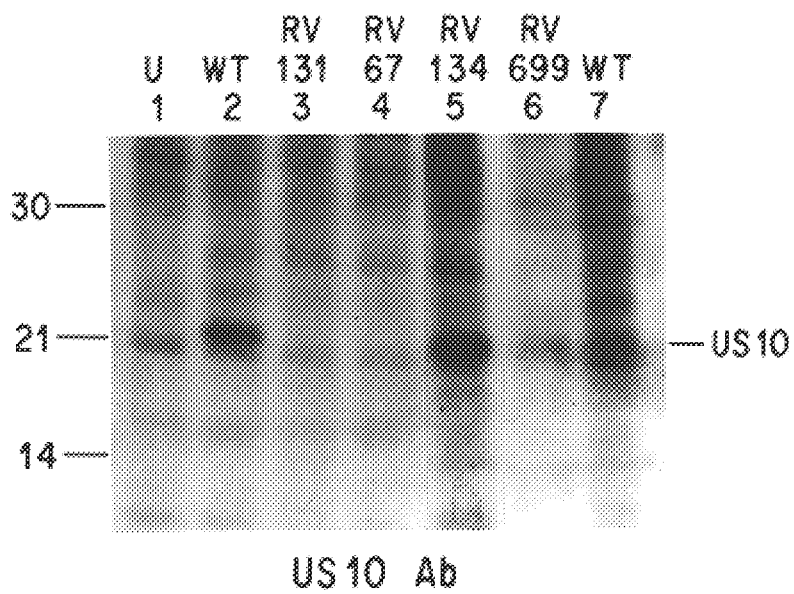

FIGS. 8A–B depicts the immunoprecipitation of US10 and US11 proteins from recombinant virus-infected cell lysates. HFF cells are uninfected (U), or infected at an moi=5 with wild-type strain AD169 (WT), RV134, RV699, RV131, or RV67. From 8–12 hours p.i. (or mock infection), proteins are metabolically labelled with $^{35}$S-methionine/cysteine. Panel A depicts the immuno-precipitation cell lysates using US11 immune antisera (lanes 2–8). Preimmune serum from the same rabbit is used in lane 1. Lanes 1–2 and lanes 3–8 are from different 10% SDS-PAGE gels. Panel B depicts the immunoprecipitation of cell lysates using US10 immune antisera. A 15% SDS-PAGE gel is used. The positions of the Amersham $^{14}$C protein molecular weight markers are indicated to the left of each panel. The positions of the US11 or US10 immuno-precipitated proteins are also indicated.

Figure 9:
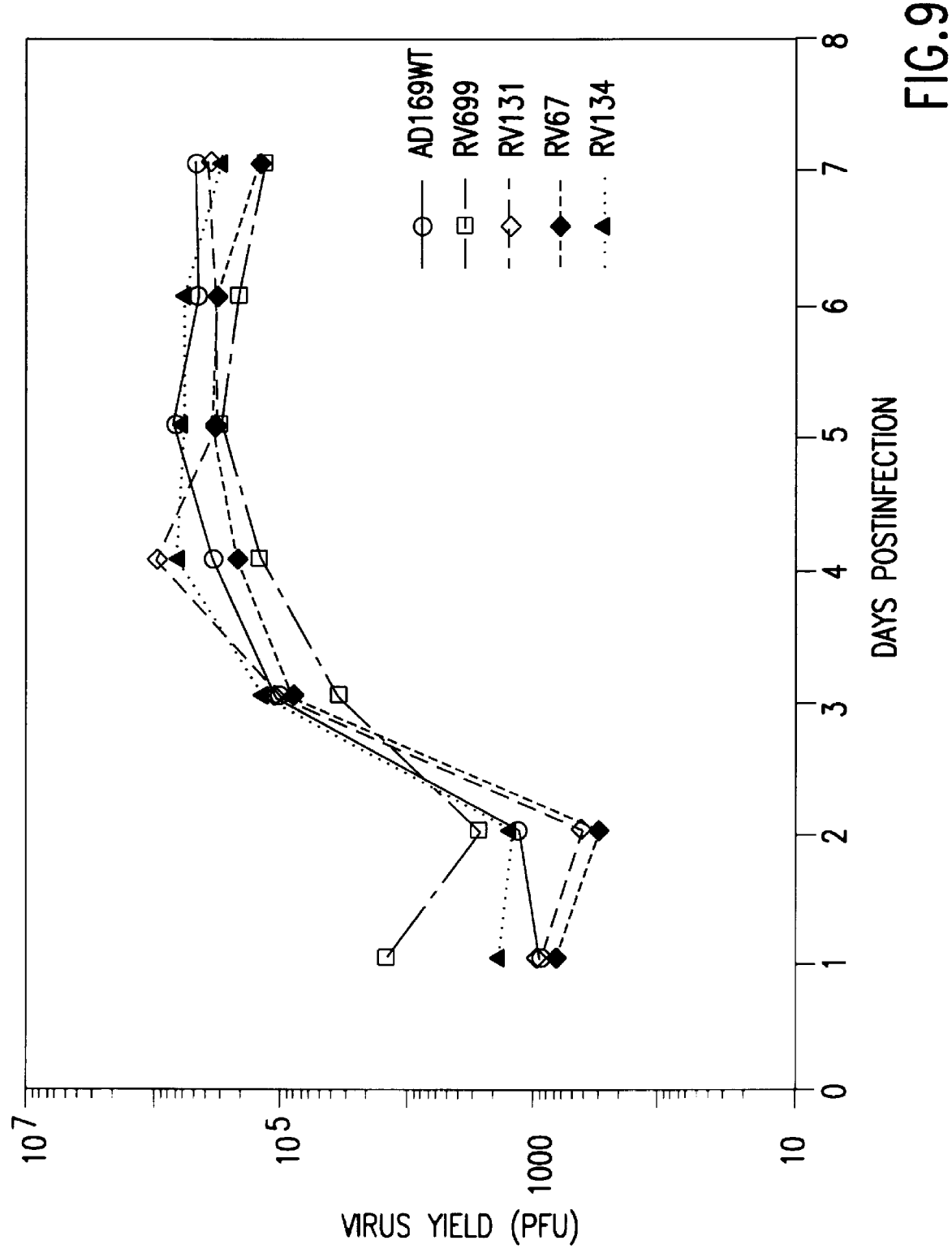

FIG. 9 depicts a one step growth curve of recombinant viruses.

Figure 10A:
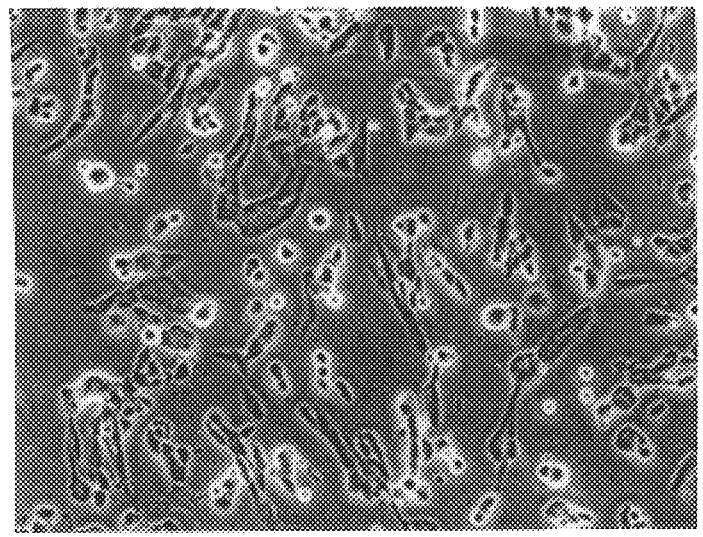
Figure 10B:
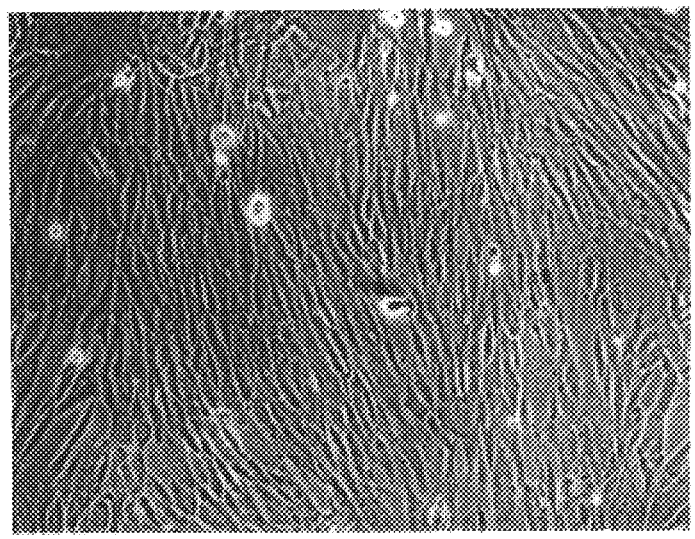
Figure 10C:
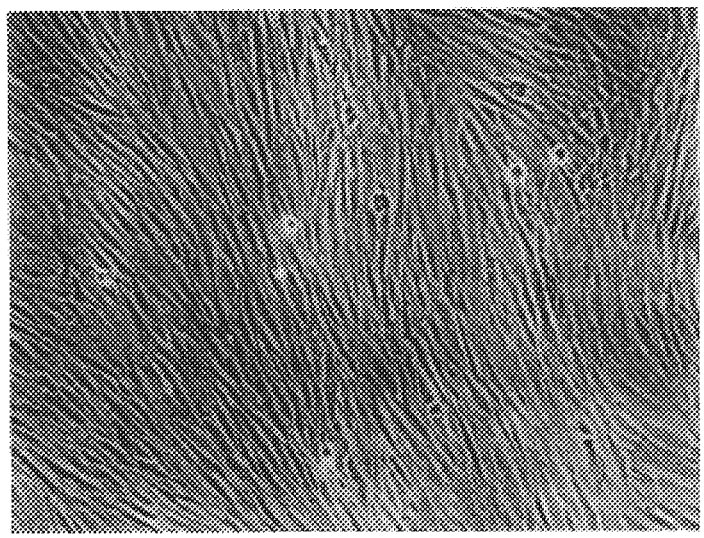
Figure 11C:
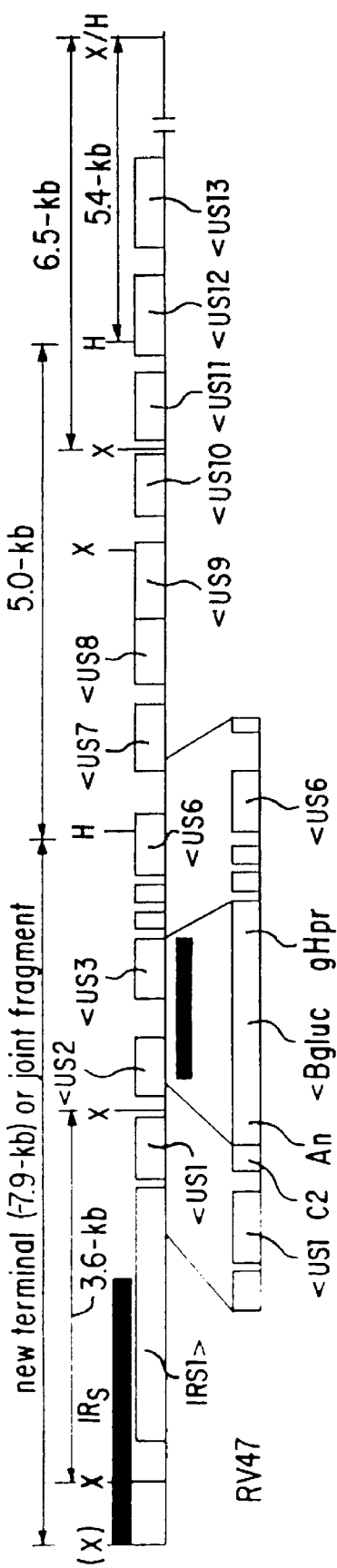
Figure 11D:
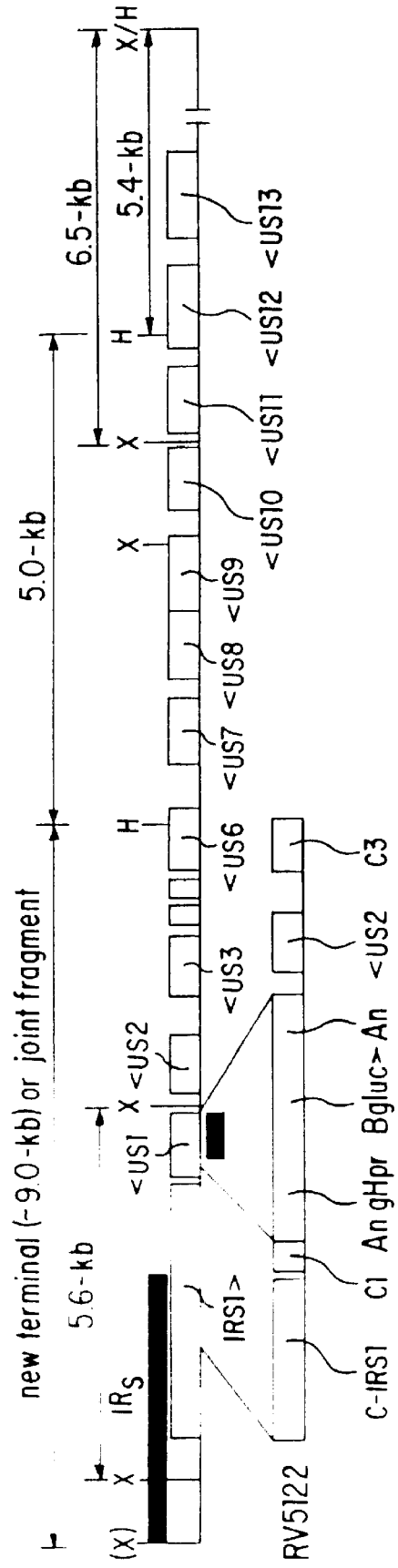
Figure 11E:
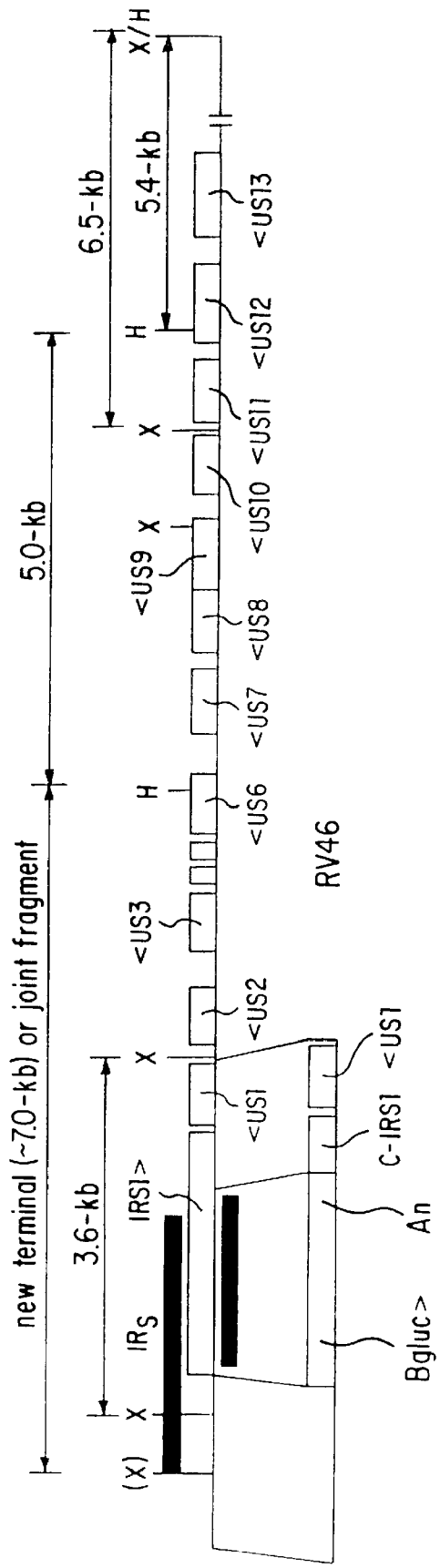

FIG. 10 shows HFF cells 24 hours p.i. at a multiplicity of infection of 2. Panel A depicts the wild-type AD169 strain, showing the rounded phenotype. Panel B depicts the RV670 strain, showing fibroblastoid morphology. Panel C shows uninfected HFF cells for comparison purposes.

FIGS. 11A–E depicts the organization of recombinant virus genomes, depicted in a fashion similar to FIG. 1. In panel A, the first line is a schematic of the overall organization of the HCMV wild-type genome, depicting the location of the HindIII-Q, -X, and -V regions. The second line is an expansion of these regions, with the locations and sizes of HindIII (H) and XhoI (X) restricted enzyme sites. The locations of some hydridization probes used in DNA blot analyses are shown.

Panel B depicts the genomic organization of the RV35 strain. Key restriction enzyme sites and fragment sizes of the recombinant virus genome are indicated. Restriction enzyme sites in parenthesis are deleted as the result of the recombination to yield the mutant virus. The region of the wild-type genome (first line) deleted by recombination to create the mutant is shown by a darkened rectangle. The second line in the panel shows the organization of the relevant region of the linearized plasmid constructed to make the recombinant virus.

Panel C depicts the genomic organization of the RV47 strain. Key restriction enzyme sites and fragment sizes of the recombinant virus genome are indicated. Restriction enzyme sites in parenthesis are deleted as the result of the recombination to yield the mutant virus. The region of the wild-type genome (first line) deleted by recombination to create the mutant is shown by a darkened rectangle. The second line in the panel shows the organization of the relevant region of the linearized plasmid constructed to make the recombinant virus.

Panel D depicts the genomic organization of the RV5122 strain. Key restriction enzyme sites and fragment sizes of the recombinant virus genome are indicated. Restriction enzyme sites in parenthesis are deleted as the result of the recombination to yield the mutant virus. The region of the wild-type genome (first line) deleted by recombination to create the mutant is shown by a darkened rectangle. The second line in the panel shows the organization of the relevant region of the linearized plasmid constructed to make the recombinant virus.

Panel E depicts the genomic organization of the RV46 strain. Key restriction enzyme sites and fragment sizes of the recombinant virus genome are indicated. Restriction enzyme sites in parenthesis are deleted as the result of the recombination to yield the mutant virus. The region of the wild-type genome (first line) deleted by recombination to create the mutant is shown by a darkened rectangle. The second line in the panel shows the organization of the relevant region of the linearized plasmid constructed to make the recombinant virus.

Figure 12A:
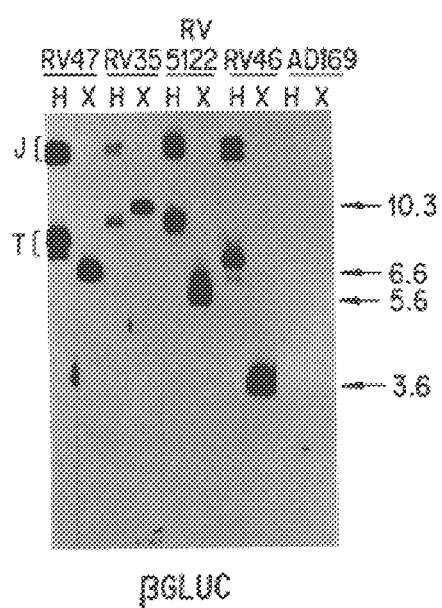
Figure 12B:
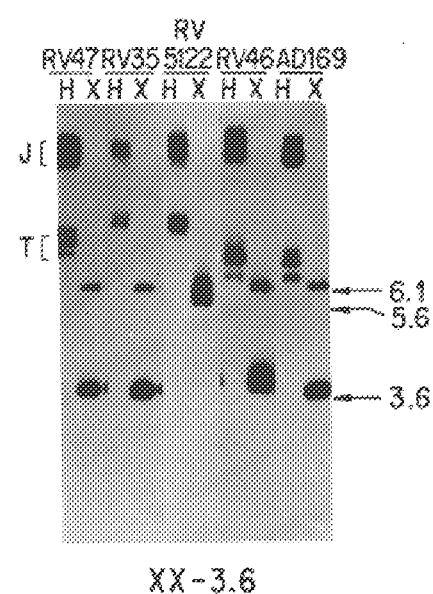
Figure 12C:
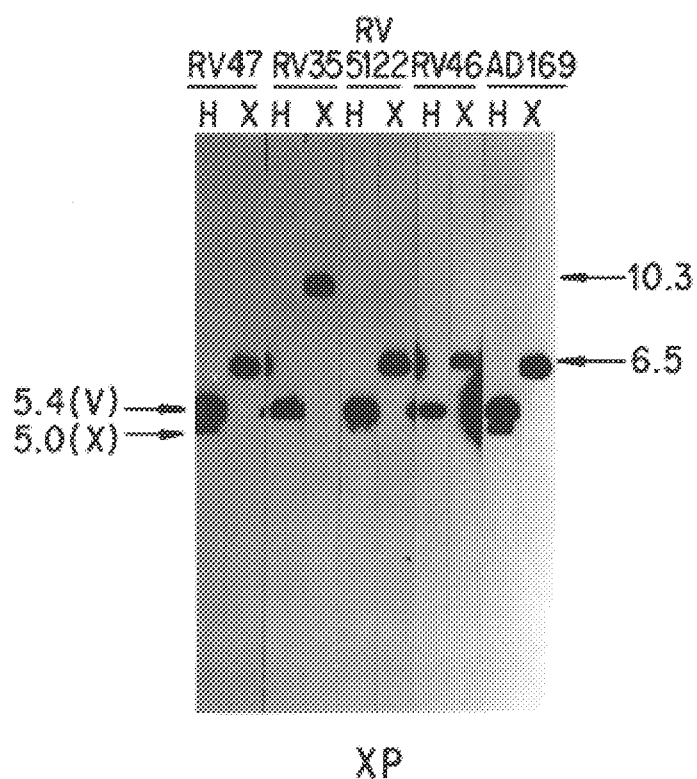

FIGS. 12A–C is the blot analysis of the HCMV recombinant mutant genomic DNA.

Panel A depicts the HCMV wild-type strain AD169 or the indicated recombinant virus (RV) DNA which is digested with HindIII (lanes H) or XhoI (lanes X), electrophoresed, blotted and hybridized with a β-glucuronidase probe. The positions of joint (J) or terminal (T) region fragments or the sizes of fragments hybridizing in HindIII digests are indicated to the left of each panel. The sizes of fragments hybridizing in XhoI digests are indicated to the right.

Panel B depicts the HCMV wild-type strain AD169 or the indicated recombinant virus (RV) DNA which is digested with HindIII (lanes H) or XhoI (lanes X), electrophoresed, blotted and hybridized with the XX-3.6 probe. The positions of joint (J) or terminal (T) region fragments or the sizes of fragments hybridizing in HindIII digests are indicated to the left of each panel. The sizes of fragments hybridizing in XhoI digests are indicated to the right.

Panel C depicts the HCMV wild-type strain AD169 or the indicated recombinant virus (RV) DNA which is digested with HindIII (lanes H) or XhoI (lanes X), electrophoresed, blotted and hybridized with the XP probe. The positions of joint (J) or terminal (T) region fragments or the sizes of fragments hybridizing in HindIII digests are indicated to the left of each panel; the sizes of fragments hybridizing in XhoI digests are indicated to the right. Hybridization of the XP probe to the same terminal and joint region DNA fragments of RV35 as hybridized with the β-glucuronidase and XX-3.6 probes is clearly detected upon longer exposure of the autoradiogram of panel C.

FIGS. 13A–F shows HFF cells at a multiplicity of infection. The photographs are taken at 24 hours p.i. Panel A depicts the HFF cells infected with the RV5122 strain with a multiplicity of infection of 2. Panel B depicts the HFF cells infected with the RV47 strain at a multiplicity of depicts the HFF cells Panel C depicts the HFF cells infected with the RV35 strain with a multiplicity of infection of 2. Panel D depicts the HFF cells infected with the RV46 strain at a multiplicity of infection of 2. Panel E depicts the HFF cells infected with the RV46 strain at a multiplicity of infection of 10. Panel F depicts the HFF cells infected with the wild-type strain AD169 at a multiplicity of infection of 10.

FIGS. 14A–E is blot analysis of cytoplasmic RNA from wild-type HCMV-infected cells.

Panel A depicts the blot analysis employing a riboprobe specific for the unique region sequences of IRS1. Total cytoplasmic RNA from uninfected cells (U), cells under immediate-early conditions (IE), cells under early conditions (E) and cells under late conditions (L) is used. The approximate size of hybridizing RNAs are given in kb. The locations of 28S and 18S rRNA are also indicated.

Panel B depicts the blot analysis employing a riboprobe specific for US1 sequences. Total cytoplasmic RNA from uninfected cells (U), cells under immediate-early conditions (IE), cells under early conditions (E) and cells under late conditions (L) is used. The approximate size of hybridizing RNAs are given in kb. The locations of 28S and 18S rRNA are also indicated.

Panel C depicts the blot analysis employing a riboprobe specific for US2 sequences. Total cytoplasmic RNA from uninfected cells (U), cells under immediate-early conditions (IE), cells under early conditions (E) and cells under late conditions (L) is used. The approximate size of hybridizing RNAs are given in kb. The locations of 28S and 18S rRNA are also indicated.

Panel D depicts the blot analysis employing a riboprobe specific for the unique region sequences of IRS1. Total cytoplasmic RNA from uninfected cells (U) or from cells at the indicated hours p.i. is used. The approximate size of hybridizing RNAs are given in kb. The locations of 28S and 18S rRNA are also indicated.

Panel E depicts the blot analysis employing a riboprobe specific for the unique region sequences of IRS1. Total cytoplasmic RNA from uninfected cells (U) or from cells at the indicated hours p.i. is used. The approximate size of hybridizing RNAs are given in kb. The locations of 28S and 18S rRNA are also indicated. The approximate size of hybridizing RNAs are given in kb. The locations of 28S and 18S rRNA are also indicated.

Figure 15A:
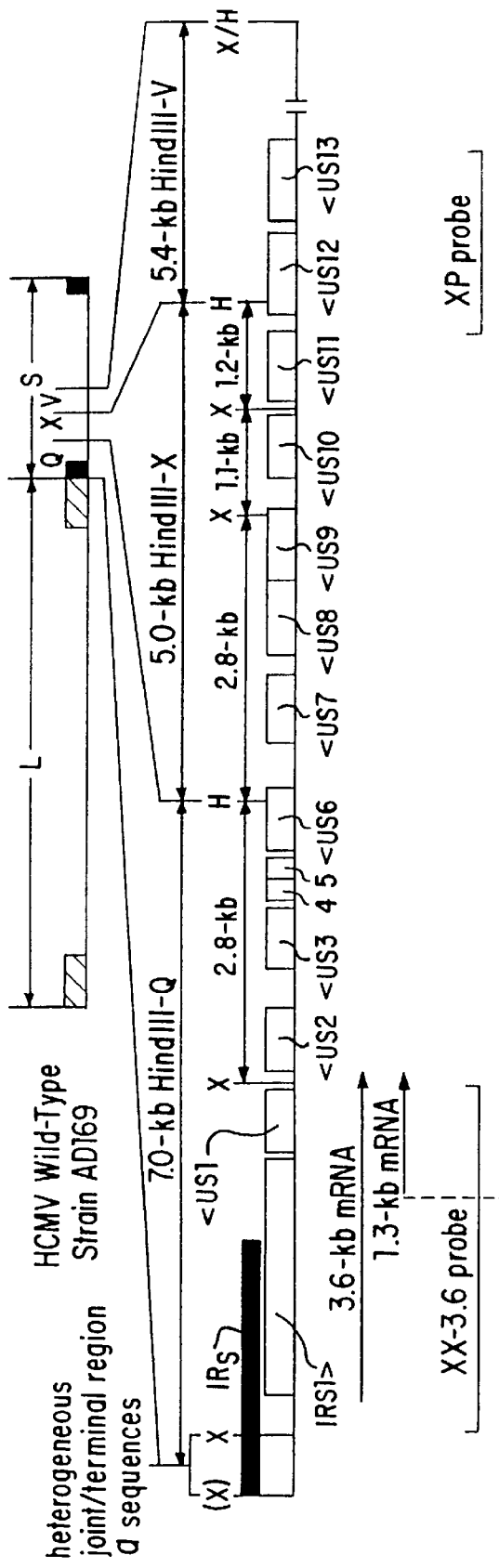
Figure 15B:
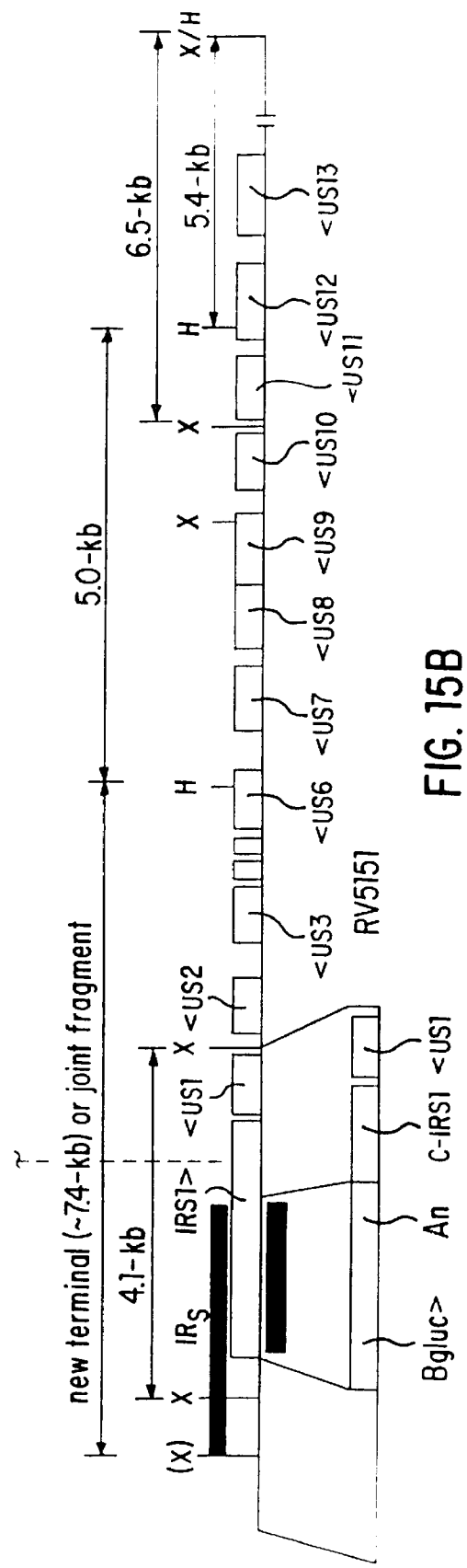

FIGS. 15A–B depicts the organization of the recombinant mutant RV5151 genome. Panel A and panel B are analogous to those described in FIG. 11.

Figure 16:
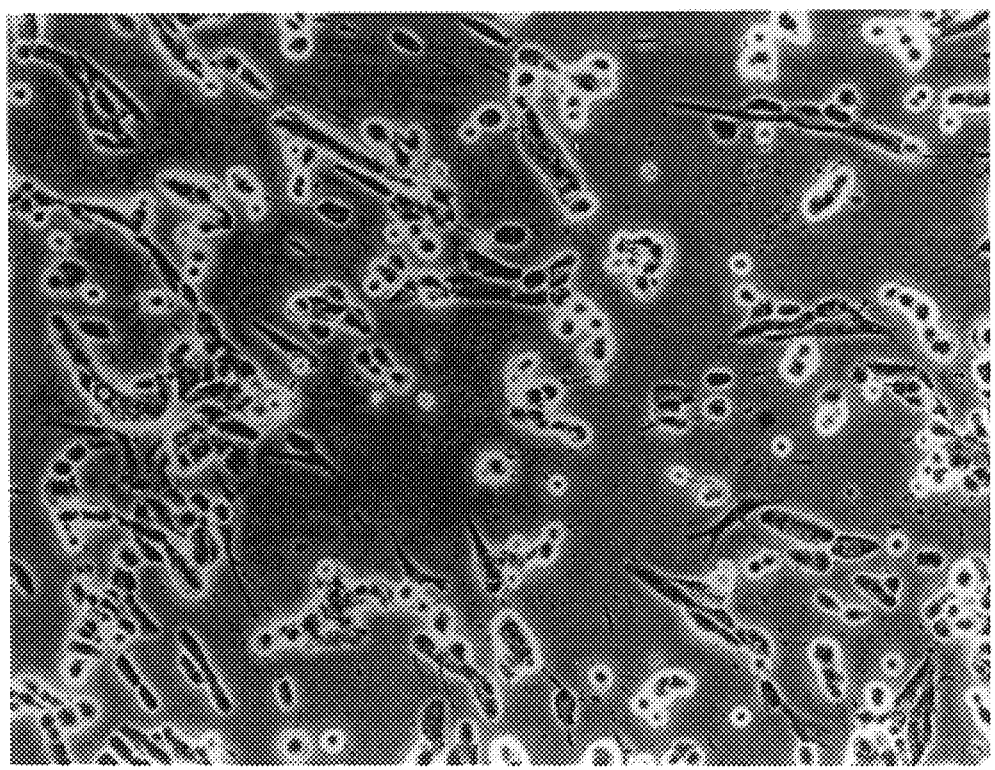

FIG. 16 shows HFF cells infected with RV5151 at a multiplicity of infection of 2. The photograph is taken at 24 hours p.i.

DETAILED DESCRIPTION OF THE INVENTION

This invention involves the insertion of a β-glucuronidase marker gene (an expression cassette) into the genome of HCMV. The recombinants constructed by this site-directed mutagenesis are stable, i.e., the recombinant virus genomes are stable upon passage in tissue culture at low multiplicity of infection. The β-glucuronidase is inserted by either replacing a portion of a wild-type HCMV gene or as an addition to the wild-type gene (so as to disrupt the wild-type gene). Both the replacement or addition techniques prevent the expression in the recombinant virus of the wild-type product of the wild-type HCMV gene. The replacement technique also comprises the insertion of the β-glucuronidase gene so as to replace portions of two or more genes. The insertion can be made in the various regions of the HCMV genome, such as the US and UL regions, as well as in the repeat regions bounding US and UL.

The recombinants containing the inserted β-glucuronidase gene are used in two embodiments of this invention: First, expression of the gene carrying the insertion and replication of the recombinant virus are monitored. The insertion prevents the expression of the wild-type product of the native gene. Therefore, if the virus replicates, the gene is identified as non-essential for viral survival and growth, that is, replication. Repeated use of this technique serves to narrow the range of HCMV genes which may be essential to viral replication. Identification of such essential gene or genes will facilitate rational drug design of compounds active against HCMV. In accordance with the above, this invention provides a method for determining whether a gene is non-essential for wild-type human cytomegalovirus (HCMV) replication. This method comprises inserting a β-glucuronidase marker gene into the wild-type HCMV genome to prevent expression of the gene, thereby creating a recombinant HCMV genome, introducing the recombinant HCMV genome into a suitable host cell, growing the host cell under suitable conditions such that HCMV viral replication can occur, screening the host cell for the presence of progeny virus, the presence of progeny virus indicating that the gene is non-essential for the wild-type HCMV genome or replication. Methods of "inserting" a marker gene into a nucleic acid sequence are well known to those of skill in the art and comprise various molecular cloning techniques. As used herein, the term "introducing" encompasses any method of inserting an exogenous nucleic acid molecule into a cell and includes, but is not limited to: transformation; transfection; microinjection; and viral infection of host cells.

This method will assist in the identification of complexes of two or more gene products of HCMV, which are complexes of HCMV virion membrane glycoproteins. In turn, information about the constituents of the complex will facilitate development of vaccines against HCMV.

In one embodiment, the recombinant constructs are generated by introducing genomic HCMV DNA with a linearized plasmid containing the β-glucuronidase marker gene whose expression is controlled by either the endogenous promoter or a heterologous promoter (to increase the level of expression). It is also useful to include an HSV thymidine kinase (tk) polyadenylation signal (to terminate transcription).

The fidelity of the DNA insertions into the HCMV is analyzed by Southern blot hybridization of viral DNA. Northern blot analysis is conducted using RNA from human foreskin fibroblast cells infected with recombinant HCMV strains and the positions of the RNA hybridizing with riboprobes are determined. Analysis of expression of HCMV gene products from recombinant virus-infected fibroblast cell lysates is conducted by immunoprecipitation using polyclonal antisera. The effect of the promoter on levels of β-glucuronidase is determined by SDS-PAGE of total protein extracts of recombinant virus-infected fibroblast cells. Growth curve studies of recombinant viruses indicate whether a non-essential HCMV gene is beneficial to the proliferation of the virus in human fibroblasts. If a gene is determined to be beneficial, it may be used to facilitate rational drug design of compounds against HCMV.

The second embodiment of this invention utilizes the marker-expressing HCMV recombinant in an assay method for screening for inhibitors of HCMV. The second embodiment also utilizes recombinants in which the β-glucuronidase gene expression cassette is inserted in an intergenic region between two HCMV genes, such that no HCMV genes are replaced or disrupted and all HCMV gene products are expressed. Thus, this embodiment is a method for identifying a compound which inhibits HCMV replication. This method comprises inserting a β-glucuronidase marker gene into the HCMV genome to construct an HCMV recombinant in a manner selected from the group consisting of: replacing a portion of wild-type HCMV gene, such that the insertion of the marker gene prevents the expression of the product of the wild-type gene; adding to wild-type HCMV gene, so as to disrupt the wild-type gene, such that the insertion of the marker gene prevents the expression of the product of the wild-type gene; replacing portions of two or more wild-type HCMV genes, such that the insertion of the β-glucuronidase marker gene prevents the expression of the products of the wild-type genes; and inserting the β-glucuronidase marker gene between two HCMV genes, such that no HCMV genes are replaced or disrupted and all HCMV gene products are expressed. The recombinant HCMV is then inserted into a suitable host cell, and the host cell is grown under suitable conditions to favor HCMV replication, the amount of any β-glucuronidase produced is then measured. These steps are repeated in the presence of the test compound and the results are compared, a reduction or inhibition of the amount of β-glucuronidase produced in the presence of the test compound indicating that the test compound inhibits HCMV replication.

In one aspect of the second embodiment of this invention, the HCMV recombinant express β-glucuronidase which is able to cleave a conjugated chemical substrate to release a fluorescing product. If a test compound screened inhibits an essential or beneficial HCMV function, the level of expression of β-glucuronidase expression is reduced. Reduction of β-glucuronidase levels results in a reduction in the cleavage of the conjugated substrate. Reduction in cleavage yields reduced levels of fluorescing product, indicating that the test compound is an inhibitor of HCMV.

In an alternate aspect of the second embodiment of this invention, the β-glucuronidase expressed by the HCMV recombinant cleaves a conjugated chemical substrate to release a chromophoric product which undergoes a color change upon cleavage. If a test compound is inhibitory, the level of cleavage of the conjugate is reduced, which reduces the extent of the color change. The color change is monitored visually or spectrophotometrically.

As mentioned above, the only marker-expressing HCMV recombinant virus reported to date (12) contained β-galactosidase within a repeat (i.e. diploid) sequence region bounding UL. In order to study HCMV gene function by the genetic approach of site-directed insertion/replacement mutagenesis, a small marker gene, β-glucuronidase, is investigated for its utility in HCMV. β-glucuronidase has been reported to be appropriate for use as a marker in plant, nematode, and insect (baculovirus) systems (13, 19, 20). The use of β-glucuronidase as a marker gene in mammalian or animal virus systems has not been reported. It has been thought that endogenous cellular β-glucuronidase in mammalian cells (21) would eliminate the usefulness of this gene as a marker.

In contrast, β-galactosidase has been used in many systems (including with HSV). However, in the one reported use of β-galactosidase, this HCMV recombinant (RC256) contained a deletion adjacent to the site of β-galactosidase insertion (23). One hypothesis that the authors proposed was that the deletion occurred due to the large size of the β-galactosidase insert coupled with the DNA size packaging limits of the HCMV viral capsid. Another characteristic of the β-galactosidase-expressing HCMV recombinant RC256 is that it is very unstable (12).

HCMV is permissive in very few cell types in tissue culture (including human foreskin fibroblast (HFF) cells) and infection by this virus stimulates the expression of some cellular genes. It is determined that both uninfected and wild-type HCMV infected type HFF cells express very little endogenous cellular β-glucuronidase.

Since there have not been any published reports of non-essential genes in the HCMV system, the strategy to test whether β-glucuronidase could serve as a marker in this system is to design a plasmid that would direct β-glucuronidase recombination into the US10-US9 intergenic region. Transcripts expressed from the HCMV US6 gene family have been mapped (17). Only low abundance read-through RNAs are transcribed from an intergenic region between US10 and US9.

According to this invention, the utility of the prokaryotic β-glucuronidase marker gene to identify recombinant HCMV is demonstrated. β-glucuronidase is preferable to β-galactosidase as a marker gene in the HCMV system because of its relatively small size (1.9-kb versus 3.1-kb). Like β-galactosidase, functional β-glucuronidase is likely tetrameric, consisting of identical monomeric 68-kd subunits, and is very stable (19). All types of chromogenic substrates (yielding either soluble, insoluble, or fluorescent products upon enzymatic cleavage) which are available for β-galactosidase are also available for β-glucuronidase. Applicants have constructed (in a site-directed fashion), isolated and characterized a multiplicity of recombinant HCMV which contain and express the prokaryotic β-glucuronidase gene. All of the isolated β-glucuronidase-expressing HCMV recombinant appear to be genetically stable.

Utilizing the method of this invention, the IRS1 gene of HCMV is specifically identified as a gene required for early cytopathic effect ("CPE") of HCMV-infected cells. At early times p.i. of permissive cells by HCMV, morphological changes occur in which the cells display a round phenotype which has been termed early CPE (33, 37). The rounding begins at about six (6) hours p.i. ("p.i.") and is most apparent from approximately twelve (12) to twenty-four (24) hours p.i. At this time, the infected cells appear very contracted, instead of the typical fibroblastoid morphology. After twenty-four (24) hours p.i., cell relaxation begins and by 48 to 72 hours p.i., the infected cells display an enlarged cytomegalic fibroblastoid morphology.

IRS1 gene function is identified by examination of the phenotype of mutant RV670. Examination reveals that RV670 is a construct with an unexpected extensive deletion of a cluster of viral genes. It is deleted of nine major open reading frames (called IRS1, US1-US3, US6-US9, and US11). In contrast, mutant RV35 (described in more detail herein) which is a mutant deleted of the U6 family only, (i.e., US6 to US11, inclusive) still induces the morphological change. To determine which of the four remaining genes is required for the morphological change, mutants lacking these genes are made. Mutants deleted of the open reading frames US1 to US3 retain the ability to induce the phenotype, while a mutant deleted of IRS1 lost this ability.

Results of RNA blot analysis provides support for the conclusion that IRS1 is responsible for early CPE since it is transcribed coincidently with the appearance of the contracted phenotype. Two mRNAs are transcribed from the IRS1 gene, a 3.6-kb message which is present at early and late times p.i. and a 1.3-kb transcript detected most abundantly at early times and thus, is believed to be the gene product responsible for early rounding.

Thus, a nucleic acid sequence encoding the protein product which induces early rounding in HCMV cells is also provided by this invention. This nucleic acid sequence is the DNA sequence designated IRS1. In addition, for the purposes of this invention, the nucleic acid molecule may be DNA, cDNA or RNA. However, in the most preferred embodiment of this invention, the nucleic acid is a cDNA molecule.

This invention also encompasses each of the nucleic acid molecules described hereinabove inserted into a vector so that the nucleic acid molecule may be expressed, i.e., transcribed (when the molecule is DNA) and translated into a polypeptide in both procaryotic and eucaryotic expression systems. Suitable expression vectors useful for the practice of this invention include pET3a (46), pMal-c2 (New England Biolabs), pSE420 (Invitrogen), pVL1392 (Invitrogen), pYES2 (Invitrogen), pCDNA1 (Invitrogen), pSG5 (Stratagene), and pCEP420 (Invitrogen). However, in the preferred embodiment of this invention, the vector pCDNA1 is the expression vector for expression in eucaryotic cells. As is well known to those of skill in the art, the nucleic acid molecules of this invention may be operatively linked to a promoter of RNA transcription, as well as other regulatory sequences. As used herein, the term "operatively linked" means positioned in such a manner that the promoter will direct the transcription of RNA off of the nucleic acid molecule, An example of a promoter is HCMV major immediate-early promoter. The vectors of this invention preferably are capable of transcribing and/or translating nucleic acid in vitro or in vivo. The recombinant polypeptide produced from the expression of the nucleic acid molecules of this invention are also provided.

A host vector system for the production of the recombinant polypeptide described hereinabove and for expressing the nucleic acid molecules of the subject invention are provided. The host vector system comprises one of the vectors described hereinabove in a suitable host. For the purpose of the invention, a suitable host may include, but is not limited to a eucaryotic cell, e.g., a mammalian cell, a yeast cell or an insect cell for baculovirus expression. Suitable mammalian cells may comprise, but are not limited to COS cells. Suitable procaryotic cells may include, but are not limited to bacteria cells, HB101 (Invitrogen), and BL21 (DE3)LYsS (43). Accordingly, the procaryotic or eucaryotic cell comprising any of these vector systems is further provided by this invention.

As is known to those of skill in the art, recombinant DNA technology involves insertion of specific DNA sequences into a DNA vehicle (vector) to form a recombinant DNA molecule which is capable of being replicated in a host cell. Generally, but not necessarily, the inserted DNA sequence is foreign to the recipient DNA vehicle, i.e., the inserted DNA sequence and DNA vector are derived from organisms which do not exchange genetic information in nature, or the inserted DNA sequence comprises information which may be wholly or partially artificial. Several general methods have been developed which enable construction of recombinant DNA molecules. For example, U.S. Pat. No. 4,237,224 to Cohen and 1Boyer describes production of such recombinant plasmids using processes of cleavage of DNA with restriction enzymes and joining the DNA pieces by known method of ligation.

These recombinant plasmids are then introduced by means of transformation or transfection and replicated in unicellular cultures including procaryotic organisms and eucaryotic organisms and eucaryotic cells grown in tissue culture. Because of the general applicability of the techniques described therein, U.S. Pat. No. 4,237,224 is hereby incorporated by reference into the present specification. Another method for introducing recombinant DNA molecules into unicellular organisms is described by Collins and Hohn in U.S. Patent No. 4,304,863 which is also incorporated herein by reference. This method utilized a packaging transduction system with bacteriophage vectors (cosmids).

Nucleic acid sequences may also be inserted into viruses, for example, a vaccinia virus or a baculovirus. Such recombinant viruses may be generated, for example, by transfection of plasmids into cells infected with virus, Chakrabarti et al, (1985) Mol. Cell Biol. 5:3402–3409.

In addition, if all of the proper replication, transcription and translation signals are correctly arranged on the recombinant DNA molecule, the foreign gene will be properly expressed in the transformed or transfected host cells.

Different genetic signals and processing events control gene expression at different levels. For instance, DNA transcription is one level, and messenger RNA (mRNA) translation is another. Transcription of DNA is dependent upon the presence of a promoter which is a DNA sequence that directs the binding of RNA polymerase and thereby promotes RNA synthesis. The DNA sequences of eucaryotic promoter differ from those of procaryotic promoters. Furthermore, eucaryotic promoters and accompanying genetic signals may not be recognized in or may not function in a procaryotic system.

Successful expression of a cloned gene requires efficient transcription of DNA, translation of the mRNA and in some instances post-translation modification of the protein. Expression vectors have been developed to increase protein production from the cloned gene. In expression vectors, the cloned gene is often placed next to a strong promoter which is controllable so that transcription can be turned on when necessary. Cells can be grown to a high density and then the promoter can be induced to increase the number of transcripts. These, if efficiency translated, will result in high yields of polypeptide. This is an especially valuable system if the foreign protein is deleterious to the host cell.

A method for producing a recombinant polypeptide described hereinabove, is also provided. This method comprises growing the host cell containing the nucleic acid of this invention and/or the host vector system of this invention under suitable conditions, permitting production of the polypeptide and recovering the resulting recombinant polypeptide produced.

A method of detecting in a sample the presence of the nucleic acid encoding the early CPE-associated protein is further provided by this invention. This method comprises isolating the DNA or RNA of an infected cell and contacting the isolated nucleic acid with labeled IRS1 cDNA under suitable hybridization conditions such that DNA-cDNA or cDNA-RNA complexes are formed with the labeled IRS1 DNA, and detecting the presence of any complex so formed, the presence of complex being a positive indication that the cell has or is expressing this gene. Those of skill in the art will recognize this method as Southern and Northern hybridization (see 53).

The β-glucuronidase marker-expressing recombinant HCMVs used in the two embodiments of this invention are constructed as follows: HCMV strain AD169, which contains native genomic (wild-type) DNA, is obtained from the American Type Culture Collection (ATCC VR538) and is subjected to restriction endonuclease digestion to obtain DNA fragments. Plasmids are constructed which contain DNA for the desired HCMV gene or genes (that is, DNA flanking the site of the intended insertion), the desired gene's promoter or another HCMV promoter (such as the 2.7E promoter), the gene encoding β-glucuronidase and, optionally, an HSV-1 tk polyadenylation signal fragment.

Details of the construction of a number of plasmids are presented in Examples 1 and 8. Other plasmids are constructed using the techniques described herein.

Each plasmid is linearized at a unique restriction site and co-transfected with infectious HCMV wild-type DNA into HFF cells. Screening for β-glucuronidase-expressing recombinant HCMV mutants is conducted by plating on cells, such as HFF cells. The infected cells are overlayed with medium containing a chromogenic substrate of β-glucuronidase. Plaques which appear blue, the color of the enzymatically cleaved substrate, contain the recombinant marker-expressing virus. Plaque purification is performed to obtain the recombinant virus.

Using the foregoing procedures, recombinant viruses are constructed in which portions of one or more HCMV genes are replaced with the β-glucuronidase gene or in which the β-glucuronidase gene is inserted so as to disrupt an HCMV gene. Both types of constructs will be unable to express the wild-type gene product of such a replaced or disrupted gene. Both types of constructs are used to screen for non-essential HCMV genes and can be used to screen for inhibitors of HCMV. Examples of recombinant HCMVs (described in Example 1) in which one gene is replaced include RV699, RV131, RV145, RV725, RV69 and RV92. Examples of recombinant HCMVs in which two or more genes are replaced include RV67, RV80, RV101 and RV670. Examples of recombinant HCMVs in which a gene is disrupted include RV102, RV88 and RV91.

In addition, the β-glucuronidase gene can be inserted between two HCMV genes, so as to not hinder expression of those two gene products. Such a construct is suitable for use in screening for inhibitors of HCMV. An example of a recombinant HCMV containing an intergenic insertion is RV134.

Table 1 presents a summary of the foregoing enumerated HCMV recombinant viruses:

TABLE 1

| Virus | ORF(s) Replaced/Disrupted | Comment |
| --- | --- | --- |
| RV134 | none | A |
| RV699 | US11 | B |
| RV131, RV145 | US10 | B |
| RV67 | US11 and US10 | B |
| RV80 | US9 and US8 | B |
| RV725 | US7 | B |
| RV69 | US6 | B |
| RV102 | US13 | C |
| RV88 | US12 | C |
| RV91 | US27 | D |
| RV92 | US28 | D |
| RV101 | US27 and US28 | D |
| RV670 RV35 | US11, US9-US1 and IRS1 | B,E |

A: RV134 contains an insertion within the intergenic region between US10 and US9.
B: HCMV ORFs US6 through US11 are members of the US6 family of potential membrane glycoprotein genes (25,27,38).
C: HCMV ORFs US12 and US13 encode proteins with multiple membrane-spanning domains which may be found in membranes (25).
D: HCMV ORFs US27 and US28 encode proteins with seven putative membrane-spanning domains which are homologues of known G-protein coupled receptors (3).
E: HCMV ORF IRS1 is partially homologous to TRS1 (3), which is not deleted in RV670; ORF IRS1 is related to ORFs US221 US23, US24 and US25 (3); ORF US1 is related to US31 and US32 (25); ORFs US2 and US3 may encode membrane glycoproteins (3).

Samples of RV145 were deposited with the American Type Culture Collection, 13201 Parklawn Drive, Rockville, Md. 20852, and were assigned ATCC accession number VR 2329. RV145 contains the same gene replacement as RV131, but is preferred for use in the screen for HCMV inhibitors because of the higher levels of expression of β-glucuronidase provided by the heterologous 2.7E promoter in RV145. By utilizing the information provided in Example 1, the other recombinant HCMVs of Example 1 can be constructed by persons skilled in the art.

Figure 2A:
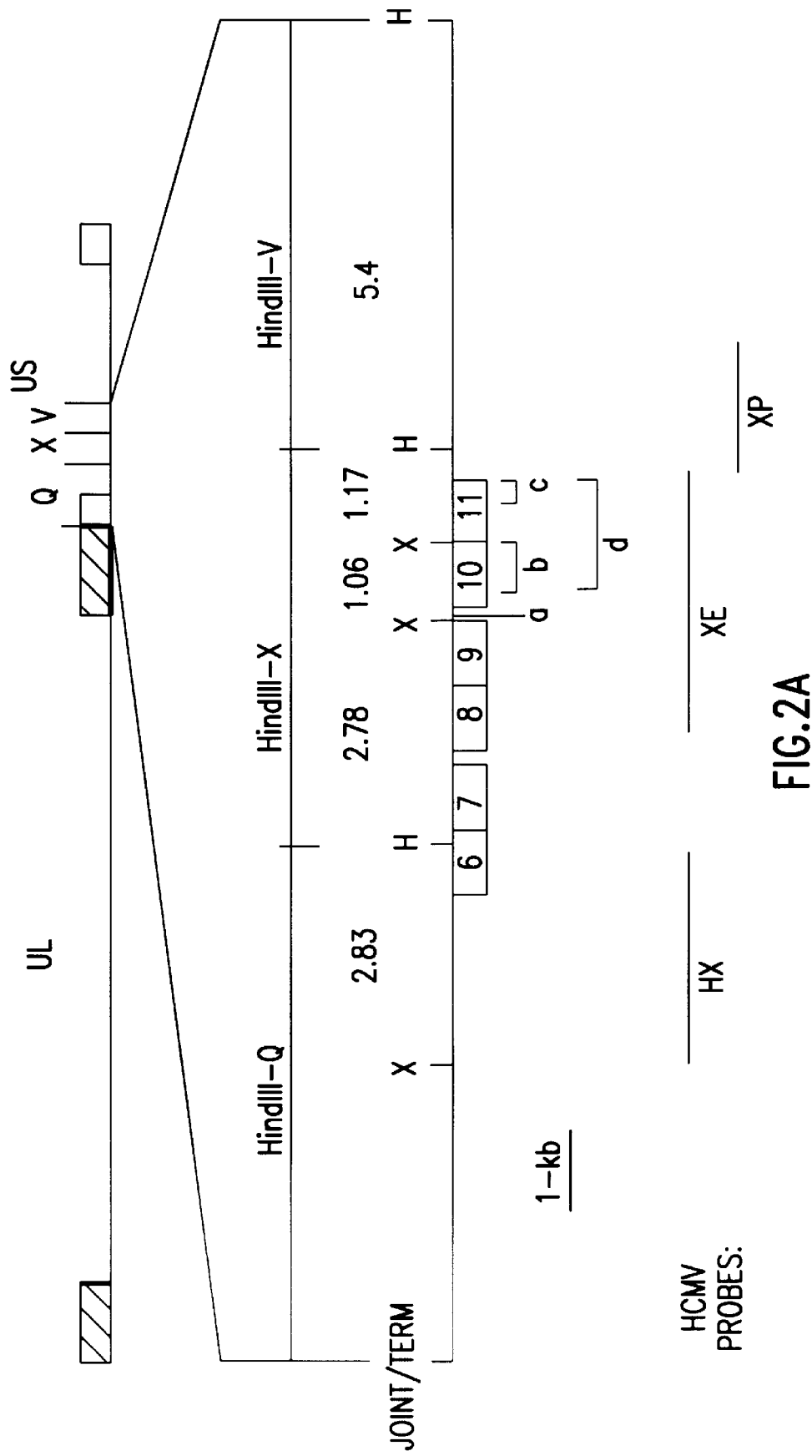
Figure 2B:
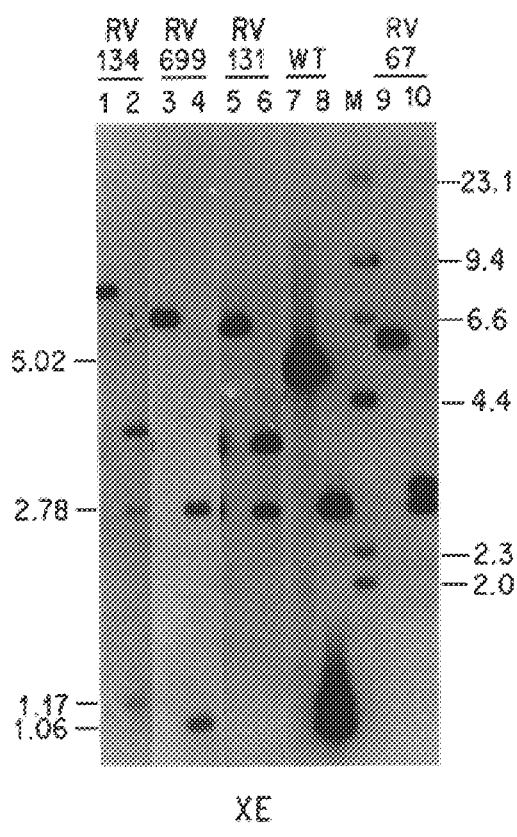
Figure 2C:
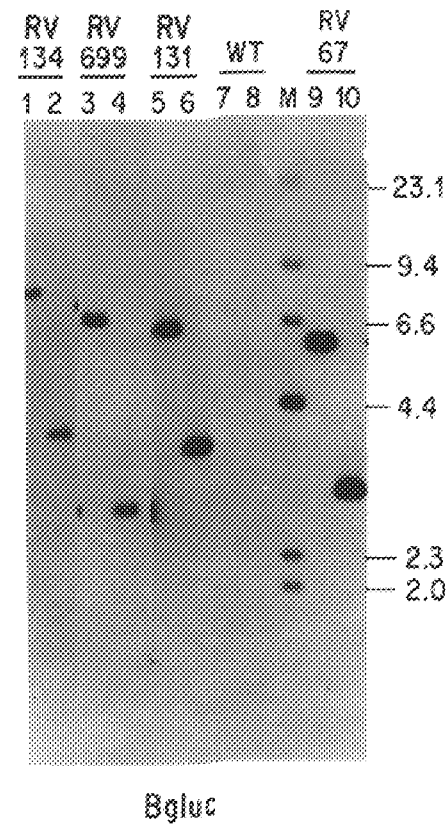

By Southern blot DNA analysis (FIG. 2), the fidelity of the insertion is ascertained for RV134, RV131, RV699 and RV67. First, the recombinant genome of RV134 has the β-glucuronidase expression cassette inserted at the predicted location in the genome (FIGS. 1B and 2A). As shown in FIG. 2B, the 2.95-kb XbaI/EcoRI fragment probe from the HindIII-X probe hybridizes to the 5.02-kb and 7.85-kb HindIII DNA fragments in wild-type and RV134 DNA digests, respectively. The HCMV HindIII-X DNA fragment increases in size by 2.83-kb due to the insertion of the β-glucuronidase expression cassette (FIG. 1B). In HindIII/XhoI double digests, only the predicted 1.06-kb wild-type fragment shows altered mobility (to 3.9-kb) in RV134 (FIG. 2B). Only the 7.85-kb HindIII and 3.9-kb HindIII/XhoI DNA fragments from RV134, and not any wild type DNA fragments, hybridizes with a β-glucuronidase probe (FIG. 2C).

Figure 2D:
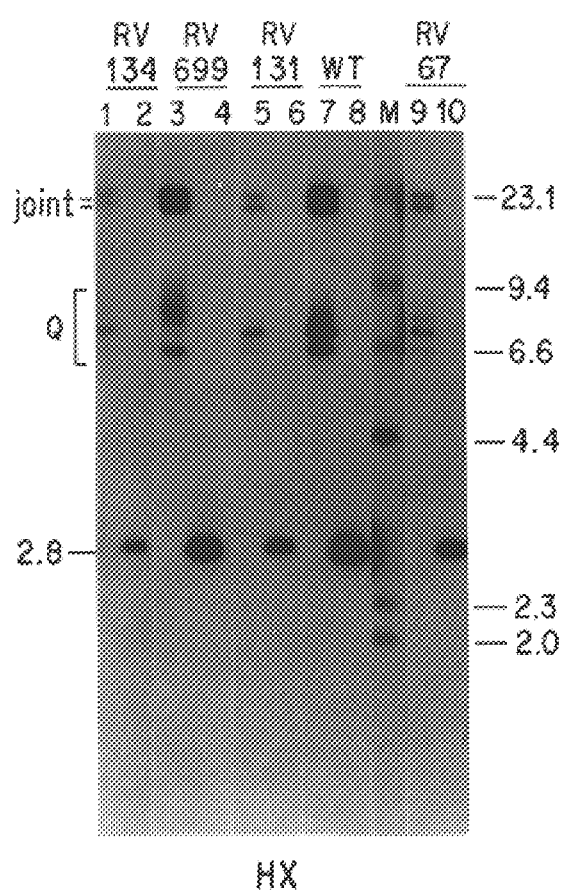
Figure 2E:
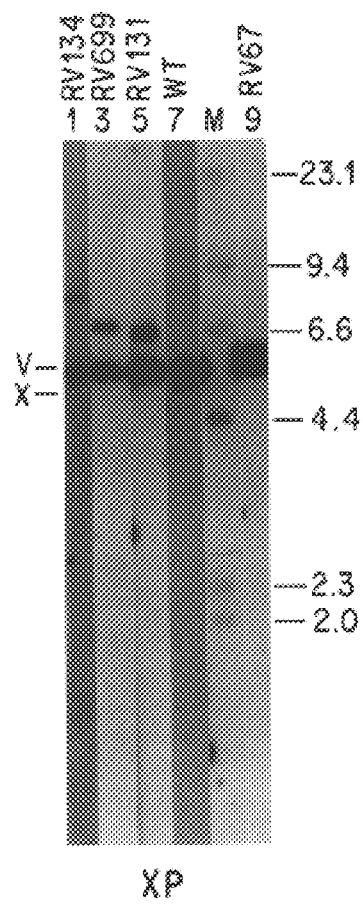

Other Southern blot hybridizations establish that the regions surrounding the β-glucuronidase expression cassette insertion are not altered in RV134 compared to wild type. For example, a 2.83-kb HindIII/XhoI fragment probe from the neighboring HindIII-Q fragment hybridizes to the predicted joint and terminal (heterogenous HindIII-Q) fragments in HindIII digests and to a single 2.83-kb DNA fragment in HindIII/XhoI double digests (FIG. 2D). Using a 1.8-kb XbaI/PstI probe which hybridizes to both HindIII-X and its neighboring HindIII-V DNA fragment, it is shown that only the former DNA restriction fragment, containing the β-glucuronidase insertion, shows altered electrophoretic mobility in RV134 DNA compared to their counterparts in wild-type HCMV DNA (FIG. 2E). Using a total HCMV genomic DNA probe and a probe from the unique long region, no unexpected alterations of the RV134 genome are revealed. The data indicates that the recombination of the β-glucuronidase expression cassette into the RV134 genome occurs as expected.

The 2.95-kb XbaI/EcoRI fragment and β-glucuronidase probes hybridize to 6.7- and 6.5-kb HindIII DNA fragments in digests of RV699 and RV131 DNAs, respectively (FIG. 2B). The increase in size of the HindIII-X DNA fragment (5.02-kb in wild type) reflects the net increase in genome size (1.68-kb in RV699 and 1.49-kb in RV131) predicted by the insertion (FIG. 1C and D). The correct location of the β-glucuronidase insertion within the HindIII-X region is confirmed by hybridization of these probes to HindIII/XhoI digests of the viral DNA. The 2.95-kb XbaI/EcoRI (from HindIII-X) fragment hybridizes to 1.17-, 1.06-, and 2.78-kb fragments from wild type DNA (FIG. 2B).

In RV699, only the 1.17-kb fragment is altered and increases in size to 2.85-kb (and co-migrates with the 2.78-kb fragment in the gel used for this blot; confirmed by SstI and HindIII/PstI digests). In RV131, the β-glucuronidase gene insertion results in the loss of the XHOI restriction site present at the junction of the 1.17 and 1.06-kb fragments (FIG. 2A). The resulting fragment is 3.73-kb; the 2.78-kb fragment remains unaltered (FIG. 2B). Both the 2.85-kb fragment from RV699 and the 3.73-kb fragment from RV131 hybridize with the 2.95-kb XbaI/EcoRI fragment and β-glucuronidase gene probes (FIGS. 2B and 2C).

In a manner identical to that described above for RV134, the regions neighboring the HindIII-X fragment (HindIII-Q and HindIII-V fragments) in RV699 and RV131 do not contain any detectable alterations (FIGS. 2D and 2E). Using a total HCMV genomic DNA probe and a probe from the unique long region, no unexpected alterations of the recombinant virus genomes are revealed.

RV67 is constructed in which a 1.12-kb region containing all of the US11 coding region and most of the US10 coding region is replaced by β-glucuronidase under the control of the US11 promoter (FIG. 1E), resulting in a net increase in size of the HindIII-X fragment of 0.78-kb. Southern blot analysis, similar to that described for the previous recombinant viruses, reveals that only the anticipated alteration in the HCMV genome occurs. The 2.95-kb XbaI/EcoRI fragment and β-glucuronidase probes (FIGS. 2A and 2B, respectively), hybridize to 5.8-kb HindIII and 3.0-kb HindIII/XhoI fragments. The latter represents the insertion within the fused (since the XhoI site is part of the removed sequences) wild type 1.06-kb XhoI and 1.17-kb HindIII/XhoI fragments (FIG. 2A). As before, no alterations are detected in the neighboring HindIII-Q or -V regions (FIGS. 2D and 2E) or in any other region of the RV67 genome.

Figure 3A:
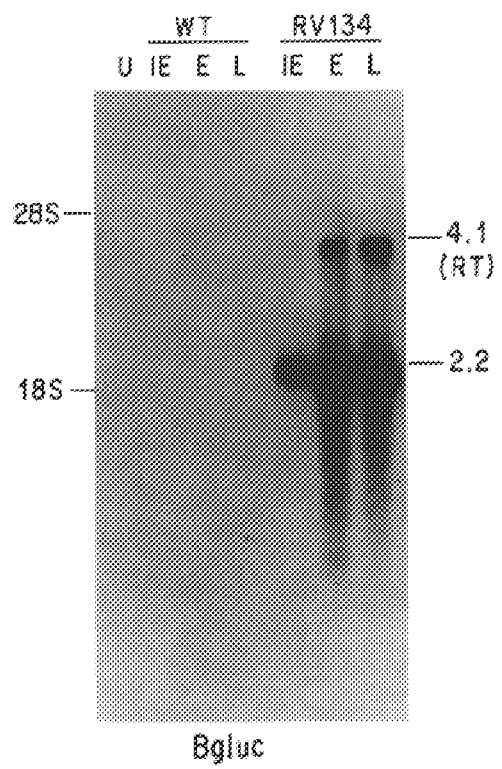

RNA blots of kinetic class transcripts of RV134 demonstrate that the expected 2.2-kb message is present in very abundant amounts at early and late times p.i. as would be predicted from transcripts under the control of the strong 2.7E promoter, as determined using a β-glucuronidase probe (FIG. 3A). A 4.1-kb read-through transcript is also detected. The β-glucuronidase riboprobe does not hybridize with RNA from wild-type infected cells.

Figure 3B:
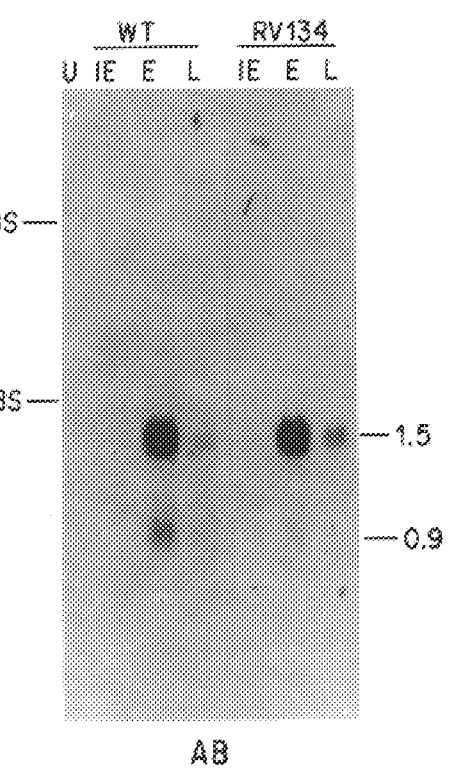
Figure 3C:
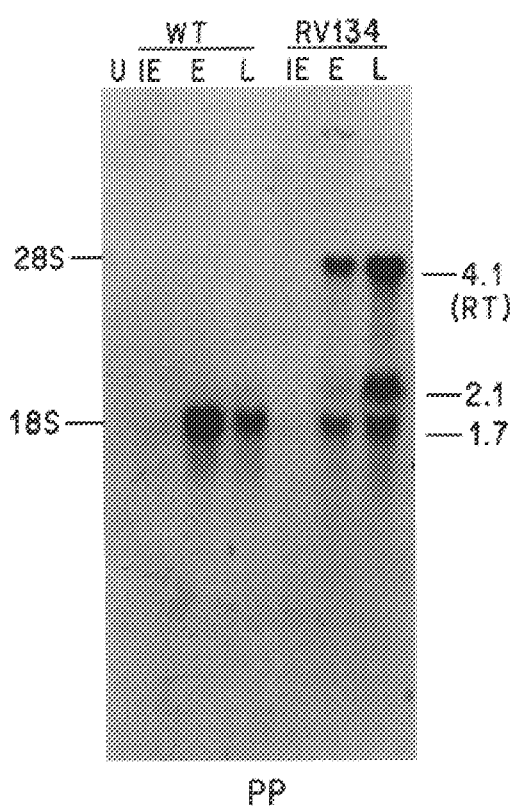

The insertion of this β-glucuronidase expression cassette into the US10/9 intergenic region in RV134 does not have an effect on the kinetics or steady state levels of RNA expression from the adjacent upstream or downstream transcription units, either US11-US10 (1.5- and 0.9-kb RNAs; FIG. 3B) or US9-US8 (1.7-kb RNA; FIG. 3C), respectively, compared to wild-type.

Based on previous fine mapping of transcripts from the wild-type virus (28), blot analysis of kinetic class RNAs confirms the correct insertion of the β-glucuronidase gene within the US11 and US10 transcription units in RV699 and RV131, respectively (FIGS. 4 and 5). Briefly, in wild-type virus, a 1.5-kb early transcript initiates upstream of US11 and terminates at the polyadenylation site downstream of US10. Also, a 0.9-kb transcript initiates upstream of US10 and is 3' co-terminal with the 1.5-kb RNA (thus the US10 riboprobe hybridizes to both transcripts; FIG. 3B).

Figure 4A:
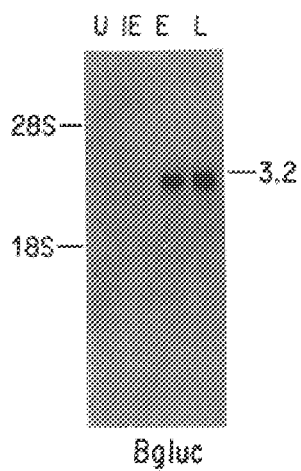
Figure 4B:
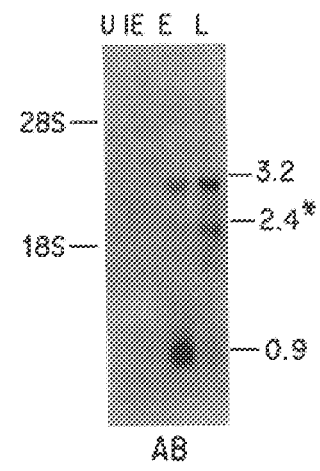
Figure 4C:
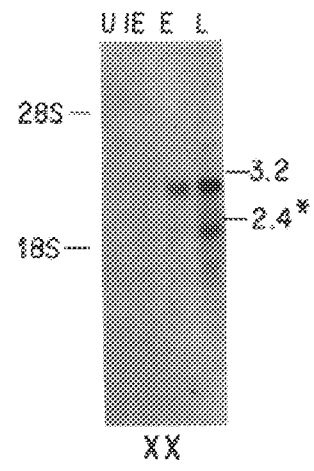

Due to the β-glucuronidase gene insertion in RV699, the 1.5-kb US11-US10 transcript of wild-type increases in size to about 3.2-kb (FIG. 4D) and hybridizes to the β-glucuronidase (FIG. 4A), US10 (FIG. 4B), and US11 (FIG. 4C) riboprobes. The 0.9-kb US10 message is unaltered in RV699 and hybridizes only with the US10 riboprobe (FIG. 4B).

Figure 4D:
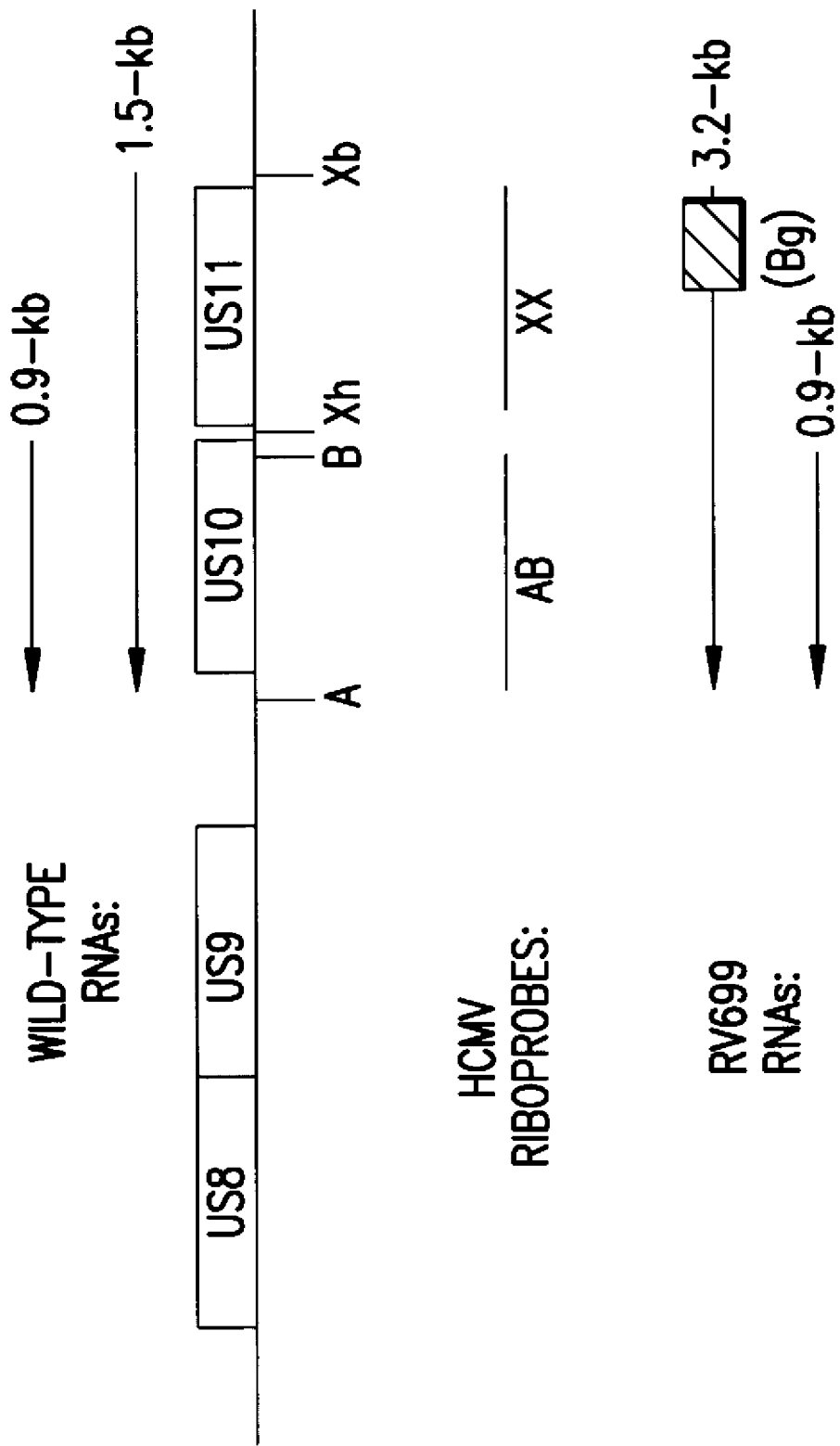
Figure 5A:
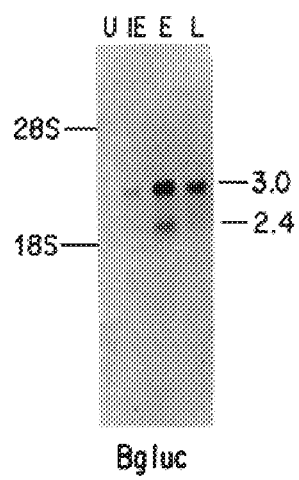
Figure 5B:
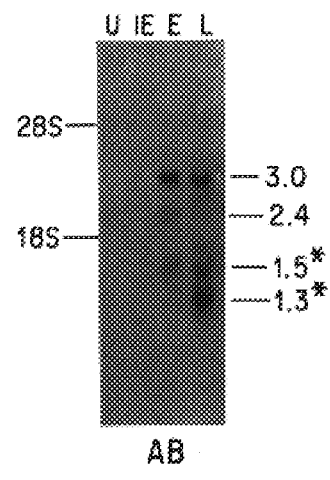
Figure 5C:
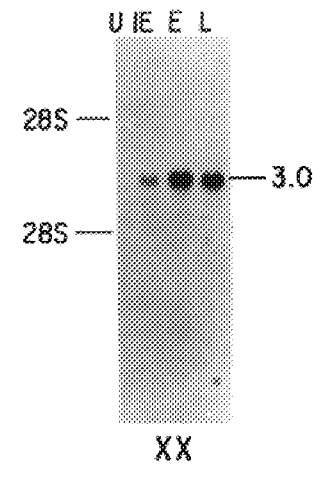
Figure 5D:
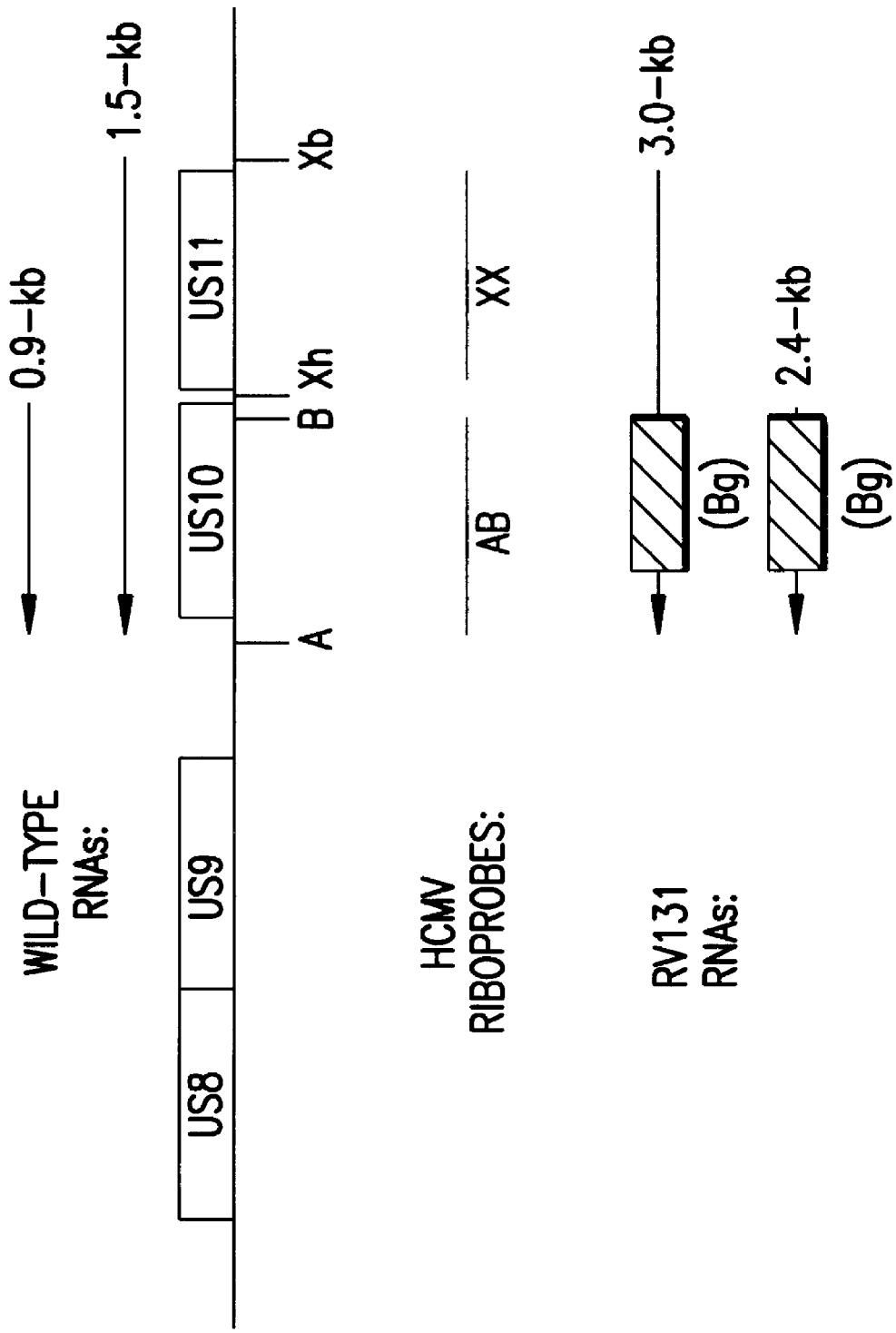

Due to the β-glucuronidase gene insertion in RV131, both the 1.5-kb US10 and 0.9-kb US10 RNAs increase in size to 3.0-and 2.4-kb, respectively (FIG. 5D). Both of these transcripts hybridize with the β-glucuronidase (FIG. 5A) and US10 riboprobes (FIG. 5B), but only the former hybridizes with the US11 riboprobe (FIG. 5C). The Northern blot analyses of FIGS. 4 and 5 reveal additional transcripts, most abundant in late RNAs, using probes which hybridize downstream of the β-glucuronidase gene. For example, the US11 and US10 probes hybridize to a late transcript from RV699 which migrates at about 2.4-kb (FIGS. 4B and C). Also the US10 probe hybridizes to two smaller late RNAs (approximately 1.3- and 1.5-kb) in from RV131 (FIG. 5B). Since these transcripts do not hybridize with a US9 riboprobe, it is believed that they utilize the polyadenylation signal downstream of US10. Therefore, in both cases, in the absence of splicing, the 5' end of the transcripts would lie within the β-glucuronidase gene, about 1.1- to 0.9-kb downstream from its N terminus. These RNAs are not detected by the β-glucuronidase probe since it contains only the 0.6-kb from the N terminus of that gene. It is concluded that there is a cryptic promoter within the β-glucuronidase gene that is activated at late times p.i. by HCMV.

By Northern blot analysis of RV67, a 2.3-kb transcript, which hybridizes with either β-glucuronidase (FIG. 6A) or US10 (FIG. 6B) riboprobes, but not to the US11 riboprobe (since these sequences are completely deleted is expressed from this region in RV67. A 4.1-kb read-through transcript is also detected. The low abundance late transcripts arising from the cryptic promoter within the β-glucuronidase gene of RV131 are also detected in RV67-infected cell RNA with the US10 probe.

The cumulative results from the DNA and RNA blot analyses (FIGS. 2–6) indicate that insertion of this β-glucuronidase expression cassette does not alter expression from neighboring transcription units and allows for predictable construction and identification of HCMV recombinant mutants.

It was previously reported that the HSV-1 late glycoprotein H promoter sequences are closely associated with the polyadenylation signal of the upstream tk gene. This late promoter region is within the tk polyadenylation signal fragment used to terminate transcription in the β-glucuronidase expression cassette used in the RV134 mutant of HCMV. This HSV-1 late promoter is also activated at late times p.i. in RV134 infected HFFs, as evidenced by the 2.1-kb late transcript, which hybridizes with the US8-US9 probe (FIG. 3C). The HSV-1 glycoprotein H promoter is regulated as a true late promoter when incorporated into the HCMV genome (of RV134) since the 2.1-kb transcript is detected (using a US9-US10 intergenic region probe; FIG. 4D) most abundantly only at late times p.i. in the absence, but not in the presence, of PFA, a viral DNA synthesis inhibitor.

Proteins synthesized by RV134 and RV699 are analyzed by SDS-PAGE of total infected cell lysates. For RV134-infected cells, a 68-kD protein, which is the size of the β-glucuronidase monomeric subunit (19), is easily detected in lysates of cells infected with RV134. Corresponding to very abundant amounts of β-glucuronidase RNA in RV134-infected cells (FIG. 3A), this protein is the most abundant protein synthesized (FIG. 7A) or accumulated (FIG. 7B) by late times p.i. The 68-kD protein is not detected in uninfected cell lysates or those from wild-type virus infected cells. This protein is abundant in RV134-infected cells because the virus β-glucuronidase is under the control of the strong 2.7E promoter. The 2.7E promoter was previously utilized to drive β-galactosidase production in HCMV recombinant RC256 (12). β-glucuronidase protein accumulates to similar high levels in cells infected by RC256.

Significant β-glucuronidase accumulation is not detected in RV699-infected cells (FIG. 7B). This is due to the comparatively weak US11 promoter which controls β-glucuronidase expression in RV699 (17), which is responsible for the relatively low steady state level of the 3.2-kb β-glucuronidase-encoding RNA (FIG. 4A) compared to the 2.2-kb message in RV134-infected cells (FIG. 3A).

Immunoprecipitation of US10 and US11 proteins from lysates of HFF cells infected with RV134, RV699, RV131, RV67 or wild-type strain AD169 is conducted according to standard protocols (23). Briefly, the radiolabelled extracts are precleared using preimmune serum and killed *Staphylococcus aureus* (Bethesda Research Laboratories). Proteins binding to immune serum are pelleted using protein A sepharose (Pharmacia). The washed immunoprecipitates are boiled in the presence of 2-mercaptoethanol and electrophoresed in denaturing polyacrylamide gels. The gels are fixed and soaked in 1M salicylate fluor prior to drying and autoradiography (23).

Immune antisera from a rabbit receiving the US11 fusion protein immunoprecipitates a 31-kD protein from lysates of wild type HCMV-infected cells at early times p.i. (FIG. 8A). This protein is not precipitated with preimmune sera (from the same animal), or from uninfected cell lysates. In similar experiments, a 22-kD early protein is specifically immunoprecipitated from lysates of wild type HCMV-infected cells at early times p.i. with antisera from a rabbit receiving the US10 fusion protein (FIG. 8B). The predicted molecular weights of the unmodified US10 and US11 proteins are 20.8-kD and 25.3-kD, respectively (3). The 31-kD protein recognized by the US11 antisera is a glycosylated form of the US11 gene product. As expected, the 31-kD gene product is immunoprecipitated from lysates of RV134- and RV131-infected cells and is absent from lysates of RV699- and RV67-infected cells (FIG. 8A) using that antisera. Although infected at the same multiplicity, less US11 protein is immunoprecipitated from lysates from RV131-infected cells than from lysates of wild-type- or RV134-infected cells. Although this may be due to slightly reduced levels of the 3.0-kb RNA which would encode US11 in RV131 (FIG. 5C), compared to the corresponding 1.5-kb transcript in wild-type or RV134 (FIG. 3B), it may also be due to reduced translatability of the chimeric transcript.

Using the US10 antisera, a 22-kD protein is present in immunoprecipitates of wild-type-, RV134-, and RV699-infected cells, but is not immunoprecipitated from RV131- and RV67-infected cell lysates (FIG. 8B). This data confirms that the US10 or US11 proteins are not expressed from RV131, RV67 and RV699, respectively.

Insertions of the β-glucuronidase gene in RV131 and RV699 result in the placement of a portion of US10 or US11, respectively. Both of these open reading frames are replaced simultaneously in RV67. However, the insertion in RV134 is not within a significant open reading frame, but likely would interfere with either a 3.0-kb or 1.0-kb RNA which is transcribed from the opposite DNA strand as the US6 family genes within this region. In order to assess the effect of these insertions, one step growth curve studies are performed with these viruses in HFF cells. The procedure used is described in Example 6 and the results are shown in FIG. 9.

The eclipse period for each of the four recombinant viruses is 2–3 days. This, as well as the rate of infectious virus production by each of the recombinant, is similar to wild type virus (FIG. 9). These results are in agreement with those published previously for wild type strains of HCMV (24,25). The data suggest that interruption of the transcription units from the opposite strand as the US6 family (RV134), as well as the lack of expression of the US10 and/or the US11 protein, does not have a detectable effect on virus growth kinetics. In low multiplicity infections, the size and appearance of recombinant virus plaques is similar to wild-type plaques.

As part of this invention, it is shown that disruption or replacement of HCMV genes which results in loss of protein expression from these open reading frames, without significant impairment in the ability of recombinant HCMV to replicate in a tissue culture system, demonstrates that those HCMV genes are not essential. These gene products are not supplied in trans, as such, by the host cell. It is concluded that the protein products of the genes set forth in Table 1 are non-essential for HCMV replication and growth in human fibroblasts. Without being bound by the following, two possible reasons for this result are presented. First, if there is conservation of function within the protein products of a family, it may be possible to delete many family members without an apparent effect. Another alternative is that there may be clusters of tissue culture dispensable genes in the HCMV US, just as in the HSV US (7,9).

Based mainly on hydropathy analysis of proteins deduced from DNA sequence data, it has been proposed that the US10 and US11 gene products are membrane glycoproteins (14). This hypothesis was supported by data from Gretch and co-workers which demonstrated that a monoclonal antibody which reacts with HCMV virion glycoprotein complex II (gcII) also immunoprecipitates US10 and US11 gene products synthesized in vitro (16). Also, the inventors' results from experiments utilizing an inhibitor of glycosylation, tunicamycin (Sigma), suggest that the US11 gene product is glycosylated. Through the use of viral recombinant in the HSV system, it has been shown that several of the virion envelope glycoprotein genes are non-essential for virus growth in tissue culture (6,7,26–28). These include gC, gE, gG, and gI. Except for gC, these dispensable glycoproteins lie in the US region of HSV, just as US10 and US11 map in the US region of HCMV. The only essential gene within the HSV US encodes the virion glycoprotein gD (29). To date, it remains unclear as to the extent to which the products of the US10 and US11 genes may be present in the HCMV-infected cell membrane of the virion envelope.

Analysis of the β-glucuronidase gene-containing RNA expression in the HCMV recombinant reveals several interesting results. Transcripts which are expressed at late times p.i. often do not efficiently terminate at the first-encountered poly-adenylation signal and can be called read-through RNAs. β-glucuronidase gene expression in RV134 is under the control of the 2.7E promoter which is very active at both early and late times p.i. When early and late transcripts are compared, the amount of the 4.1-kb read-through transcript increases about three-fold at late times (FIG. 3A). The read-through of β-glucuronidase gene-containing RNAs observed in RV134 is not simply explained by the heterologous HSV tk polyadenylation signal not being recognized as efficiently as a HCMV polyadenylation signal since an increase of read-through is observed at late times in β-glucuronidase gene-containing RNAs which should terminate at the endogenous US10 proximal polyadenylation signal from RV67 (FIG. 6A). This increased propensity for read-through RNAs at late time p.i. has also been observed for entirely endogenous HCMV US6 and US7 late messages (17).

Another observation is that the chimeric β-glucuronidase gene-containing RNAs do not display the same kinetics as their wild-type counterparts. For example, steady state cytoplasmic levels of the 3.2-kb message from RV699 infected cells (FIG. 4A), 3.0-kb transcript from RV131 infected cells (FIG. 5A) and the 2.3 kb RNA from RV67 infected cells (FIG. 6A), are only slightly, if at all, reduced at late times compared to early times p.i. (p.i.). Like the 1.5-kb US11-US10 transcript from wild-type infected cells, these chimeric messages are transcribed under the control of the US11 promoter. In wild-type virus-infected cells, this 1.5 kb message is greatly reduced at late times compared to early times p.i. (FIG. 3B; (17)). There are at least two possibilities for this discrepancy. First, the presence of β-glucuronidase gene sequences on a transcript may stabilize it so it has a longer cytoplasmic half-life than the wild-type RNAs. Secondly, negative intragenic (cis) transcriptional regulatory sequences may be abrogated as a result of the β-glucuronidase gene insertion into the transcription unit.

Figure 3D:
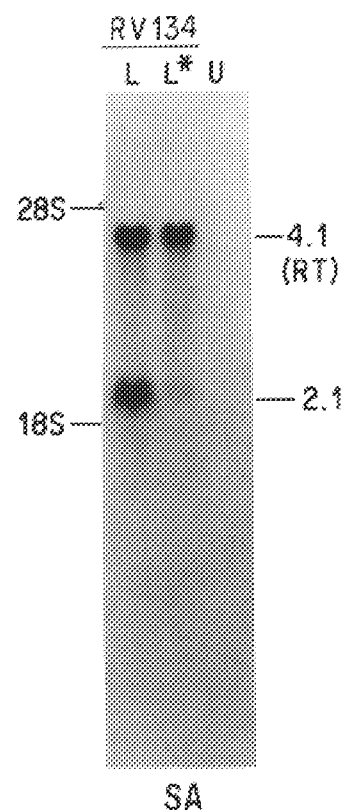
Figure 3E:
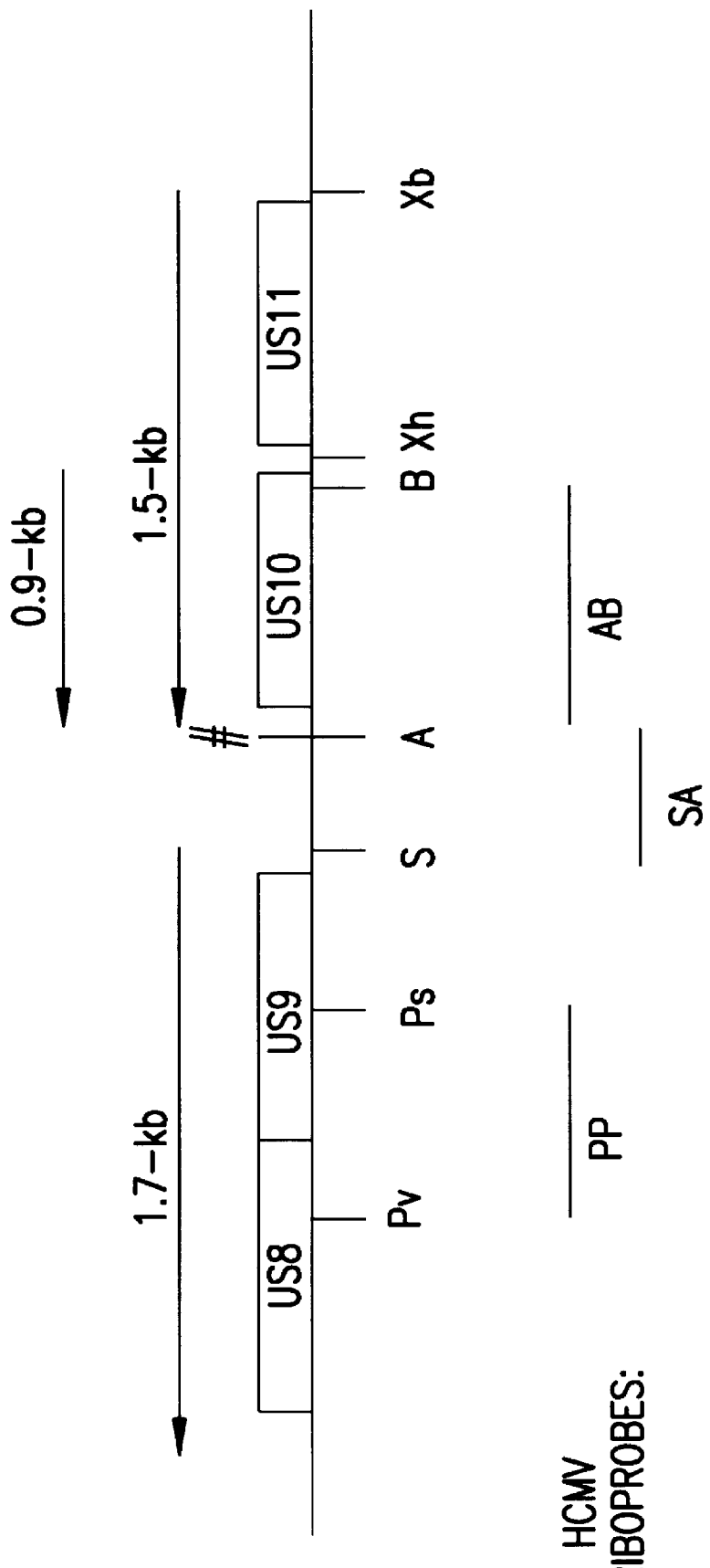

A third observation is that the HSV-1 true late gH promoter is also regulated as a HCMV late promoter when it is incorporated into the genome of RV134 (FIG. 3D). This suggests that similar mechanisms may regulate late expression of these related viruses. Recognition of heterologous virus signals has been reported previously between HSV and HCMV: HSV-1 recognizes the HCMV "a" DNA packaging and cleavage sequence, and HCMV functions(s) can complement an HSV ICP0 mutant.

The second embodiment of this invention comprises an assay to screen for inhibitors of HCMV. The assay includes the use of recombinant HCMV with an inserted marker gene as described above (where the β-glucuronidase gene replaces or disrupts an HCMV gene), as well as recombinant HCMV where the insertion is intergenic, that is, the β-glucuronidase gene is inserted between two HCMV genes so as to neither replace nor disrupt those genes.

The screening method takes advantage of the ability of β-glucuronidase to cleave a conjugated chemical substrate, thereby releasing a fluorescing product or a chromophoric product. In the case of the conjugate containing the fluorescing moiety, the levels of fluorescence are measured on a microfluorimeter. If a test compound screened inhibits HCMV, it will reduce expression from the virus and therefore result in reduced levels of β-glucuronidase. Reduced enzyme levels will mean a reduction in the cleavage yielding the fluorescing product. Reduced levels of fluorescing product will result in lower microfluorimeter readings, which signifies an inhibition of HCMV by the test compound.

The conjugated chemical substrate consists of a fluorescing moiety which, when conjugated to a sugar, does not fluoresce. A particularly preferred conjugate is methylumbelliferylglucuronide, sold under the trade name muglucuronide by Sigma Chemical. This conjugate consists of a fluorescing moiety, methylumbelliferin, and a sugar which is a derivative of glucuronic acid.

In the case of the conjugate containing the chromophore, the extent of the color change is measured visually or spectrophotometrically. If a test compound screened inhibits HCMV, it will reduce expression from the virus and therefore result in reduced levels of β-glucuronidase. Reduced enzyme levels will mean a reduction in the cleavage yielding the chromophore. Reduced levels of the chromophore will result in a reduction of the extent of the color change normally seen when the chromophore is released, which signified an inhibition of HCMV by the test compound.

The conjugated chemical substrate consists of a chromophore conjugated to a sugar. One example of such a chromophoric conjugate is p-nitrophenyl-β-D-glucuronide (Sigma Chemical Co.) which, upon cleavage, is converted from a pale yellow color to a deep yellow color. An inhibitor of HCMV in this assay system will reduce the cleavage of this conjugate and tend to keep the color pale yellow rather than deep yellow.

Another example of a chromophoric conjugate is 5-bromo-4-chloro-3-indolyl-β-D-glucuronide (Clontech Labs.) which, upon cleavage, is converted from a clear to a blue-green color. An inhibitor of HCMV in this assay system will reduce the cleavage of this conjugate and tend to keep the color clear rather than blue-green.

In conducting the assay for inhibitors of HCMV, the use of the recombinant HCMV RV145 is preferred.

The assay of this invention provides a convenient method for screening for inhibitors of HCMV. Viral growth, as measured by β-glucuronidase assay, is detected after a five day incubation period, rather than the 7–8 day period needed for other, more labor-intensive techniques.

In order that this invention may be better understood, the following examples are set forth. The examples are for the purpose of illustration only and are not to be construed as limiting the scope of the invention.

EXAMPLES

Example 1

Construction of Marker-Expressing Recombinant HCMV

A. Preliminary Steps

HCMV strain AD169, which contains wild-type genomic DNA, is obtained from the American Type Culture Collection (ATCC VR 538) and propagated according to standard protocols. The numerical base sequence designation of that HCMV DNA is that described previously (14).

The HCMV strain AD169 genomic HindIII-X and -G DNA fragments are cloned into the plasmid pAT153 (30), yielding plasmids designated pHind-X and pHind-G, respectively, by Oram et al. (31). The HCMV strain AD169 XbaI-P and BamHI-S DNA fragments are cloned from virion DNA into the XbaI and BamHI sites of plasmid pACYC184 to yield pXbaI-P and pBam-S, respectively. Plasmid pBam-U contains the HCMV BamHI-U fragment, subcloned from the pHind-G, into pACYC184. A fusion protein vector used (pT7protA) is constructed from pRIT2T (Pharmacia) by replacing its promoter and termination signals with the bacteriophage T7 gene 10 promoter and termination signals. All plasmid DNA manipulations are done according to standard protocols (23). Plasmids for recombination into the HCMV genome are constructed in a pT7-1 (US Biochemical) backbone.

The starting plasmid is pBgluc which contains the 1.9 kb prokaryotic β-glucuronidase gene (Clontech, Palo Alto, Calif.) inserted into the SmaI site within the pT7-1 polylinker. The order of the restriction sites within the polylinker of pBgluc relative to the β-glucuronidase gene is: HindIII, PstI, SalI, XbaI, BamHI, 5'-β-glucuronidase-3', SstI and EcoRI. To facilitate homologous recombination into the viral genome, the appropriate viral sequences are cloned 5' and 3' to the β-glucuronidase gene in pBgluc.

The products of these preliminary manipulations are used in the construction of β-glucuronidase marker-expressing recombinant HCMVs as described below. Plasmids containing the marker gene are then co-transfected with wild-type HCMV DNA. Infectious HCMV DNA is isolated from partially purified nucleocapsids after sorbitol cushion density gradient centrifugation (2). The nucleocapsids are resuspended in 50 mM Tris (pH7.5)/1 mM $MgCl_2$. The nucleocapsid suspension is made (0.1M Tris (pH8.0)/0.1M EDTA/0.1M NaCl) and lysed by the addition of sarkosyl to a final concentration of 0.5%. After digestion with 100 $\mu$g/ml of proteinase K (3 hours for 50° C.), phenol-chloroform extraction is performed and the resulting nucleic acids are precipitated with ethanol. The spooled DNA is dried briefly and resuspended overnight in 1×TE (10 mM Tris pH 8.0/1 mM EDTA).

Co-transfection is conducted in human foreskin fibroblast (HFF) cells. HFF cells are isolated and used below passage twenty to ensure viral replication. The cells are grown in Dulbecco's modified Eagle medium (DMEM; Mediatech) containing 10% fetal calf serum (Gibco) and 25 mM HEPES (N-2-hydroxyethylpiperazine-N'-2-ethanesulfonic acid).

Prior to co-transfection, the marker-expression plasmids are linearized at a unique site at the end of the viral sequences. HFF cells are split so that they are 70–80% confluent on the day of transfection. The cells are trypsinized and suspended to $5.6 \times 10^6$ cells per ml in DMEM/10% FCS/25 mM HEPES. The DNA is transfected using the modified calcium phosphate co-precipitation technique. Briefly, 1.5 $\mu$g of infectious HCMV DNA, 2 $\mu$g of linearized plasmid DNA, and 2 $\mu$g sonicated salmon sperm are mixed in the calcium chloride solution (300 $\mu$l containing 10 mM Tris pH 7.0/250 mM calcium chloride) and chilled on ice. To initiate the co-precipitation, the DNA is removed from the ice and 300 $\mu$l 2×HeBS pH 6.95 (at room temperature); (1×HeBS is 19.2 mM HEPES, 137 mM NaCl, 5 mM KCl, 0.8 mM sodium phosphate, pH 7.05, 0.1% dextrose) is added dropwise with gentle mixing. As soon as the slightest precipitate becomes visible, the precipitate is placed on ice (to prevent the formation of further precipitate). The precipitate is mixed with $3 \times 10^6$ cells and placed in a 82 mm tissue culture plate. After six hours at 37° C., the media is removed and the cells are shocked with 20% dimethyl sulfoxide in 1×HeBS for two minutes. The cells are washed twice with PBS and growth media is added. The media is changed every 4–7 days. When cytopathic effect becomes extensive (14–21 days post-transfection), virus is harvested according to standard protocol (24). The resulting virus stock is serially diluted and plated on HFF cells. After 10–12 days, the infected cells are overlayed with 0.5% agarose in DMEM containing 100 $\mu$g/ml X-glu (5-bromo- 4-chloro-3-indole-1-glucuronide; Biosynth International Inc., Skokie, Ill.).

Marker-expressing recombinant viruses are isolated as follows: Blue (recombinant virus-containing) plaques are picked three hours to several days after adding the overlay (depending on the strength of the promoter controlling β-glucuronidase expression). For example, blue plaques containing RV134 (described below) are obtained at a frequency of about 5%. In some cases, the original transfection plate is overlayed for the first blue plaque identification. Recombinant viruses are plaque purified four times (one round of plaque purification after all plaques on the plate appear blue).

Specific β-glucuronidase marker-expressing recombinant HCMVs will now be described in the remainder of this Example 1 and as shown in FIG. 1.

B. RV134

To insert β-glucuronidase in the US10/US9 intergenic region, p2.7EBgpAUS10/9 is constructed (FIG. 1B). Sequentially, this plasmid contains the ApaI/ApaI fragment (bases 14834 to 13527, containing the US11 and US10 sequences; from pHind-X); the 768-b SspI/SmaIII (−713 to +55) promoter fragment from pBam-U (42); β-glucuronidase (for all constructions, from pBgluc); an 180-b SmaI/HaeIII HSV-1 tk polyadenylation signal fragment (obtained from HSV-1 macroplaque strain and containing a polyadenylation signal (32); and the 2.0-kb ApaI/BamHI fragment (bases 13527 to 11548, containing US9 and US8 sequences; from pHind-X). Plasmid p2.7EBgpAUS10/9 is linearized at the unique restriction site (HindIII) at one end of the viral sequences flanking B-glucuronidase. The linearized plasmid is then co-transfected with HCMV wild-type DNA (as described above) and recombinant virus RV134 is isolated.

C. RV699

In order to replace HCMV open reading frame US11, pBgdUS11 is constructed (FIG. 1C). Sequentially, this plasmid contains the 1.8-kb PstI/XbaI fragment (bases 16713 to 14897, containing US13, US12, and US11 promoter sequences; from pXbaI-P); β-glucuronidase; and the 1.5-kb SalI/SstII fragment (bases 14677 to 13215, containing C-terminal US11 sequences and US10 sequences; from pHind-X). The endogenous US11 early promoter controls β-glucuronidase gene expression in this construct. The plasmid pBgdUS11 is then linearized at its unique PstI site and co-transfected with HCMV wild-type DNA (as described above) and recombinant virus RV699 is isolated.

D. RV131

Figure 1D:
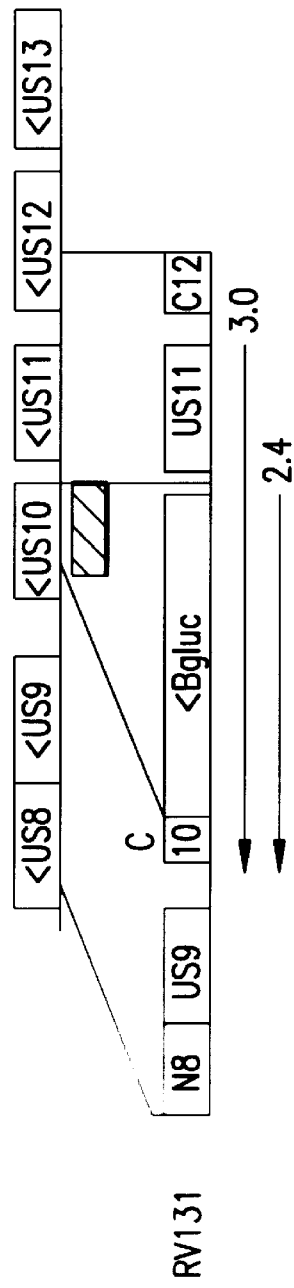

In order to replace HCMV open reading frame US10, pBgdUS10 is constructed (FIG. 1D). Sequentially, this plasmid contains the 1.2-kb HindIII/XhoI fragment (bases 15362 to 14189, containing US11 coding sequences and US10 promoter sequences; from pHind-X); β-glucuronidase; and the 1.8-kb SmaI/EcoRI fragment (bases 13782 to 11949, containing C-terminal US10 sequences, US9, and N-terminal US8 sequences; from pHind-X). The endogenous, weak, US10 promoter controls β-glucuronidase expression in this plasmid. The plasmid pBgdUS10 is then linearized at its unique EcoRI site and co-transfected with HCMV wild-type DNA (as described above) and recombinant virus RV131 is isolated.

E. RV67

Figure 1E:
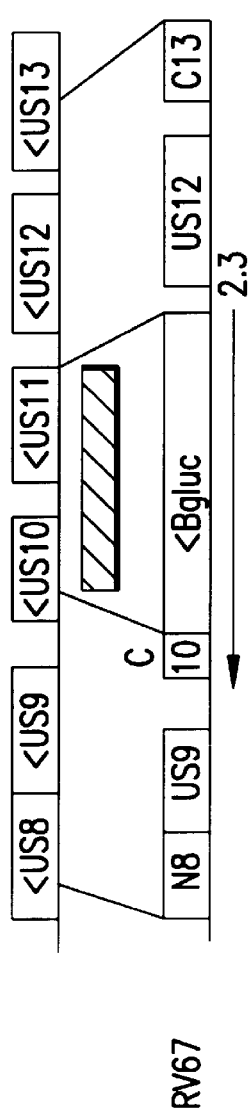

To replace HCMV open reading frame US10 and US11 simultaneously, pBgdUS11/10 is constructed (FIG. 1E). This plasmid is similar to pBgdUS10, except that it has the 1.8-kb PstI/XbaI fragment (bases 16713 to 14897, containing US13, US12, and US11 promoter sequences; from pXbaI-P) inserted upstream of β-glucuronidase, instead of the 1.2-kb HindIII/XhoI fragment. The plasmid pBgdUS11/10 is then linearized at its unique EcoRI site and co-transfected with HCMV wild-type DNA (as described above) and recombinant virus RV67 is isolated.

F. RV145

Figure 1F:
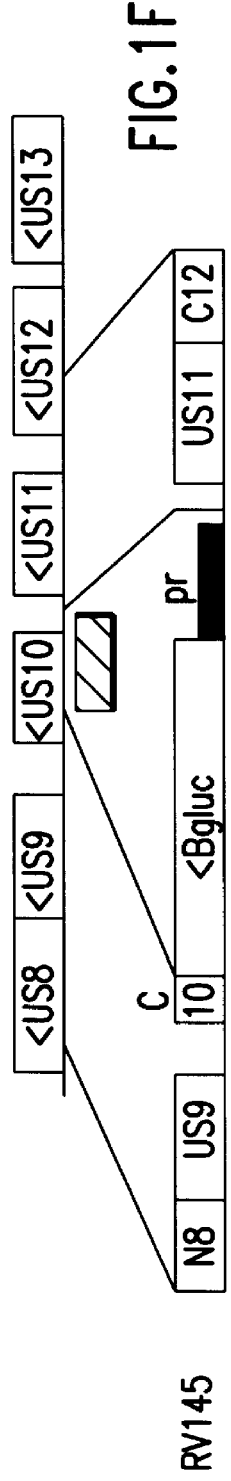

To replace HCMV open reading frame US10 (as in RV131), but have the β-glucuronidase gene under the control of the strong 2.7E promoter, p2.7EBgdUS10 is constructed (FIG. 1F). Sequentially, this plasmid contains the 1.2-kb HindIII/XhoI fragment (bases 15362 to 14189, containing US11 coding sequences and US10 promoter sequences; from pHind-X); the 768-b SspI/XmaIII (-713 to +55) 2.7E promoter fragment; β-glucuronidase; and the 1.8-kb SmaI/EcoRI fragment (bases 13782 to 11949, containing C-terminal US10 sequences; US9, and N-terminal US8 sequences; from pHind-X). The plasmid p2.7EBgdUS10 is then linearized at its unique EcoRI site and co-transfected with HCMV wild-type DNA (as described above) and recombinant virus RV145 (ATCC VR 2329) is isolated.

G. RV80

Figure 1G:
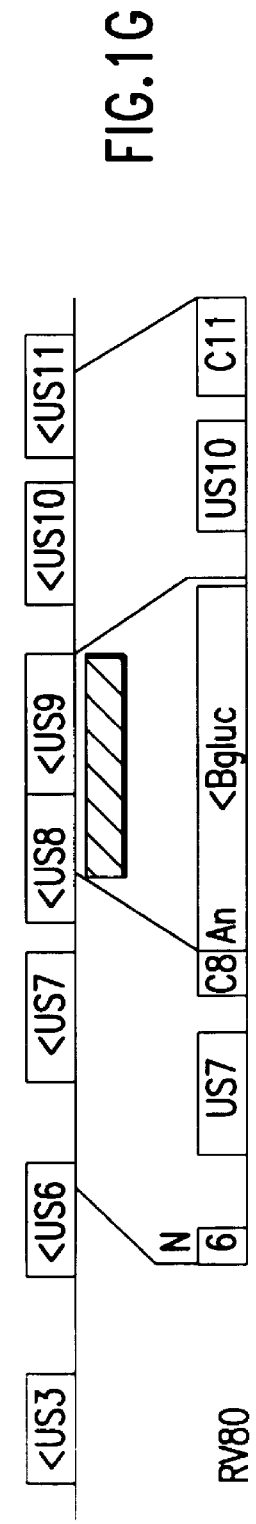

To replace HCMV open reading frames US8 and 9 simultaneously, pBgdUS9/8 is constructed (FIG. 1G). Sequentially, this plasmid contains the 1.5-kb SalI/SstII fragment (bases 14677 to 13215, containing a portion of US11, US10, and the US9 promoter sequences; from pHind-X); β-glucuronidase; the 180-b SmaI/HaeIII HSV-1 tk polyadenylation signal fragment; and the 1.6-kb EcoRI/HindIII fragment (bases 11949 to 10343, containing C-terminal US8 sequences, US7, and N-terminal US6 sequences; from pHind-X). The endogenous US9 promoter controls β-glucuronidase expression in this plasmid. The plasmid pBgdUS9/8 is then linearized at its unique SalI site and co-transfected with HCMV wild-type DNA (as described above) and recombinant virus RV80 is isolated.

H. RV725

Figure 1H:
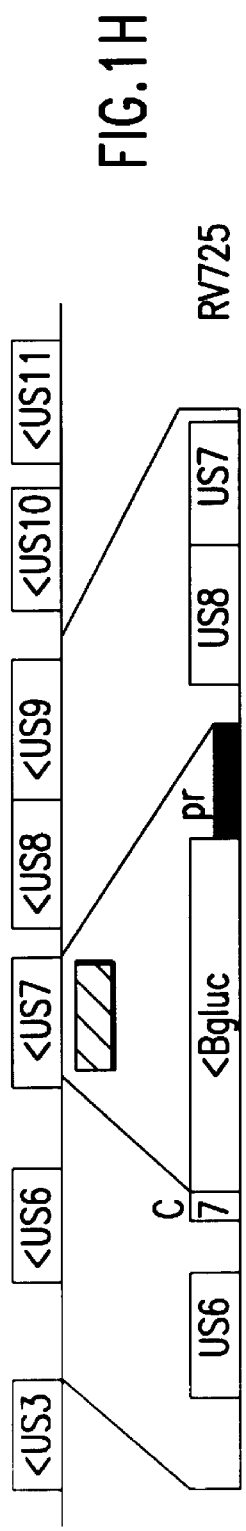

To replace HCMV open reading frame US7, p2.7EBgdUS7 is constructed (FIG. 1H). Sequentially, this plasmid contains the 1.7-kb SstII/BamHI fragment (bases 13215-11548, containing US9 and US8; from pHind-X); the 768-b SspI/XmaIII (-713 to +55) 2.7E promoter fragment; β-glucuronidase; and the 1.7-kb PstI/PstI fragment (bases 10953 to 9247, containing the C-terminal US7 sequences and US6; from pHind-X and pHind-G). The 2.7E promoter controls β-glucuronidase expression in this plasmid. The plasmid p2.7EBgdUS7 is then linearized at its unique XhoI site and co-transfected with HCMV wild-type DNA (as described above) and recombinant virus RV725 is isolated.

I. RV69

Figure 1I:
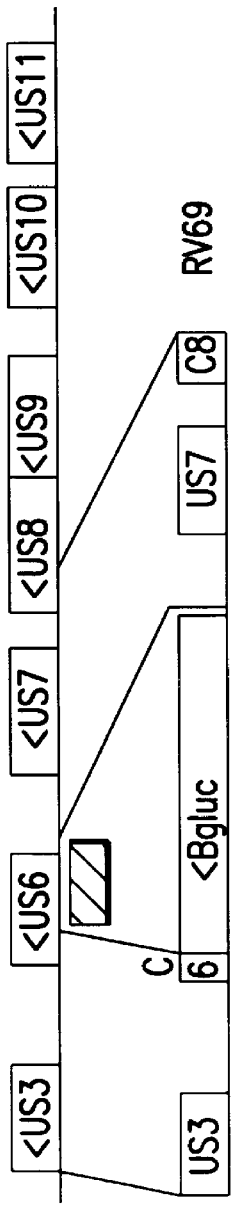

To replace HCMV open reading frame US6, pBgdUS6 is constructed (FIG. 1I). Sequentially, this plasmid contains the 1.5-kb EcoRI/EcoRV fragment (bases 11949 to 10471, containing the C-terminal sequences of US8, US7, and the US6 promoter sequences; from pHind-X); β-glucuronidase; and the 1.5-kb HpaI/SstII fragment (bases 10095 to 8568, containing the C-terminal sequences of US6 and US3; from pHind-G). The endogenous US6 promoter sequences control β-glucuronidase expression in this plasmid. The plasmid pBgdUS6 is then linearized at its unique HindIII site and co-transfected with HCMV wild-type DNA (as described above) and recombinant virus RV69 is isolated.

J. RV102

Figure 1J:
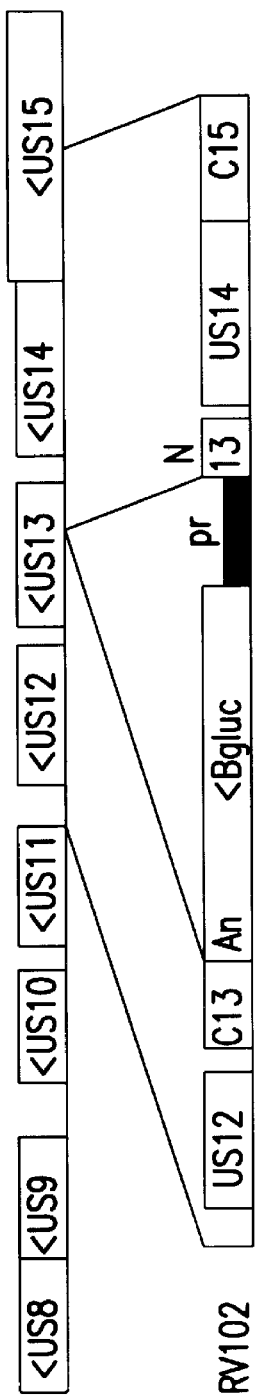

To disrupt HCMV open reading frame US13, p2.7EBgiUS13 is constructed (FIG. 1J). Sequentially, this plasmid contains the 2.0-kb SalI/NcoI fragment (bases 18489 to 16465, containing the C-terminal sequences of US15, US14, and the N-terminal sequences of US13; from pXba-P); the 768-b SspI/XmaIII (−713 to +55) 2.7E promoter fragment; β-glucuronidase; the 180-b SmaI/HaeIII HSV-1 tk polyadenylation signal fragment; and the 1.6-kb NcoI/XbaI fragment (bases 16465 to 14897, containing the C-terminal sequences of US13 and US12; from pXba-P). The 2.7E promoter controls β-glucuronidase expression in this plasmid, as well as in the next four plasmids of this Example (parts K through N). The plasmid p2.7EBgiUS13 is then linearized at its unique XbaI site and co-transfected with HCMV wild-type DNA (as described above) and recombinant virus RV102 is isolated.

K. RV88

Figure 1K:
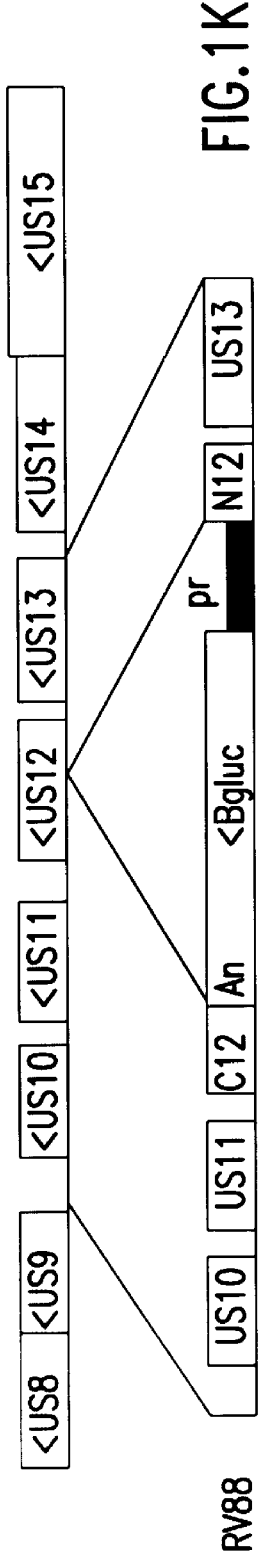

To disrupt HCMV open reading frame US12, p2.7EBgiUS12 is constructed (FIG. 1K). Sequentially, this plasmid contains the 1.2-kb PstI/EcoRV fragment (bases 16713 to 15514, containing the C-terminal sequences of US13 and the N-terminal sequences of US12; from Xba-P); the 768-b SspI/XmaIII (−713 to +55) 2.7E promoter fragment; β-glucuronidase; the 180-b SmaI/HaeIII HSV-1 tk polyadenylation signal fragment; and the 2.3-kb EcoRV/SstII fragment (bases 15514 to 13215; containing the C-terminal sequences of US12, US11, and US10; from pXbaI-P and pHind-X). The plasmid p2.7EBgiUS12 is then linearized at its unique PstI site and co-transfected with HCMV wild-type DNA (as described above) and recombinant virus RV88 is isolated.

L. RV91

To disrupt HCMV open reading frame US27, p2.7EBgiUS27, is constructed (FIG. 1M). Sequentially, this plasmid contains the 1.6-kb SalI/NaeI fragment (bases 31160–32757, containing N-terminal US26 and N-terminal US27 sequences; from pBam-S); the 768-b SspI/XmaIII (−713 to =55) 2.7E promoter fragment: β-glucuronidase; the 180-b SmaI/HaeIII HSV-1 tk polyadenylation signal fragment; and the 1.9-kb NaeI/SstI fragment (bases 32757 to 34695, containing the C-terminal amino acids of US27 and US28; from pBam-S). The plasmid p2.7EBgiUS27 is then linearized at its unique SalI site and co-transfected with HCMV wild-type DNA (as described above) and recombinant virus RV91 is isolated.

M. RV92

Figure 1N:
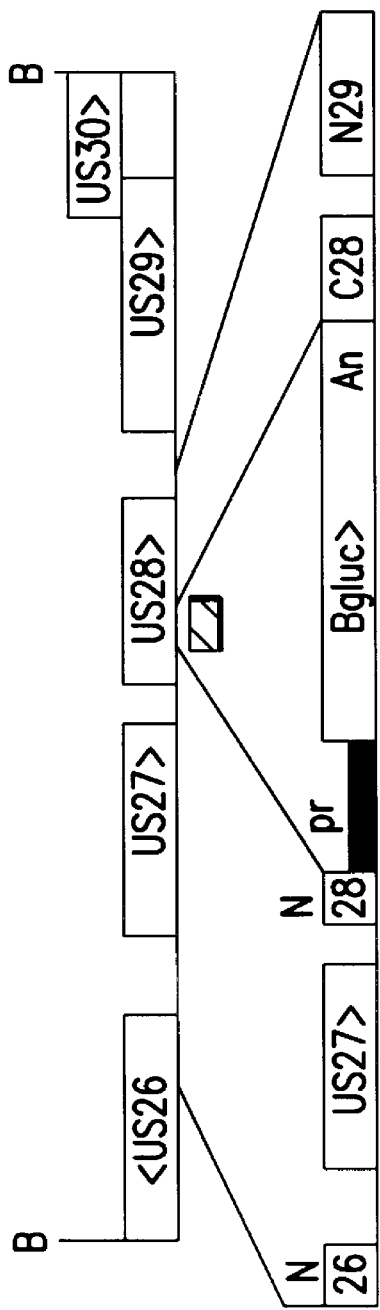

To replace HCMV open reading frame US28, p2.7EBgdUS28 is constructed (FIG. 1N). Sequentially, this plasmid contains the 1.9-kb SstII/NotI fragment (bases 32052 to 33932, containing US27 and the N-terminal sequences of US28; from pBam-S); the 768-b SspI/XmaIII (−713 to +55) 2.7E promoter fragment; β-glucuronidase; the 180-b SmaI/HaeIII HSV-1 tk polyadenylation signal fragment; and the 1.6-kb StuI/NcoI fragment (bases 34135 to 35764, containing the C-terminal sequences of US28 and N-terminal sequences of US29; from pBam-S). The plasmid p2.7EBgdUS28 is then linearized at its unique HindIII site and co-transfected with HCMV wild-type DNA (as described above) and virus RV92 is isolated.

N. RV101

Figure 1O:
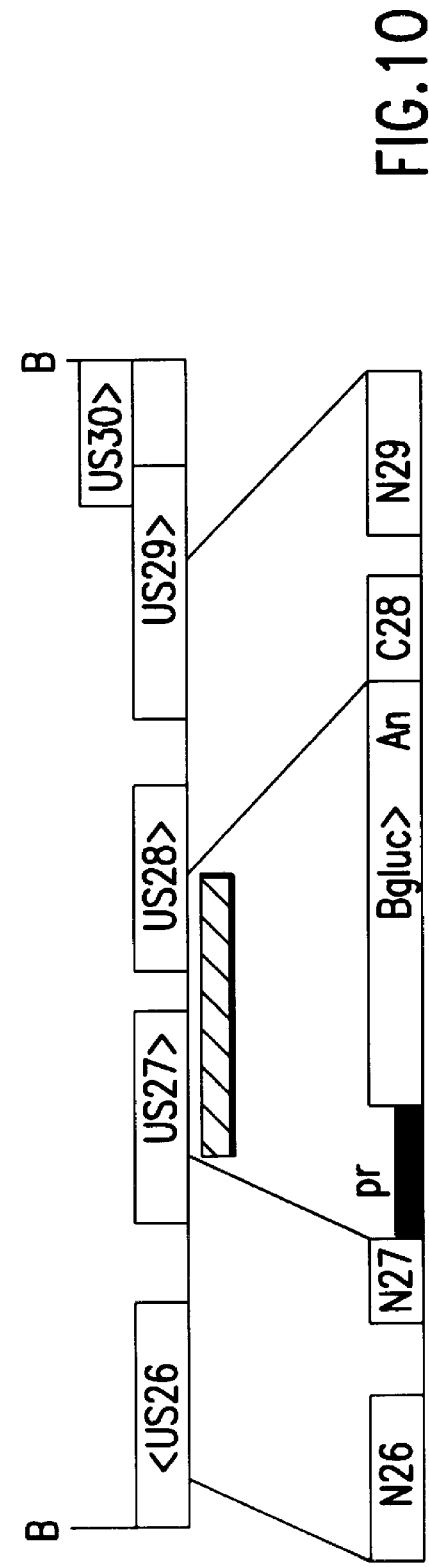

To replace HCMV open reading frames US27 and US28 simultaneously, p2.7EBgdUS27/28 is constructed (FIG. 1O). Sequentially, this plasmid contains the 1.6-kb SalI/NaeI fragment (bases 31160 to 32757, containing N-terminal US26 and N-terminal US27 sequences; from pBam-S; the 768-b SspI/XmaIII (−713 to +55) 2.7E promoter fragment; βglucuronidase; the 180-b SmaI/HaeIII HSV-1 tk polyadenylation signal fragment; and the 1.6-kb StuI/NcoI fragment (bases 34135 to 35764, containing the C-terminal sequences of US28 and N-terminal sequence of US29; from pBam-S). The plasmid p2.7EBgdUS27/28 is then linearized at its unique HindIII site and co-transfected with HCMV wild-type DNA (as described above) and recombinant virus RV101 is isolated.

O. RV670

In one instance, when pBgdUS11 is co-transfected with HCMV DNA, instead of replacing US11 to form RV699 (see above), recombinant virus RV670 is isolated containing an unexpected deletion. DNA blot hybridization analyses (using the procedure of Example 2 below) reveal that RV670 is created as a result of homologous recombination within the US11 upstream flanking sequences and non-homologous recombination of the downstream prokaryotic plasmid sequences with HCMV joint region sequences. The deletion is extensive and includes portions of both the US region and the IRS region. Specifically, the following open reading frames are deleted: US11, US9, US8, US7, US6, US5, US4, US3, US2, US1 and IRSI.

Example 2

Southern blot analysis

Miniprep recombinant virus DNA (for Southern blot analysis) is isolated from the cytoplasm of infected cells. The procedure used is similar to that used for the isolation of total cytoplasmic RNA (below), except that modified 2×PK buffer is used (containing 1% sarkosyl instead of 2% SDS) and there is a 20 minute treatment with RNAase A (25 μg/ml at 37° C.) prior to the proteinase K treatment.

Restriction endonuclease digested viral DNA is electrophoresed through 0.6% agarose gels. The DNA is blotted to Nytran (Schleicher and Schuell, Keene, N.H.), cross-lined by ultraviolet light, and prehybridized for 4–16 hours in 50% formamide, 5×SSC, 5×Denhardts, 50 mM sodium phosphate, pH 6.5, 1% glycine, 100 μg/ml denatured sonicated salmon sperm DNA and 0.1% SDS at 42° C. High specific activity DNA probes are made by using a random priming kit (Bethesda Research Laboratories, Rockville, Md.) and hybridized at 42° C. in 50% formamide, 5×SSC, 1×Denhardts, 20 mM sodium phosphate, pH 6.5, 1 mM EDTA, 1100 μg denatured sonicated salmon sperm DNA per ml, and 0.1% SDS for 18 hours. The blots are washed twice in 2×SSC/0.1% SDS at room temperature for five minutes. Three high stringency washes are done in 0.1×SSC/0.1% SDS at 50 °_C. for 20 minutes each. The washed blots are exposed to XAR5 film (Kodak) with DuPont Cronex intensifying screens at −70° C. Southern blot analyses are performed on all recombinant viruses listed in Table 1 and described in Example 1. Illustrative results of analyses on RV134, RV131, RV699 and RV67 in comparison with wild-type virus AD169 are as described above and as depicted in FIG. 2.

Example 3

Northern blot analysis

Total cytoplasmic RNA is isolated by the NP40 lysis method as described previously (23). HCMV kinetic class RNA is isolated after infection of HFF cells at a multiplicity of infection (moi) =5. Immediate-early RNA is isolated at eight hours p.i. from cells in the presence of either 25 μM anisomycin or 100 μg of cycloheximide per ml from one hour before infection until harvest. Early RNA is isolated from cells in the presence of 100 μg of phosphonoformate (PFA) per ml at 24 hours p.i. Late RNA is isolated from cells at 72 hours p.i.

Fifteen micrograms of total cytoplasmic RNA is electrophoresed through 1.2% formaldehyde agarose gels according to standard protocols (23). The RNA is blotted to Nytran (Scheicher and Schuell, Keene, N.H.), cross-linked by ultraviolet light, and prehybridized for 4–16 hours in 50% formamide, 5×SSC, 5×Denhardts, 50 mM sodium phosphate, pH 6.5, 1% glycine, 100 μg/ml denatured sonicated salmon sperm DNA and 0.1% SDS at 42° C. Using high specific activity riboproves (23), the blots are hybridized in 50% formamide, 5×SSC, 1×Denhardts, 20 mM sodium phosphate, pH 6.5, 1 mM EDTA, 100 μg denatured sonicated salmon sperm DNA per ml, 50 μg yeast tRNA per ml, and 0.1% SDS for 18 hours at 60° C. Riboprobe blots are washed twice in 2×SSC at room temperature for five minutes, and then treated with 1 μg RNAase A per ml in 2×SSC for 15 minutes. This is followed by three high stringency washes in 0.05×SSC/0.1% SDS at 55° C. for 20 minutes. The washed blots are exposed to XAR5 film (Kodak) with DuPont Cronex intensifying screens at −70° C. The high specific activity riboprobes are made according to standard protocols (23). Northern blot analyses are performed on RV134, RV699, RV131 and RV67. The results are as described above and as depicted in FIGS. 3–6.

Example 4

Protein Analysis of Recombinant HCMV

Total protein analysis is conducted for HFF cells infected at an moi=5 with RV134, RV699 or wild-type strain AD169, using uninfected cells as a control. Uninfected or uninfected cell proteins (68–72 hours p.i.) are metabolically labelled with $^{35}$S-methionine/cysteine as follows.

Cells are depleted of methionine and cysteine for 45 minutes prior to labelling by incubation in serum-free DMEM lacking these amino acids (Specialty Media, Lavalette, N.J.). Metabolic radiolabelling of proteins is conducted by adding $^{35}$S-methionine and cysteine (1100 Ci/mmol; ExpreSS; New England Nuclear) to a final concentration of 200 μCi/ml in the same media, but containing dialyzed detal calf serum (Gibco) at a final concentration of 1%. After labelling, cell lysates are prepared by solubilization in triple detergent lysis buffer (23). (The cleared lysates—supernatant after centrifugation for five minutes at 15000 ×g and 4° C.—are also retained for the immunoprecipitation analysis of Example 5.) The cell lysates are electrophoresed in 10% SDS-PAGE and the proteins are also stained with coomassie blue to reveal accumulated proteins. The gel is exposed to x-ray film and photographed. The results are as described above and as depicted in FIG. 7.

Example 5

Immunoprecipitation

Immunoprecipitation analysis is used to determine whether the genes disrupted by the insertions in RV699, RV131 and RV67 are expressed. RV134 is used as a control because its intergenic insertion does not disrupt an open reading frame. US10 or US11 fusion proteins are expressed in *E. coli* strain BL21 from the protein A fusion vector pT7protA which contains the unaltered pRIT2T polylinker 3' of the protein A coding region.

For the US10 or US11 fusions, bases 14119 to 13127 or bases 14834 to 14189, respectively, are inserted in frame into the polylinker. Accordingly, the US10 fusion contains all except the N-terminal eight amino acids of the US10 open reading frame and the US11 fusion contains all except the N-terminal 11 amino acids of the US11 open reading frame. The fusion proteins are solubilized and purified from inclusion bodies of bacteria induced with IPTG.

Monospecific polyclonal antisera is obtained from rabbits after immunization with the fusion proteins. New Zealand white rabbits are immunized at six week intervals with these fusion protein antigens by subcutaneous injection using either Freund's complete adjuvant (primary immunization) or Freund's incomplete adjuvant (secondary immunizations). Serum is obtained after the fifth boost. The radiolabelled cell lysates from Example 4 are again used. The results are as described above and as depicted in FIG. 8.

Example 6

One Step Growth Curve

Confluent monolayers of HFF cells in 35 mm plates are infected at moi=2 with either wild type or recombinant HCMV. Following adsorption for two hours at 37° C., the inoculum is removed and fresh media is added to each plate. The plates are incubated at 37° C. until the indicated day p.i. The plates are frozen at −70° C., thawed at 37° C., and infected cells are scraped into the media. The media/infected-cell suspension is sonicated for one minute. Total infectious virus is quantitated by plaque assay with 0.5% agarose overlay. The results are as described above and as depicted in FIG. 9.

Example 7

Screening for Inhibitors of HCMV

The screening assay utilizes media which comprises minimal essential medium (manufactured by Cellgrow, distributed by Fisher Scientific), a high glucose medium suitable for growth of fibroblasts, supplemented with 10% fetal bovine serum (FBS). Dilutions of test compound in media of 1:25 and 1:2500 are prepared.

HCMV containing the gene for β-glucuronidase is prepared for the assay by diluting to 1:4000 in 2% FBS virus maintenance medium (high glucose).

The assay is performed on a Biomek 1000 work station in 96-well tissue culture plates. Each well contains 3–5 ×10$^4$ human foreskin fibroblast cells, seeded a day prior to initiation of the assay. To initiate the assay, the media over the cells in each well is replaced with fresh media as is described in the following sentences. The cells in each of the eight wells of the first column on each plate are uninfected, and contain 100 μl of media, thereby serving as a negative control.

The second column of eight wells contains cells with 50 μl of the diluted RV145, such that the multiplicity of infection is approximately 0.01, and the final volume in each well is 100 μl. The wells of the second column lack the test compound, so that these serve as a positive control.

The remaining ten columns of eight wells contain cells with 50 μl of media containing dilutions of a test compound (described above). The cells are infected with 50 μl of the diluted RV145 (as above), and the final volume in each well is 100 μl. If desired, separate media can be prepared, each with a different test compound, so that one plate can be used to assay multiple test compounds.

After the appropriate wells of the plate have been infected, the plate is incubated for five days at 37° C. in a $CO_2$ incubator. The plate is then aspirated and 100 μl of a reagent mixture is added. The reagent mixture includes a 0.1% NP-40, a non-ionic detergent, 0.1% sarkosyl, an ionic detergent, and 0.1 mg/ml muglucronide (methylumbelliferylglucuronide, Sigma Chemical) in a lac z buffer (0.06M $Na_2HPO_4$ ; 0.04M $NaH_2PO_4$; 0.01M KCl; 0.001M $MgSO_4$).

The detergents serve to break open the cells, resulting in solubilization of the β-glucuronidase. This permits the levels of the enzyme to be assayed by fluorimetry as described below. At the same time, the detergents kill the virus, making it practical to work with the virus samples.

Muglucuronide is a conjugate of methylumbelliferin and a sugar. In this conjugated form, no fluorescence is emitted. However, β-glucuronidase cleaves the conjugate, freeing the methylumbelliferin, which is a fluorescing compound.

The place is incubated for 20–30 minutes at 37° C. The levels of fluorescence are then measured on a microfluorimeter. The negative control (column 1) provides a baseline reading, because the fibroblasts are uninfected. Column 2 lacks the test compound and provides a positive control, because the fibroblasts are infected with HCMV which contains the gene for expression of β-glucuronidase, which when expressed cleaves the conjugate, allowing the fluorescing compound to be measured.

The remaining columns contain infected fibroblasts together with dilutions of the test compound. If the test compound does inhibit HCMV, the virus will express β-glucuronidase at levels comparable to the positive control, which will be reflected in comparable fluorescence readings. If the test compound inhibits HCMV, the expression of β-glucuronidase is reduced, leading to reduced cleavage the conjugate and, in turn, lower fluorescence readings.

For comparison purposes between test compounds, it is useful to ascertain fluorescence readings at which HCMV is inhibited by fifty percent ($IC_{50}$). Using the assay method described above, the $IC_{50}$ for a known HCMV inhibitor, FOSCAVIR™ Foscarnet, Astra), is 30–40 μM.

Example 8

Mutant RV670 does not induce early CPE. In the course of studying HCMV gene function through the use of an insertional mutagenesis strategy, a viral recombinant mutant, RV670, is isolated having a deletion of a 9-kb region from the left end (prototype arrangement) of the S component (41). Nine major open reading frames are deleted from the genome of this mutant, including IRS1, US1–US3, US6–US9, and US11 (3). Even with such a large number of genes deleted, RV670 grows in tissue cultured HFF cells as efficiently as the wild-type strain, and is neither temperature-sensitive or cold-sensitive (41). However, unlike the wild-type strain, infection by RV670 does not induce the contractile-like rounding of HFF cells typically observed at early times p.i., early CPE (36, 37, and 47). HFF cells infected with the wild-type strain at a multiplicity of infection of 2 display the rounded phenotype: such rounding begins to occur by 6 hours, and reaches a maximum by 16–24 hours p.i. (FIG. 10A; 33). However, RV670 infected cells infected at the same multiplicity retain the typical fibroblastoid morphology at 24 hours p.i. (FIG. 10B). HFF cells infected with RV670 at higher multiplicities (i.e. 5 or 10) or examined at other times p.i. never display early CPE. Although the genes missing from RV670 are clustered, the kinetics of cytoplasmic RNA from the previously studied open reading frames of this group vary. US3-derived transcripts are detected at immediate-early, early, and late times p.i.; US6-, US8-, US9-, and US11-derived messages appear at early times p.i., and US7-derived mRNAs are detected at late times p.i. (38, 45, 51, 17). Expression from IRS1, US1, and US2 are not reported. Although a viral early gene function is predicted to be required for the rounding phenotype, it is not possible to predict which of the genes deleted from the RV670 genome are necessary, based soley on the RNA expression data.

Expression from IRS1 is required for early CPE. To identify the gene deleted from the RV670 genome which is required for early CPE, additional viral recombinant mutants are made using the β-glucuronidase replacement mutagenesis strategy as described hereinabove. Several new mutants deleted of specific genes are constructed: RV35, deleted of US6 through US11; RV47, deleted of US2 and US3; RV5122, deleted of US1; and RV46, deleted of IRS1. The extent of the replacements in each mutant, as well as the size of relevant restriction fragments, are shown schematically in FIG. 11. The indicated genomic organization of these mutants is verified by DNA blot analysis (FIG. 12). Using a β-glucuronidase (FIG. 12A), XX-3.6 (FIG. 12B), and XP (FIG. 12C) probes, all the expected restriction fragments hybridize for each viral recombinant.

Multiple hybridizing fragments in the HindIII digestion lanes are indicative of hybridization to joint and terminal region DNAs. In addition, several probes from other regions of the viral genome, including the L component, are used and no unexpected deletions or rearrangements are detected. RNA blot analysis also is consistent with the conclusion that the proper recombination occurs in each case.

Figure 13A:
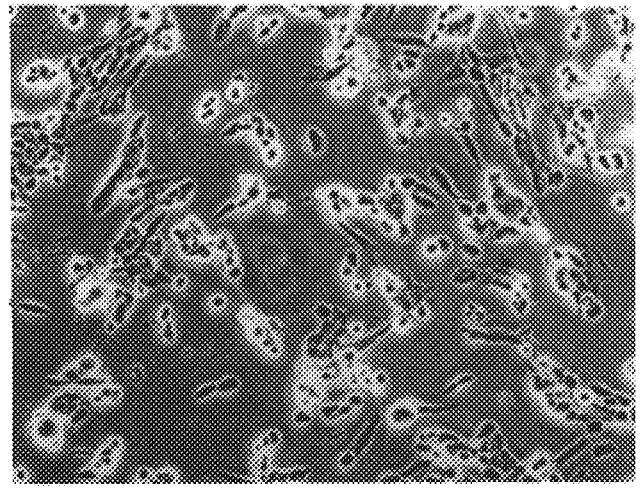
Figure 13B:
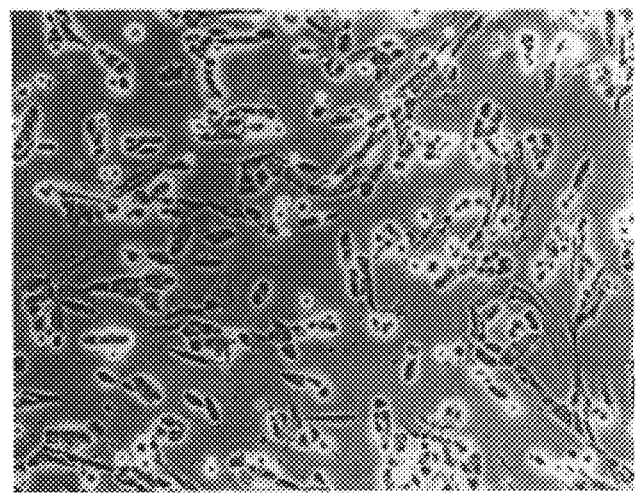
Figure 13C:
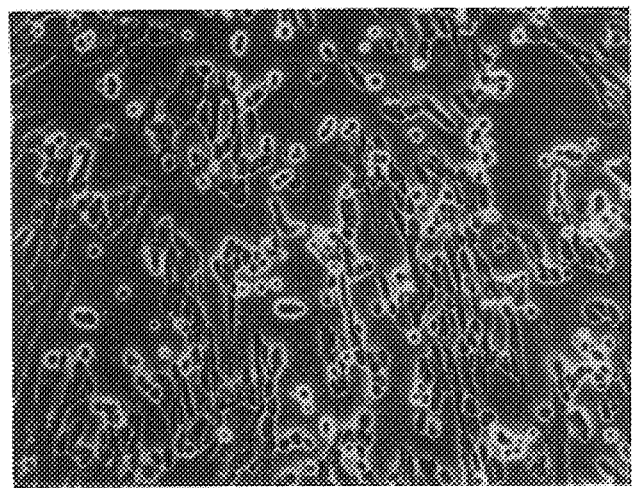
Figure 13D:
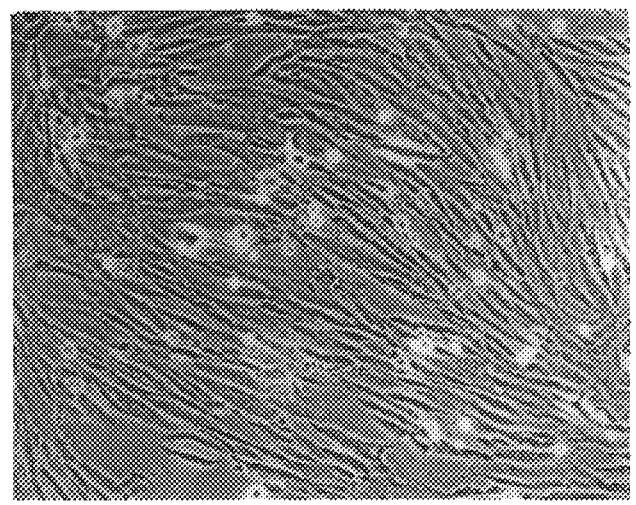
Figure 13E:
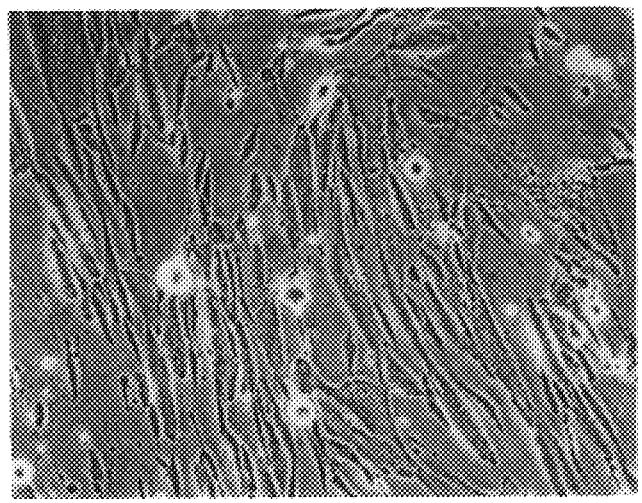
Figure 13F:
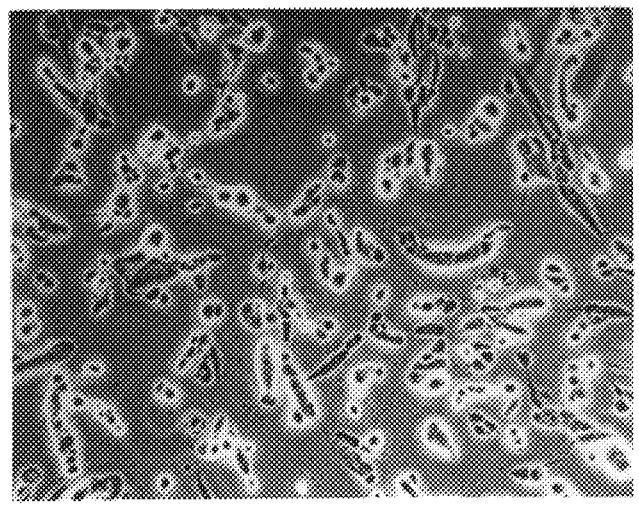

The recombinant viruses are used to assess their ability to cause early CPE. HFF cells are infected at a multiplicity of infection of 2, 5, or 10 and monitored twice daily. At 24 hours p.i. at a multiplicity of infection of 2, RV5122, RV47, and RV35 each retain the ability to induce early rounding; but RV46 lost this ability (FIGS. 13A–D, respectively). Infection by RV46 at a multiplicities of infection of 5 or 10, or observation at other times p.i., yielded essentially identical results. One difference consistently noted is that at the higher multiplicities of infection, cell fusion is very extensive in RV46-infected cells (FIG. 13E) compared to cells infected with the other mutants or the wild-type strain (FIG. 13F). In addition, all other independent isolates of viral recombinant which contain the identical replacement of the IRS1 gene region as RV46 are unable to induce early CPE.

Figure 14A:
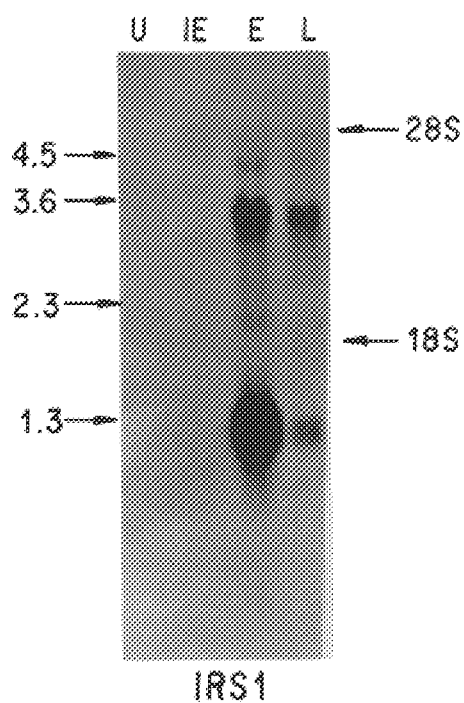
Figure 14B:
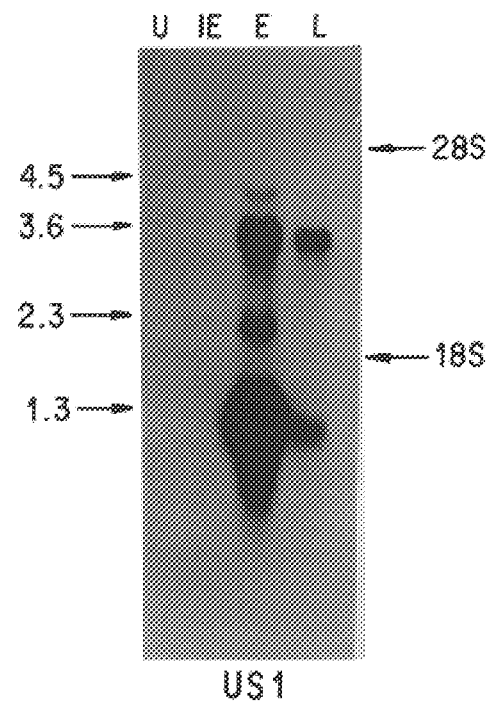
Figure 14C:
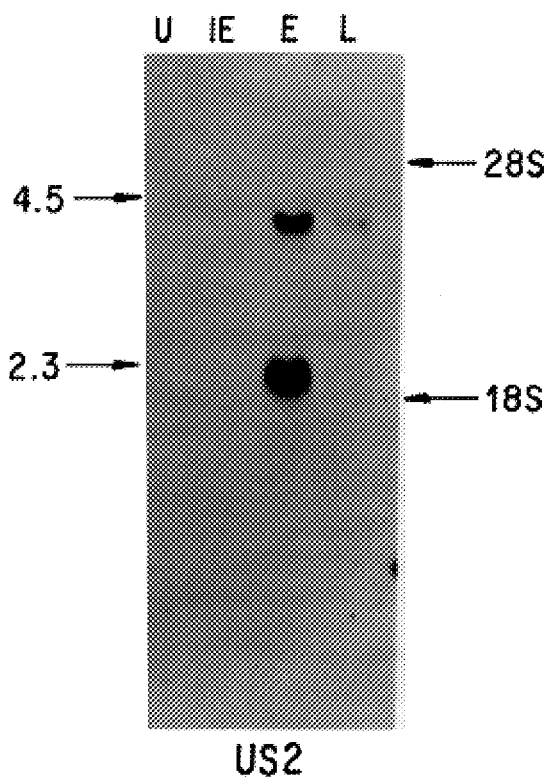
Figure 14D:
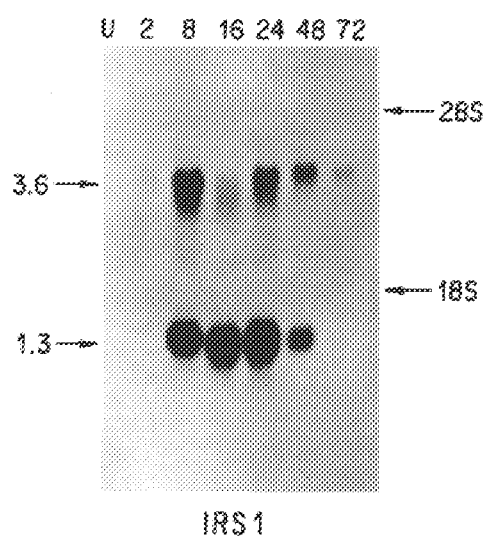
Figure 14E:
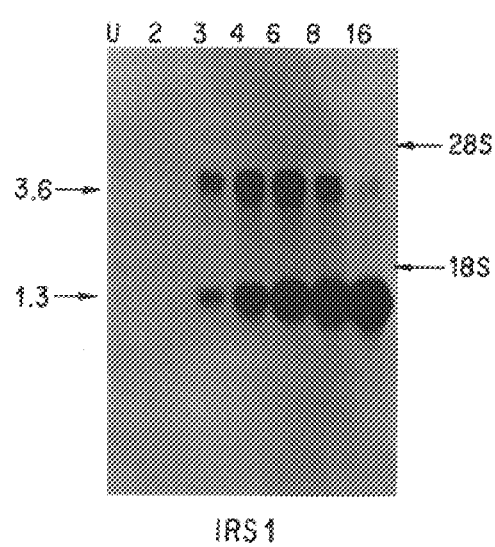

RNA expression from IRS1. The data from recombinant virus studies indicate that expression from the IRS1 region is required for induction of the early rounding phenotype. The IRS1 open reading frame is partially within repeated ($IR_S$) and unique ($U_S$) sequences and encodes a 846 amino acid protein whose N-terminal 529 amino acids are identical to the putative product of the TRS1 open reading frame which occupies an analogous position at the other end of the S component (3, 14). In order to determine the kinetics of RNA expression from IRS1, RNA blot analysis was performed using a riboprobe complementary to the unique, but not the repeated, region sequences comprising the C-terminal region of IRS1 (FIG. 14A). This probe hybridizes to two species of cytoplasmic RNAs: a 3.6-kb transcript which is detected under early and late conditions, although more abundant under early conditions; and a 1.3-kb message is very abundant under early conditions and barely detectable under late conditions. To correlate the expression of one of these messages with the occurrence of the rounded phenotype, cytoplasmic RNAs are isolated from HCMV wild-type strain-infected HFF cells at various times p.i. in the absence of drugs. As shown in FIG. 14D, the expression of the 1.3-kb message peaks in the 16-24 hour range and then sharply diminishes in abundance thereafter. Steady-state cytoplasmic levels of the 3.6-kb transcript are most abundant by 8 hours and slowly decrease throughout the remainder of infection. It is noted that the level of this message is substantially reduced at 16 hour p.i., compared to 8 or 24 hours p.i. (FIG. 14D). Such a decrease from 8 to 16 hours p.i. is reproducible (FIG. 14E). An additional RNA blot experiment demonstrated that the cytoplasmic appearance of both transcripts is present by 3 hours p.i. (FIG. 14E). Thus, the two messages which are expressed from IRS1 appeared at early times p.i., and correlated with the occurrence of early CPE.

From the DNA sequence data, Weston and Barrell (14) reported that there was a TATA box promoter motif approximately 100-bases upstream of the putative translation initiation codon of IRS1, near base 4147, and that the first downstream polyadenylation signal for that strand was on the distal side of US1, near base 7546 (i.e. IRS1 transcripts would contain sequences derived from the US1 gene region). Allowing for 200-bases of poly A, the 3.6-kb transcript is consistent with an RNA initiating and terminating at those locations. To test the prediction that the IRS1-derived transcripts utilize the polyadenylation signal on the distal side of US1, RNA blot and S1 nuclease analyses is performed. As shown in FIG. 14B, using a riboprobe containing US1 sense sequences (so it would not hybridize with US1-derived mRNAs, but only to RNAs from the other strand, such as IRS1-encoding messages), the hybridization profile is identical to that using the IRS1 unique region riboprobe (FIG. 14A). This suggested that these two IRS1-derived messages are transcribed through the US1 gene region and may indeed utilize the AATAAA polyadenylation signal adjacent to US1. In blots of FIGS. 14A and 14B, both riboprobes also hybridize to 2 other less abundant messages of 2.4- and 4.5-kb. To determine whether these latter RNAs are simply readthrough transcripts which utilize the second encountered AATAAA polyadenylation signal (located near base 8406, between US2 and US3), a riboprobe containing US2 sense sequences (so it would not hybridize with US2-derived RNAs, but only to RNAs from the other strand, such as the proposed IRS1-derived readthrough transcripts) is used (FIG. 14C). That riboprobe hybridizes only to the low abundance 2.4-kb and 4.5-kb messages, thereby establishing that these are the readthrough transcripts. Similar readthrough mRNAs are described previously from neighboring areas of the HCMV $U_S$ region (17).

The structure of the major early class IRS1-derived mRNAs (1.3 and 3.6-kb) are determined by S1 nuclease protection and primer extension analyses. These studies confirm that both messages are unspliced and polyadenylated at the site on the distal side of US1. The 5' end of the 1.3-kb transcript is within the US region of IRS and is slightly heterogeneous: a major start site at base 6325, and a minor start site at 6323. This is within the 30-b downstream from a TATA box promoter motif at 6296. S1 nuclease protection analyses places the 5' end of the 3.6-kb mRNA at about 0.1-kb 5' of the putative initiation codon of IRS1, near base 4179, which is within 30-b of the previously noted TAT box promoter motif (51). Thus, the 3.6-kb mRNA initiates just upstream of IRS1 and is continuous from there until the polyadenylation addition site adjacent to US1.

Effect of altered expression of the IRS1 region. Since both IRS1-derived mRNAs are transcribed through the US1 open reading frame before reaching a polyadenylation signal, this provides the opportunity to correlate early CPE with expression of the IRS1 region in a dose dependent fashion. HCMV recombinant RV51 is constructed such that it is deleted of the same region of US1 as is RV122, except that in this case the β-glucuronidase expression cassette is inserted in the opposite orientation (FIG. 17B). This change should result in the IRS1-derived transcripts containing an additional 2.33-kb of β-glucuronidase expression cassette sequences near their 3' end. However, their 5' region which contained the IRS1 sequences remains unaltered. (When the β-glucuronidase gene is inserted in a similar fashion near the 3' end of a US11 protein-encoding transcription unit in mutant RV131, US11 protein (encoded from the 5' most open reading frame of that message) is synthesized in markedly reduced amounts (17), probably due to reduced efficiency of transcriptional and/or post-transcriptional mechanisms.) It is desired that the β-glucuronidase expression cassette insertion of the 3' end of the IRS1 mRNAs have a similar effect on the expression of their respective IRS1 gene-derived protein products. In fact, the steady-state cytoplasmic levels of the two new IRS1 sequence-containing transcripts, 3.6- and 5.9-kb, are reduced in comparison to their wild-type counterparts, the 1.3- and 3.6-kb messages, respectively (FIG. 18). To test the effect of this alteration in IRS1 gene expression, HFF cells are infected at a multiplicity of 2 or 10. At 24 hours p.i., cells infected at a multiplicity of 2 did not display the early rounding phenotype (FIG. 19A). However, at a multiplicity of 10, RV51 is able to induce the phenotype (FIG.19B), similar to cells infected with the wild-type strain (FIG. 19C). In contrast, cells infected with the IRS1 mutant RV46 at that multiplicity displayed extensive fusion, but not rounding (FIG. 19D). These data suggest that HCMV-induced early cell rounding requires expression of the IRS1 gene region in a dose-dependent fashion.

The IRS1 1.3-kb mRNA encodes a function required for early CPE. The IRS1 sequences deleted from the genome of the IRS1 recombinant mutant RV46 extends from the beginning of that open reading frame to the NarI site at base 6336, which is downstream of the 1.3-kb mRNA transcription initiation site. Thus, neither of the two IRS1-derived early class messages are synthesized in RV46-infected cells, most of the IRS1 coding region contained within the 3.6-kb mRNA are deleted, as is the promoter and 11-b of 5' untranslated sequences for the 1.3-kb transcript. To determine whether the 3.6 kb RNA transcription unit product is required for early CPE, the recombinant virus mutant RV5151 is constructed (FIG. 15B). DNA blot analysis, as described previously, confirmed the proper genome structure. In this virus, the β-glucuronidase marker gene replaces the IRS1 N-terminal sequences to the NruI site at base 5934, thereby deleting most of the 3.6-kb mRNA transcription unit. The 1.3-kb mRNA transcription unit is predicted to be unaffected since sequences 0.39-kb upstream of the initiation site of that transcript (i.e. the promoter region) and all of the transcribed region remained intact. Examination of HFF cells infected with RV5151 at a multiplicity of infection of 2 indicates that this mutant retained the ability to induce early CPE (FIG. 16) and thus implicated the 1.3-kb transcription unit protein product as being required for early CPE.

Utility of the IRS1 gene product required for early CPE. HCMV is associated with many disease states in the human host, including atherosclerosis and encephalitis. Both human umbilical vein endothelial cells as well as human brain capillary endothelial cells, undergo morphological alterations after infection by HCMV. Especially in the case of infection of the latter cells, the cytopathology occurs at early times p.i. Such morphological alterations of these endothelial cells may result in a disruption of the blood-brain barrier and allow access to the brain other viruses or compounds which are not found there, thus leading to the encephalitis or atherosclerosis. It is possible that as with HCMV-infected fibroblasts, a IRS1 gene product is required for such morphological alterations of the cell. Thus, screening for inhibitor of the protein product of the 1.3-kb IRS1-derived transcription unit is useful to reduce the severity of these conditions.

Samples of the plasmid (designated pIRS1US1-NS) containing the promoter and open reading frame of the IRS1 gene 1.3-kb transcription unit from human cytomegalovirus has been deposited with the American Type culture Collection (ATCC) 12301 Parklawn Drive, Rockville Md. 20852, U.S.A. the provisions of the Budapest Treaty for the International Recognition of Microorganisms for the Purposes of Patent Procedure.

REFERENCES

1. Alford, C. A., and W. J. Britt, Cytomegalovirus, p. 1981–2010. In D. M. Knipe and B. N. Fields (eds.), *Virology*, 2nd ed., Raven Press, N.Y. (1990).
2. Stinski, M. F., Cytomegalovirus and its replication. p. 1959–1980 in D. M. Knipe and B. N. Fields (eds.), *Virology*, 2nd ed. Raven Press, N.Y. (1990).
3. Chee, M.S., et al., *Curr. Top. Microbiol. Immunol.*, 154, 125–169 (1990).
4. Post, L. E., and B. Roizman, *Cell*, 25, 227–232 (1981).
5. Post, L. E., et al., *Cell*, 24, 555–565 (1981).
6. Longnecker, R., and B. Roizman, *J. Virol.*, 58, 583–591 (1986).
7. Longnecker, R., and B. Roizman. *Science*, 236, 573–576 (1987).
8. Jenkins, F. J., et al., *Proc. Natl. Acad. Sci. USA*, 82, 4773–4777 (1985).
9. Weber, P. C., et al., *Science*, 235, 576–579 (1987).
10. Goldstein, D. J., and S. K. Weller, *J. Virol.*, 62, 196–205 (1988).
11. Goldstein, D. J., and S. K. Weller, *J. Virol.*, 62, 2970–2977 (1988).
12. Spaete, R. R., and E. S. Mocarski, *Proc. Natl. Acad. Sci. USA*, 84, 7213–7217 (1987).
13. Jefferson, R. A., et al., *J. Mol. Biol.*, 193, 41–46 (1987).
14. Weston, K., and B. G. Barrell, *J. Mol. Biol.*, 192, 177–208 (1986).
15. Gretch, D. R., et al., *J. Virol.*, 62, 875–881 (1988).
16. Gretch, D. R., et al., *J. Virol.*, 62, 1956–1962 (1988).
17. Jones, T. R., and V. P. Muzithras, *J. Virol.*, 65, 2024–2036 (1991).
18. Welch, A. R., et al., *J. Virol.*, 65, 3915–3918 (1991).
19. Jefferson, R. A., et al., *Proc. Natl. Acad. Sci. USA*, 83, 8447–8451 (1986).
20. Luckow, V. A., and M.D. Summers, *Virology*, 170, 31–39 (1989).
21. Paigen, K., *Ann. Rev. Genet.*, 13, 417–466 (1979).
22. Greenaway, P. J., and G. W. G. Wilkinson, *Virus Res.*, 7, 17–31 (1987).
23. Sambrook, J., et al., *Molecular cloning: a laboratory manual*, 2nd ed. Cold Spring Harbor Laboratory Press, Cold Spring Harbor, N.Y. (1989).
24. Smith, J. D., and E. De Harven, *J. Virol.*, 12, 919–930 (1873).
25. Rapp, R., The biology of cytomegaloviruses, p. 9, In B. Roizman (ed.), *The Herpesviruses*, vol. 2. Plenum Press, N.Y. (1983).
26. Holland, L. E., et al., *J. Virol.*, 49, 947–959 (1984).
27. Longnecker, R. S. et al., *Proc. Natl. Acad. Sci. USA*, 84, 4303–4307 (1987).
28. Schranz, P., et al., *Virology*, 170, 273–276 (1989).
29. Ligas, M. W., and D. C. Johnson, *J. Virol.*, 62, 1486–1494 (1988).
30. Chang, A. C. Y., and Cohen, S. N., *J. Bacteriol.*, 134, 1141–1156 (1978).
31. Oram, J. D., et al., *J. Gen. Virol.*, 59, 111–129 (1982).
32. McKnight, S. L., *Nucleic Acids Res.*, 8, 5949–5964 (1980).
33. Albrecht, T., et al., *Subcell. Biochem.*, 15, 157–202 (1989).
34. Albrecht, T. et al. *Life Sci.*, 32, 2273–2278 (1983).
35. Bruggerman, C. A. et al., *Thromb. Haemost.*, 59, 264–268 (1988).
36. Fioretti, A. et al., *J. Virol.*, 11, 998–1003.
37. Furukawa, T. et al., *J. Virol.*, 11, 991–997 (1973).
38. Gretch, D. R. and Stinski, M. F., *Virology*, 174, 522–532 (1990).
39. Ho, D. D., et al. *J. Infect. Dis.*, 150, 956–957 (1984).
40. Ho, M.(ed.), "Cytomegalovirus", 2nd ed., Plenum Publishing Corp., N.Y. (1991).
41. Jones, T. R. and Muzithras, V.P., *J. Virol.*, 66, 2541–2546 (1992).
42. Lathey, J. L., et al., *Virology*, 176, 266–273 (1990).
43. Moffatt, B. A. and Studier, F. W., *Cell*, 49, 221–227 (1987).
44. Petrie, B. L., et al., *J. Infect. Dis.*, 155, 158–159 (1987).
45. Tenney, D. J. and Colberg-Poley, *J. Virol.*, 65, 6724–6734 (1991).
46. Rosenberg, A. H., et al., *Gene*, 56, 125–135 (1987).
47. Smith, J. D. and deHarven, E., *J. Virol*, 12, 919–930 (1973).
48. Stasiak, P. C. and Mocarski, E. S., *J. Virol.*, 66, 1050–1058 (1992).
49. Waner, J. L. and Weller, T. H., *Proc. Soc. Exp. Biol. Med.*, 145, 379–384 (1974).
50. Waldman, W. J., et al., *J. Med. Virol.*, 28, 223–230 (1989).
51. Weston, K., *Virology*, 162, 406–416 (1988).
52. Wu. T. C. et al., *Am. J. Path.*, 140, 739–774 (1992).
53. Maniatis, T. et al., "Molecular Cloning: A Laboratory Manual" Cold Spring Harbor Laboratory (1982).

What is claimed is:

1. A method for identifying a compound which inhibits HCMV replication which comprises:
  (a) inserting a β-glucuronidase marker gene into the HCMV genome to construct an HCMV recombinant in a manner selected from the group consisting of:
    (i) replacing a portion of a wild-type HCMV gene, such that the insertion of the marker gene prevents the expression of the product of the wild-type gene;
    (ii) adding to a wild-type HCMV gene, so as to disrupt the wild-type gene, such that the insertion of the marker gene prevents the expression of the product of the wild-type gene;
    (iii) replacing portions of two or more wild-type HCMV genes, such that the insertion of the β-glucuronidase marker gene prevents the expression of the products of those wild-type genes; and
    (iv) inserting the β-glucuronidase marker gene between two HCMV genes, such that no HCMV genes are replaced or disrupted and all HCMV gene products are expressed;
  (b) inserting the recombinant HCMV constructed in step (a) into a suitable mammalian host cell;
  (c) growing the host cell under suitable conditions to favor HCMV replication;
  (d) measuring the amount of any β-glucuronidase produced;
  (e) repeating steps (c)–(d) in the presence of the test compound; and
  (f) comparing the results of (d) and (e), a reduction or inhibition of the amount of β-glucuronidase produced in the presence of the test compound indicating that the test compound inhibits HCMV replication.

2. The method of claim 1, wherein the measurement of β-glucuronidase in step (d) comprises contacting the β-glucuronidase with a conjugated chemical substrate under conditions such that a fluorescing product is released from the conjugated chemical substrate and measured.

3. The method of claim 1, wherein the measurement of β-glucuronidase in step (d) comprises contacting the β-glucuronidase with a conjugated chemical substrate under conditions such that a chromophoric product that undergoes a color change upon cleavage from the substrate is released from the conjugated chemical substrate and measured.

4. The method of claim 2, wherein the conjugated chemical substrate is methylumbelliferylglucuronide and the fluorescing product is methylumbelliferin.

5. The method of claim 2, wherein the amount of the fluorescing product is measured on a microfluorimeter and a test compound is identified as an inhibitor of HCMV replication by a decrease in microfluorimeter readings.

6. The method of claim 3, wherein the conjugated chemical substrate is p-nitrophenyl-β-D-glucuronide or 5-bromo-4-chloro-3-indolyl-β-D-glucuronide.

7. The method of claim 3, wherein the color change is measured visually or spectrophotometrically.

* * * * *